United States Patent
Szczepanski et al.

(10) Patent No.: US 6,316,389 B1
(45) Date of Patent: Nov. 13, 2001

(54) DIHYDROBENZENE PESTICIDES

(75) Inventors: Henry Szczepanski, Wallbach; Martin Zeller, Baden, both of (CH); Ottmar Franz Hüter, Lörrach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/202,887

(22) PCT Filed: Jun. 16, 1997

(86) PCT No.: PCT/EP97/03114

§ 371 Date: Dec. 22, 1998

§ 102(e) Date: Dec. 22, 1998

(87) PCT Pub. No.: WO97/49672

PCT Pub. Date: Dec. 31, 1997

(30) Foreign Application Priority Data

Jun. 25, 1996 (CH) .................................................. 1589/96

(51) Int. Cl.⁷ .......................... A01N 37/08; C07C 233/58; C07D 295/084; C07D 333/16
(52) U.S. Cl. .......................... 504/218; 504/223; 504/239; 504/242; 504/247; 504/254; 504/263; 504/266; 504/267; 504/270; 504/273; 504/277; 504/278; 504/283; 504/284; 504/289; 504/299; 540/544; 544/162; 544/335; 544/336; 544/353; 546/137; 546/147; 546/300
(58) Field of Search .................. 560/125, 126, 560/128; 540/544; 544/162, 335, 336, 353; 546/137, 147, 300; 548/136, 170, 187, 217, 263.2, 306.4, 324.1; 549/507, 556, 77, 65, 451, 479; 558/230, 252; 504/218, 223, 242, 239, 247, 254, 263, 266, 267, 270, 273, 278, 277, 283, 284, 289, 299

(56) References Cited

U.S. PATENT DOCUMENTS

| 4,829,085 | 5/1989 | Wenderoth et al. | 514/522 |
| 5,189,063 | 2/1993 | Klausener et al. | 514/530 |
| 5,196,423 | 3/1993 | Mueller et al. | 514/255 |

FOREIGN PATENT DOCUMENTS

| 178826 | 4/1986 | (EP) . |
| 253213 | 1/1988 | (EP) . |
| 421102 | 4/1991 | (EP) . |
| 438726 | 7/1991 | (EP) . |

Primary Examiner—Mark L. Berch
Assistant Examiner—Thomas C McKenzie
(74) Attorney, Agent, or Firm—Joseph C. Gil

(57) ABSTRACT

Compounds of the formula I

I in which:
where:
 X is CH or N;
 Y is O; S, S=O or $NR_5$;
 Z is $OR_2$, $SR_2$, $N(R_3)R_4$; or
 Y and Z together form 5- to 7-membered ring which contains, 2 or 3 hetero atoms O and/or N and which is unsubstituted or substituted by $C_1$–$C_4$alkyl, halo-$C_1$–$C_4$alkyl, halogen, =O or cyclopropyl;
 V is a direct bond or $C_1$–$C_6$alkylene, which is unsubstituted or substituted by $C_1$–$C_3$alkyl, $C_2$–$C_3$alkylidene or $C_3$–$C_6$cycloalkylidene;
 U is O, S, $NR_7$, SO or $SO_2$;
 W is substituted or unsubstituted aryl or substituted or unsubstituted heteroaryl;
 $R_1$ is cyclopropyl, $C_1$–$C_6$alkyl or halo-$C_1$–$C_6$alkyl;
 $R_2$ and $R_3$ independently of one another are $C_1$–$C_6$alkyl or halo-$C_1$–$C_6$alkyl;
 $R_4$ and $R_5$ independently of one another are hydrogen, $C_1$–$C_6$alkyl or $C_1$–$C_6$alkoxy;
 $R_7$ is hydrogen, $C_1$–$C_6$alkyl, benzyl, $C_1$–$C_6$alkylcarbonyl, halo-$C_1$–$C_6$alkylcarbonyl, halo-$C_2$–$C_6$alkenylcarbonyl;
 $R_{21}$ and $R_{22}$ independently of one another are hydrogen, halogen, $C_1$–$C_8$alkyl or $C_1$–$C_8$alkoxy or $C_1$–$C_8$alkylthio;
 $R_{23}$, $R_{24}$, $R_{25}$, $R_{26}$ independently of one another are hydrogen, halogen, $C_1$–$C_8$alkyl or $C_1$–$C_8$alkoxy; are pesticidally active.

They can be used for pest control, in particular as fungicides, acaricides and insecticides in crop protection.

26 Claims, No Drawings

DIHYDROBENZENE PESTICIDES

This application is a national stage application under 35 USC 371 of international application FPCT/EP97/03114, filed Jun. 16, 1997, which claims priority from Swiss application 1589/96, filed Jun. 25, 1996.

The invention relates to a novel pesticidally active compound of the formula I

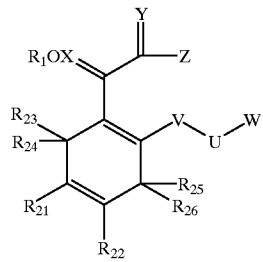

where:
- X is CH or N;
- Y is O; S, S=O or $NR_5$;
- Z is $OR_2$, $SR_2$, $N(R_3)R_4$; or
- Y and Z together form a 5- to 7-membered ring which contains 2 or 3 hetero atoms O and/or N and which is unsubstituted or substituted by $C_1$–$C_4$alkyl, halo-$C_1$–$C_4$alkyl, halogen, =O or cyclopropyl;
- V is a direct bond or $C_1$–$C_6$alkylene which is unsubstituted or substituted by $C_1$–$C_3$alkyl, $C_2$–$C_3$alkylidene or $C_3$–$C_6$cycloalkylidene;
- U is O, S, $NR_7$, SO or $SO_2$;
- W is substituted or unsubstituted aryl or subsituted or unsubstituted hetaryl;
- $R_1$ is cyclopropyl, $C_1$–$C_6$alkyl or halo-$C_1$–$C_6$alkyl;
- $R_2$ and $R_3$ independently of one another are $C_1$–$C_6$alkyl or halo-$C_1$–$C_6$alkyl;
- $R_4$ and $R_5$ independently of one another are hydrogen, $C_1$–$C_6$alkyl or $C_1$–$C_6$alkoxy;
- $R_7$ is hydrogen, $C_1$–$C_6$alkyl, benzyl, $C_1$–$C_6$alkylcarbonyl, halo-$C_1$–$C_6$alkylcarbonyl, halo-$C_2$–$C_6$alkenylcarbonyl;
- $R_{21}$ und $R_{22}$ independently of one another are hydrogen, halogen, $C_1$–$C_8$alkyl or $C_1$–$C_8$alkoxy or $C_1$–$C_8$alkylthio;
- $R_{23}$, $R_{24}$, $R_{25}$, $R_{26}$ independently of one another are hydrogen, halogen, $C_1$–$C_8$alkyl or $C_1$–$C_8$-alkoxy.

The formula I embraces all stereoisomeric forms and mixtures of these, such as racemic and diasteromeric mixtures, for example E/Z mixtures, The compounds according to the invention have fungicidal, acaricidal and insecticidal properties and are suitable as active ingredients for use in agriculture, in horticulture and in the hygiene sector. The invention furthermore relates to the preparation of these compounds, to agrochemical compositions which comprise, as active ingredients, at least one of these compounds, and to the use of the active ingredients or of the compositions for protecting plants against attack by harmful microorganisms, and for controlling insects.

2-alkoximino-2-phenylacetic acid derivatives and 2-alkoxymethylene-2-phenylacetic acid derivatives as pesticides are disclosed, for example, in EP-A-253 213 and EP-A-178 826. Corresponding pesticide compounds which have a cyclohexenyl group instead of the phenyl group are described in EP-A-421 102, those in which the phenyl group is replaced by a cyclohexyl group in EP-A-438 726. The phytofungicidal activity of 1,4-cyclohexadiene-1-alanine is furthermore described in J. of Antibiotics, Vol. XXIII, No.11, pp.537–541 (1970).

The general terms used hereinabove and hereinbelow have the meanings given hereafter, unless otherwise defined:

Aryl is phenyl, naphthyl, phenanthryl or fluorenyl, in particular phenyl.

Hetaryl are 5- or 6-membered aromatic rings which have hetero atoms N, O and/or S, and which can be benzo-fused. Examples are furane, pyrrole, pyridine, pyrimidine, pyrazine, thiazole, oxazole, isoxazole, isothiazole, triazine, quinoline, isoquinoline, pyridazine, pyrazole, imidazole, quinazoline, quinoxaline, benzimidazole, benzofuran, indole, isoindole, benzothiazole, benzoxazole.

Heterocyclyl denotes 5- to 7-membered non-aromatic rings which contain 1–3 identical or different hetero atoms N, O, S. Examples are $\Delta^2$-oxazoline, $\Delta^2$-thiazoline; 5,6-dihydro-4H-1,3-thiazine; 5,6-dihydro-4H-1,3-oxazine, pyrrolidine, indoline, piperidine, morpholine, 4-alkylpiperidine, azepine.

Alkyl groups are straight-chain or branched, depending on the number of the carbon atoms, for example methyl, ethyl, n-propyl, iso-propyl, n-butyl, sec-butyl, iso-butyl, tert-butyl, sec-amyl, tert-amyl, 1-hexyl or 3-hexyl.

Unsaturated hydrocarbon radicals are alkenyl, alkynyl or alkenynyl groups having not more than 3 multiple bonds, for example butadienyl, hexatrienyl, 2-penten-4-ynyl.

Alkenyl is to be understood as meaning straight-chain or branched alkenyl, for example allyl, methallyl, 1-methylvinyl or but-2-en-1-yl. Preferred alkenyl radicals are those which have a chain length of 3 to 4 carbon atoms.

Alkynyl can also be straight-chain or branched, depending on the number of the carbon atoms, for example ethynyl, propargyl, but-1-yn-1-yl, but-1-yn-3-yl. Propargyl is preferred.

Halogen or halo are fluorine, chlorine, bromine or iodine, preferably fluorine, chlorine or bromine.

Haloalkyl can contain identical or different halogen atoms, for example fluoromethyl, difluoromethyl, difluorochloromethyl, trifluoromethyl, chloromethyl, dichloromethyl, trichloromethyl, 2,2,2-trifluoroethyl, 2-fluoroethyl, 2-chloroethyl, 2,2,2-trichloroethyl, 3,3,3-trifluoropropyl.

Alkoxy is, for example, methoxy, ethoxy, propyloxy, i-propyloxy, n-butyloxy, iso-butyloxy, sec-butyloxy and tert-butyloxy; preferably methoxy and ethoxy.

Haloalkoxy is, for example, difluoromethoxy, trifluoromethoxy, 2,2,2-trifluoroethoxy, 1,1,2,2-tetrafluoroethoxy, 2-fluoroethoxy, 2-chloroethoxy and 2,2-difluoroethoxy.

Cycloalkyl is cyclopropyl, cyclobutyl, cyclopentyl or cyclohexyl.

Alkanoyl is either straight-chain or branched; examples are formyl, acetyl, propionyl, butyryl, pivaloyl or octanoyl.

All the alkyl, alkenyl, alkynyl, haloalkyl, haloalkenyl, haloalkoxy and alkanoyl groups mentioned hereinabove and hereinbelow can be substituted by aryl, hetaryl, aryloxy, hetaryloxy, arylsulfenyl, arylsulfinyl, arylsulfonyl, heterarylsulfenyl, hetarylsulfinyl or heterarylsulfonyl, each of which is unsubstituted or additionally substituted. All the aryl and hetaryl groups mentioned hereinabove and hereinbelow can be mono- or polysubstituted, for example by halogen, $C_1$–$C_4$alkyl, $C_2$–$C_4$alkenyl, $C_2$–$C_4$alkynyl, $C_1$–$C_4$alkoxy, $C_1$–$C_4$alkylthio, $C_1$–$C_4$haloalkyl, $C_2$–$C_4$haloalkenyl, $C_2$–$C_4$-haloalkynyl, $C_1$–$C_4$haloalkoxy, halogen, cyano, cyano-$C_1$–$C_2$alkyl, cyano-$C_1$–$C_2$alkoxy, OH, $NO_2$, SCN, thiocyanomethyl, $Si(CH_3)_3$, $NH_2$, $NH(C_1$–$C_4$alkyl), $N(C_1$–$C_4$alkyl)$_2$, $C_1$–$C_4$alkoxymethyl, $C_1$–$C_4$haloalkylcarbonyl, $C_1$–$C_4$haloalkyloxycarbonyl, $C_1$–$C_4$alkylcarbonyl, $C_1$–$C_4$-alkoxycarbonyl, aminocarbonyl, $C_1$–$C_4$alkylaminocarbonyl, bis($C_1$–$C_4$alkylamino)carbonyl, arylaminocarbonyl, arylaminothiocarbonyl, $C_1$–$C_4$alkoximinomethyl, —$CSNH_2$, —SH, $C_1$–$C_4$alkylthiomethyl, $C_2$–$C_4$alkenyloxy, $C_2$–$C_4$alkynyloxy, $C_2$–$C_4$haloalkenyloxy, $C_1$–$C_4$alkylsulfinylmethyl, $C_1$–$C_4$alkylsulfonylmethyl, phenylsulfinylmethyl, phenylsulfonylmethyl, trifluoromethylsulfonyl, $C_3$–$C_6$cycloalkyl, $C_1$–$C_4$haloalkylcarbonyloxy, $C_1$–$C_4$alkylcarbonyloxy, $C_1$–$C_4$alkoxycarbonyloxy, haloalkoxycarbonyloxy, aminocarbonyloxy, $C_1$–$C_4$alkylaminocarbonyloxy, bis($C_1$–$C_4$alkylamino)carbonyloxy, arylaminocarbonyloxy, arylaminothiocarbonyloxy.

All the abovementioned enumerations are by way of example and not by limitation.

Preferred are the following groups:

(1) Compounds of the formula I in which:

W is a group a)

in which

D are identical or different substituents halogen, cyano, nitro, $C_1$–$C_{12}$alkyl, halo-$C_1$–$C_6$ alkyl, $C_2$–$C_{12}$alkenyl, halo-$C_2$–$C_{12}$alkenyl, $C_2$–$C_{12}$alkynyl, halo-$C_2$–$C_{12}$alkynyl, free or halogenated $C_3$–$C_6$cycloalkyl, free or halogenated $C_3$–$C_6$cycloalkylmethyl, free or halogenated $C_3$–$C_6$cycloalkylmethyloxy, $C_1$–$C_4$alkoxy, halo-$C_1$–$C_4$alkoxy, $C_2$–$C_6$alkenyloxy, halo-$C_2$–$C_6$alkenyloxy, $C_2$–$C_6$alkynyloxy, halo-$C_2$–$C_6$alkynyloxy, $C_2$–$C_{12}$alkoxyalkyl, $C_1$–$C_4$alkoxycarbonyl, $C_1$–$C_6$alkylcarbonyl, it being possible for all the abovementioned alkyl, alkenyl or alkynyl groups to be substituted by aryl or hetaryl, aryloxy or hetaryloxy, arylsulfenyl, arylsulfinyl, arylsulfonyl, hetarylsulfenyl, hetarylsulfinyl or hetarylsulfonyl radicals, each of which can be additionally substituted or unsubstituted; furthermore substituted or unsubstituted aryl, substituted or unsubstituted hetaryl, substituted or unsubstituted heterocyclyl, substituted or unsubstituted arylcarbonyl, substituted or unsubstituted aryloxy, substituted or unsubstituted benzyl, substituted or unsubstituted cyclohexenyl, substituted or unsubstituted cyclohexenylalkoxy, substituted or unsubstituted cyclohexenylalkylthio, substituted or unsubstituted cyclohexadienyl, substituted or unsubstituted cyclohexadienylalkoxy, substituted or unsubstituted cyclohexadienylalkylthio, substituted or unsubstituted fused ring having up to 14 C atoms, or in which D is once the group

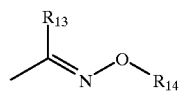

in which $R_{13}$ is hydrogen, cyano, $C_1$–$C_6$alkyl, $C_3$–$C_6$cycloalkyl, $C_1$–$C_6$alkoxycarbonyl, $C_1$–$C_6$acyl, $C_1$–$C_2$-alkoximino-$C_1$–$C_6$alkyl, aryl, hetaryl, heterocyclyl, naphthyl; $C_1$–$C_6$alkoxy, aryloxy, hetaryloxy, $C_1$–$C_6$alkylamino, bis($C_1$–$C_6$-alkyl)amino, arylamino, hetarylamino, in which all the abovementioned radicals (with the exception of cyano) can be unsubstituted or substituted by alkyl, alkoxy, haloalkyl, haloalkoxy, alkylthio, alkylsulfenyl, alkylsulfinyl, halogen, nitro, cyano, aryl, aryloxy, hetaryl, hetaryloxy; or $R_{13}$ is the group

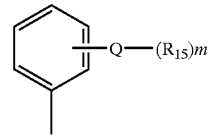

in which $R_{15}$ is hydrogen, $C_1$–$C_6$alkyl, halo-$C_1$–$C_6$alkyl, $C_1$–$C_6$alkoxy, halo-$C_1$–$C_6$alkoxy, halogen, $C_3$–$C_6$cycloalkyl which is unsubstituted or substituted by 1 to 5 halogen atoms, $C_2$–$C_6$alkenyl; halo-$C_2$–$C_6$alkenyl, substituted or unsubstituted $C_2$–$C_6$alkynyl; aryl, hetaryl or heterocyclyl, all three of which independently of one another are unsubstituted or monosubstituted to pentasubstituted by $C_1$–$C_6$alkyl, halo-$C_1$–$C_6$alkyl, halogen, $C_1$–$C_6$alkoxy or halo-$C_1$–$C_6$alkoxy; tri($C_1$–$C_4$-alkyl)silyl, di($C_1$–$C_4$-alkyl)phenylsilyl;

where, if m is greater than 1, the radicals $R_{15}$ can be identical or different;

Q is a direct bond, $C_1$–$C_8$alkylene, $C_2$–$C_6$alkenylene, $C_2$–$C_6$alkynylene, O, O($C_1$–$C_6$alkylene), ($C_1$–$C_6$alkylene)O, S($=$O)$_p$, S($=$O)$_p$($C_1$–$C_6$alkylene) or ($C_1$–$C_6$alkylene)S($=$O)$_p$;

n is 0, 1, 2, 3, 4 or 5;

m is 0, 1, 2, 3, 4 or 5;

p is 0, 1 or 2; and $R_{14}$ is hydrogen; $C_1$–$C_6$alkyl; $C_1$–$C_6$haloalkyl having 1 to 15 halogen atoms; $C_1$–$C_4$alkoxy-$C_1$–$C_2$alkyl; $C_2$–$C_4$alkenyl-$C_1$–$C_2$alkyl which is unsubstituted or substituted by 1 to 3 halogen atoms; $C_2$–$C_4$alkynyl-$C_1$–$C_2$alkyl; $C_3$–$C_6$cycloalkyl which is unsubstituted or substituted by 1 to 4 halogen atoms; $C_3$–$C_6$cycloalkyl-$C_1$–$C_4$alkyl which is unsubstituted or substituted by 1 to 4 halogen atoms; cyano-$C_1$–$C_4$alkyl; $C_1$–$C_4$alkoxycarbonyl-$C_1$–$C_4$alkyl; phenyl-$C_1$–$C_3$alkyl which is unsubstituted or substituted by halogen, $C_1$–$C_3$alkyl, $C_1$–$C_4$alkoxy, $C_1$–$C_4$haloalkyl, cyano, nitro, $C_1$–$C_4$alkylenedioxy, it being possible for the phenyl group to be substituted by 1 to 3 identical or different substitutents; phenyl which is unsubstituted or monosubstituted or disubstituted by independent substituents from the series consisting of $C_1$–$C_4$alkyl, $C_1$–$C_4$alkoxy, halogen, $C_1$–$C_2$haloalkyl having 1 to 3 halogen atoms, nitro or cyano; pyridyl which is unsubstituted or monosubstituted or disubstituted by independent substituents from the series consisting of $C_1$–$C_4$alkyl, $C_1$–$C_4$alkoxy, halogen, $C_1$–$C_2$haloalkyl having 1 to 3 halogen atoms, nitro or cyano.

(2) Compounds of the formula I in which:

$R_1$ is methyl;

$R_2$, $R_3$ and $R_5$ independently of one another are $C_1$–$C_2$alkyl, preferably methyl;

$R_4$ is hydrogen.

(3) Compounds of the formula I in which:

X is N;

Y is O; S, or S=O, preferably O;

Z is $OR_2$, $SR_2$, $N(R_3)H$; preferably $OR_2$, $SR_2$;

$R_2$ and $R_3$ are $C_1$–$C_2$alkyl, preferably methyl.

(4) Compounds of the formula I in which:

X is CH;

Y is O; S, or S=O, preferably O;

Z is $OR_2$;

$R_2$ is $C_1$–$C_2$-Alkyl, preferably methyl.

(5) Compounds of the formula I in which Y and Z together are a group a)

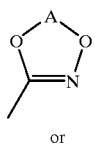

or b)

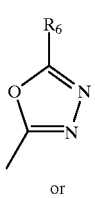

or c)

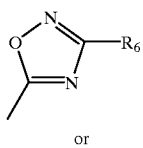

or d)

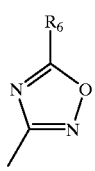

and in which:

A is alkanediyl having 1 to 3 carbon atoms which is unsubstituted or substituted by methyl, preferably dimethylene(ethane-1,2-diyl);

$R_6$ is hydrogen, $C_1$–$C_3$alkyl, cyclopropyl or $CF_3$;

(6) Compounds of the formula I in which:

V is —$CH_2$—, —$CH(CH_3)$—, —$CH(CH_3)_2$—, —$(CH_2)_2$—, —$(CH_2)_3$—;

U is O;

$R_{21}$ and $R_{22}$ independently of one another are hydrogen, chlorine, bromine, $C_1$–$C_4$alkyl or $C_1$–$C_4$alkoxy, in particular methyl;

$R_{23}$, $R_{24}$, $R_{25}$, $R_{26}$ are hydrogen.

(7) Compounds of the formula I in which:

X is CH or N;

Y is O;

Z is $OCH_3$ or $NHCH_3$;

V is —$CH_2$—;

U is O;

W is substituted or unsubstituted phenyl;

$R_{21}$ and $R_{22}$ independently of one another are hydrogen, chlorine or methyl, in particular methyl;

$R_{23}$, $R_{24}$, $R_{25}$, $R_{26}$ are hydrogen.

(8) Amongst (7) in particular compounds of the formula I in which:

W is phenyl which is substituted by $C_1$–$C_8$alkyl, halo-$C_1$–$C_6$alkyl, $C_2$–$C_4$alkenyl, halo-$C_2$–$C_4$alkenyl, $C_2$–$C_4$alkynyl, halo-$C_2$–$C_4$alkynyl, $C_1$–$C_4$alkoxy, halo-$C_1$–$C_4$alkoxy, $C_2$–$C_6$alkenyloxy, halo-$C_2$–$C_4$alkenyloxy, $C_2$–$C_4$alkynyloxy, halo-$C_2$–$C_4$alkynyloxy, $C_1$–$C_4$alkoxycarbonyl, $C_1$–$C_6$alkylcarbonyl, the abovementioned alkyl, alkenyl and alkynyl groups being unsubstituted or further substituted by aryl, hetaryl, aryloxy, hetaryloxy, arylsulfenyl, arylsulfinyl, arylsulfonyl, hetarylsulfenyl, hetarylsulfinyl or hetarylsulfonyl, each of which is unsubstituted or additionally substituted; furthermore aryl, hetaryl, heterocyclyl, arylcarbonyl, aryloxy, benzyl, cycloalkyl, cyclohexenyl, cyclohexenylalkoxy, cyclohexenylalkylthio, cyclohexadienyl, cyclohexadienylalkoxy, cyclohexadienylalkylthio, all the abovementioned cyclic groups being unsubstituted or mono- or polysubstituted by halogen, $C_1$–$C_4$alkyl, $C_2$–$C_4$alkenyl, $C_2$–$C_4$alkynyl, $C_1$–$C_4$alkoxy, $C_1$–$C_4$alkylthio, $C_1$–$C_4$haloalkyl, $C_2$–$C_4$haloalkenyl, $C_2$–$C_4$haloalkynyl, $C_1$–$C_4$haloalkoxy, halogen, cyano, cyano-$C_1$–$C_2$alkyl, cyano-$C_1$–$C_2$alkoxy, OH, $NO_2$, SCN, thiocyanomethyl, $Si(CH_3)_3$, $NH_2$, $NH(C_1$–$C_4$alkyl), $N(C_1$–$C_4$alkyl)$_2$, $C_1$–$C_4$alkoxymethyl, $C_1$–$C_4$haloalkylcarbonyl, $C_1$–$C_4$haloalkyloxycarbonyl, $C_1$–$C_4$alkylcarbonyl, $C_1$–$C_4$alkoxycarbonyl, aminocarbonyl, $C_1$–$C_4$alkylaminocarbonyl, bis($C_1$–$C_4$alkylamino)carbonyl, arylaminocarbonyl, arylaminothiocarbonyl, $C_1$–$C_4$alkoximinomethyl, —$CSNH_2$, —SH, $C_1$–$C_4$alkylthiomethyl, $C_2$–$C_4$alkenyloxy, $C_2$–$C_4$alkynyloxy, $C_2$–$C_4$haloalkenyloxy, $C_1$–$C_4$alkylsulfinylmethyl, $C_1$–$C_4$alkylsulfonylmethyl, phenylsulfinylmethyl, phenylsulfonylmethyl, trifluoromethylsulfonyl, $C_3$–$C_6$cycloalkyl, $C_1$–$C_4$haloalkylcarbonyloxy, $C_1$–$C_4$alkylcarbonyloxy, $C_1$–$C_4$alkoxycarbonyloxy, haloalkoxycarbonyloxy, aminocarbonyloxy, $C_1$–$C_4$alkylaminocarbonyloxy, bis ($C_1$–$C_4$alkylamino)carbonyloxy, arylaminocarbonyloxy or arylaminothiocarbonyloxy.

(9) Compounds of the formula I in which:

V is —$CH_2$—, —$CH(CH_3)$—, —$CH(CH_3)_2$—, —$(CH_2)_2$—, —$(CH_2)_3$—;

U is S or $NR_7$;

$R_{21}$ and $R_{22}$ independently of one another are halogen, chlorine, bromine, $C_1$–$C_4$alkyl or $C_1$–$C_{14}$alkoxy, in particular methyl;

$R_{23}$, $R_{24}$, $R_{25}$, $R_{26}$ are hydrogen.

(10) Compounds of the formula I in which:

D is halogen, $C_1$–$C_4$alkyl, halo-$C_1$–$C_4$alkyl, $C_2$–$C_4$alkenyl, $C_2$–$C_4$alkynyl, free or chlorinated cyclopropylmethyl, $C_1$–$C_4$alkoxy, halo-$C_1$–$C_4$alkoxy, $C_2$–$C_{12}$alkoxyalkyl, $C_1$–$C_4$ acyl, $C_1$–$C_4$alkoxycarbonyl, free or chlorinated cyclopropylmethyloxy, or substituted or unsubstituted aryl, substituted or unsubstituted aryloxy, substituted or unsubstituted benzyl, wherein the substituents on aryl, aryloxy and benzyl are selected from the series consisting of halogen, nitro, $C_1$–$C_2$-alkyl, halo-$C_1$–$C_2$alkyl, $C_2$–$C_4$alkenyl, $C_2$–$C_4$alkynyl, $C_1$–$C_2$alkoxy, halo-$C_1$–$C_2$alkoxy, $C_2$–$C_{12}$alkoxyalkyl;

n is 0, 1, 2 or 3.

(11) Amongst (10), those in which:
D is halogen, $C_1$–$C_4$alkyl, halo-$C_1$–$C_4$alkyl, $C_2$–$C_4$alkenyl, $C_2$–$C_4$alkynyl, free or chlorinated cyclopropylmethyl, $C_1$–$C_4$alkoxy, halo-$C_1$–$C_4$alkoxy, $C_1$–$C_4$ acyl, $C_1$–$C_4$-alkoxycarbonyl, free or chlorinated cyclopropylmethyloxy,
n is 0, 1 or 2.

(12) Compounds of the formula I in which:
D is the group

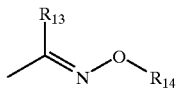

in which
$R_{13}$ is hydrogen, cyano, $C_1$–$C_4$alkyl, cyclopropyl, $C_1$–$C_4$alkoxycarbonyl, $C_1$–$C_4$acyl, $C_1$–$C_2$alkoximino-$C_1$–$C_6$alkyl, or the group

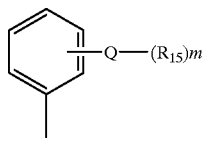

$R_{15}$ is $C_1$–$C_6$alkyl, halo-$C_1$–$C_6$alkyl, $C_1$–$C_6$alkoxy, halo-$C_1$–$C_6$alkoxy, halogen, $C_3$–$C_6$cycloalkyl which is unsubstituted or substituted by 1 to 5 halogen atoms, $C_2$–$C_6$alkenyl; halo-$C_2$–$C_6$alkenyl, substituted or unsubstituted $C_2$–$C_6$alkynyl; aryl, hetaryl or heterocyclyl, all three of which independently of one another are unsubstituted or monosubstituted to pentasubstituted by $C_1$–$C_6$alkyl, halo-$C_1$–$C_6$alkyl, halogen, $C_1$–$C_6$alkoxy or halo-$C_1$–$C_6$alkoxy; tri($C_1$–$C_4$alkyl)silyl, di($C_1$–$C_4$alkyl)phenylsilyl;
where, if m is greater than 1, it is possible for the radicals $R_{15}$ to be identical or different;
Q is a direct bond, $C_1$–$C_8$alkylene, $C_2$–$C_6$alkenylene, $C_2$–$C_6$alkinylene, O, O($C_1$–$C_6$alkylene), ($C_1$–$C_6$alkylene)O, S(=O)$_p$, S(=O)$_p$($C_1$–$C_6$alkylene) or ($C_1$–$C_6$alkylene)S(=O)$_p$;
n is 0, 1, 2, or 3;
m is 0, 1, 2, or 3;
p is 0, 1 or 2; and
$R_{14}$ is hydrogen; $C_1$–$C_4$alkyl; $C_1$–$C_4$haloalkyl having 1 to 6 halogen atoms; $C_2$–$C_4$alkenyl; $C_2$–$C_4$haloalkenyl having 1 to 3 halogen atoms.

(14) Amongst (13), those in which:
$R_{15}$ is $C_1$–$C_6$alkyl, halo-$C_1$–$C_6$alkyl, cyclopropyl which is unsubstituted or substituted by 1 to 5 chlorine atoms, $C_2$–$C_6$alkenyl which is unsubstituted or substituted by 1 to 3 halogen atoms, or unsubstituted or substituted $C_2$–$C_6$alkynyl; furthermore phenyl which is unsubstituted or monosubstituted to pentasubstituted by $C_1$–$C_6$alkyl, halo-$C_1$–$C_6$alkyl, halogen, $C_1$–$C_6$alkoxy or halo-$C_1$–$C_6$-alkoxy; or pyridyl which is unsubstituted or monosubstituted to pentasubstituted by $C_1$–$C_6$alkyl, halo-$C_1$–$C_6$-alkyl, halo, $C_1$–$C_6$alkoxy or halo-$C_1$–$C_6$alkoxy;
Q is a direct bond, $C_1$–$C_4$alkylene, O, O($C_1$–$C_4$alkylene), ($C_1$–$C_4$-alkylene)O,
m is 0, 1, 2.

(14) Amongst (11), those in which:
$R_{13}$ is hetaryl or heterocyclyl which, independently of one another, are unsubstituted or monosubstituted to pentasubstituted by $C_1$–$C_6$alkyl, halo-$C_1$–$C_6$alkyl, halogen, $C_1$–$C_6$-alkoxy or halo-$C_1$–$C_6$-alkoxy.

(15) Compounds of the formula I in which:
W is substituted or unsubstituted pyridyl, pyrimidinyl, imidazolyl, thiazolyl, 1,3,4-thiadiazolyl, triazolyl, thienyl, furanyl, pyrrolyl, quinolyl, isoquinolyl, benzoxazolyl, quinoxalinyl, benzothiazolyl, benzimidazolyl, or indolyl.

(16) Compounds of the formula I in which:
W is pyridyl or pyrimidinyl, each of which is unsubstituted or substituted by $C_1$–$C_4$alkyl, halo-$C_1$–$C_4$alkyl, $C_2$–$C_6$alkenyl, halo-$C_2$–$C_6$alkenyl, $C_2$14 $C_6$alkynyl, halo-$C_2$–$C_6$alkynyl, $C_1$–$C_4$alkoxy, halo-$C_1$–$C_4$alkoxy, $C_2$–$C_{12}$alkoxyalkyl, $C_1$–$C_6$acyl, $C_1$–$C_4$alkoxycarbonyl, substituted or unsubstituted phenyl, substituted or unsubstituted phenoxy, or substituted or unsubstituted benzyl.

(17) Compounds of the formula I in which:
V is a direct bond or —$CH_2$—,
U is O;
W is pyridyl or pyrimidinyl, each of which is unsubstituted or substituted by $C_1$–$C_4$alkyl, halo-$C_1$–$C_4$alkyl, phenyl, phenoxy or benzyl and in which phenyl, phenoxy and benzyl are unsubstituted or monosubstituted to trisubstituted by halogen, $C_1$–$C_4$alkyl, $C_2$–$C_4$alkenyl, halo-$C_1$–$C_4$alkyl, halo-$C_2$–$C_4$alkenyl, $C_1$–$C_4$alkoxy, halo-$C_1$–$C_6$alkoxy or cyano.

Compounds of the formula I can be prepared as shown in reaction scheme 1 and 2, as follows:

Scheme 1

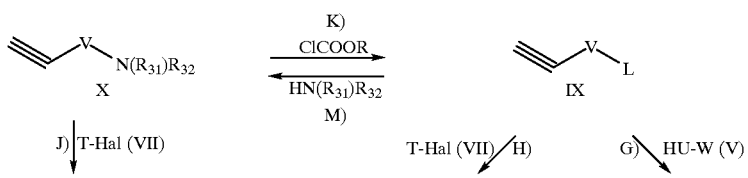

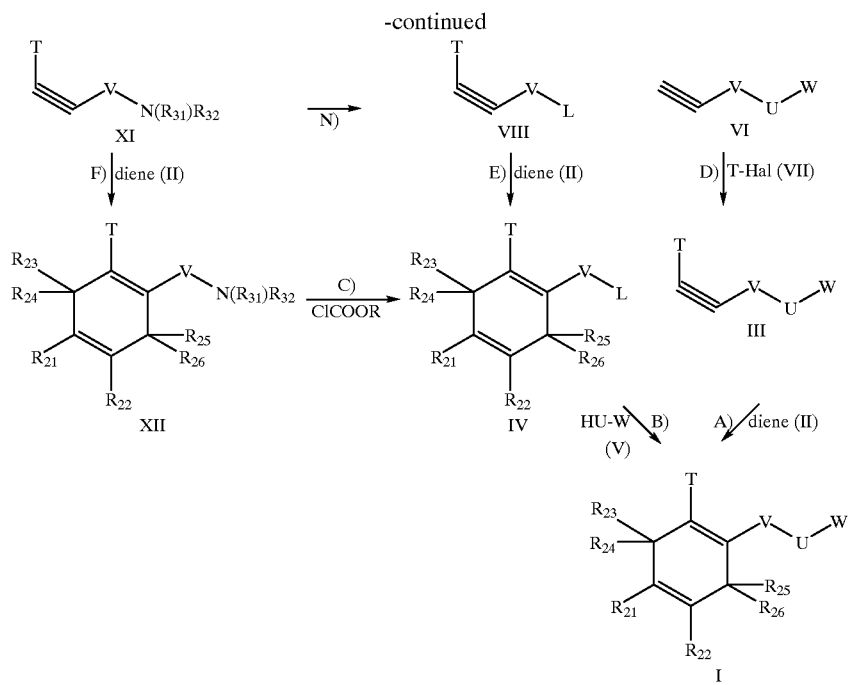
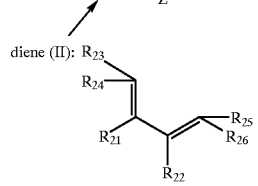
L: leaving group
Hal: halogen, in particular chlorine and bromine
Scheme 2
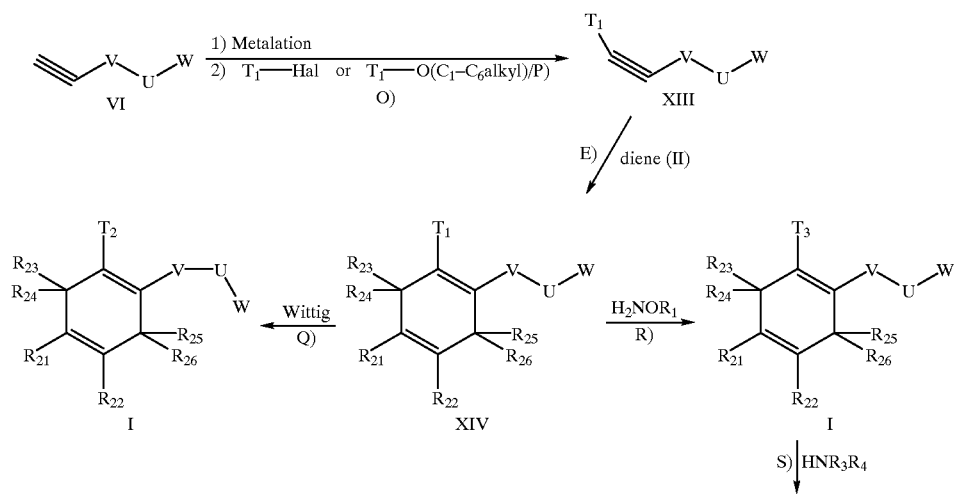

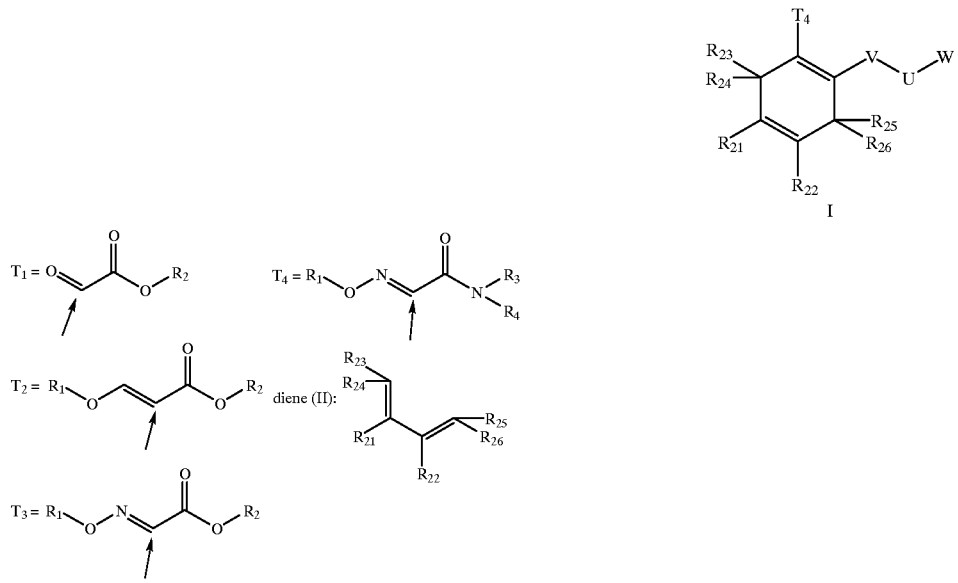

The individual reaction steps can be carried out as follows.

A), E), F) under conditions known from, and applicable to, Diels-Alder reactions, in the presence or absence of solvents, and in the presence or absence of a catalyst; at −40 to 250° C., preferably −20 to 200° C., in particular 100–200° C.

B), G) reaction in a solvent under alkaline conditions.

C), K) reaction with a chloroformic ester in the presence or absence of solvents under anhydrous conditions.

D), H), J) under conditions known for, and applicable to, Heck reactions, in the presence of a Pd catalyst (for example F. A. Carey and R. J. Sundberg, Advanced Organic Chemistry, pages 418–420, Plenum Press 1990).

M) exchange of the leaving group for an amino group under alkaline conditions.

N) Reaction with a chloroformic ester in the presence or absence of solvents, under anhydrous conditions, to give a compound of the formula VIII in which L is chlorine, if desired followed by exchange of the chlorine atom for another leaving group such as bromine, tosylate or mesylate.

O) 1) Metalation with suitable reagents, for example methylmagnesium chloride, sodium hydride, alkyllithium, potassium tertiary-butylate and, if desired, transmetalation with copper iodide or similar salts and 2) subsequent acylation of the metal acetylide with an oxalic acid derivative TCl, in particular with $T_1$—Cl or $T_1$—O($C_1$–$C_5$alkyl) in a solvent.

Q) Wittig reaction, for example with methoxymethyltriphenylphosphonium chloride and base in an inert solvent.

R) oxime formation either (a) with a hydroxylamine derivative of the formula $H_2NOR_1$ in a neutral or alkaline solvent, if appropriate with the addition of a base: or (b) with hydroxylamine $H_2NOH$ or a salt thereof followed by alkylation with an alkylating agent $R_1$—L, in which L is a leaving group.

S) Conversion of an ester into an amide by treating the ester with an amine $HNR_3R_4$ in a suitable solvent. Typical reaction conditions can be seen from the examples.

The cyclohexadiene derivatives of the formulae I, IV XII and XIV can be converted by known methods, either by dehydrogenation to the corresponding aromatic compounds or by hydrogenation into the corresponding cyclohexene or cyclohexane derivatives.

Examples of suitable bases are alkali metal or alkaline earth metal hydroxides, hydrides, amides, alkoxides, carbonates, dialkylamides or alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium carbonate, potassium tert-butoxide, potassium carbonate, lithium diisopropylamide, potassium bis(trimethylsilyl)amide, calcium hydride, triethylamine, triethylenediamine, cyclohexylamine, N-cyclohexyl-N,N-dimethylamine, N,N-diethylaniline, pyridine, 4-(N,N-dimethylamino)pyridine, N-methylmorpholine, benzyltrimethylammonium hydroxide and 1,8-diazabicyclo[5.4.0]undec-5-ene (DBU).

Examples of leaving groups are chlorine, bromine, iodine, $C_1$–$C_8$alkylthio such as methylthio, ethylthio or propylthio, $C_1$–$C_8$alkanoyloxy such as acetoxy, (halo) $C_1$–$C_8$alkanesulfonyloxy such as methanesulfonyloxy, ethanesulfonyloxy or trifluoromethanesulfonyloxy, or substituted or unsubstituted phenylsulfonyloxy such as benzenesulfonyloxy or p-toluenesulfonyloxy, imidazolyl or hydroxyl, preferably chlorine, bromine, iodine, trifluoromethanesulfonyloxy and p-toluenesulfonyloxy.

The reactants can be reacted with each other as such, i.e. without addition of a solvent or diluent, for example, in the melt. In most cases, however, the addition of an inert solvent or diluent or of a mixture of these is advantageous. Examples of such solvents or diluents which may be mentioned are: aromatic, aliphatic and alicyclic hydrocarbons and halohydrocarbons such as benzene, toluene, xylene, chlorobenzene, bromobenzene, petroleum ether, hexane, cyclohexane, dichloromethane, trichloromethane, dichloroethane or trichloroethane; ethers such as diethyl ether, tert-butyl methyl ether, tetrahydrofuran or dioxane; ketones such as acetone or methyl ethyl ketone; alcohols such as methanol, ethanol, propanol, butanol, ethylene glycol or glycerol; esters such as ethyl acetate or butyl acetate; amides such as N,N-dimethylformamide, N,N-dimethylacetamide, N-methylpyrrolidone or hexamethylphosphoric triamide; nitriles such as acetonitrile; and sulfoxides such as dimethyl sulfoxide. Bases employed in an excess, such as triethylamine, pyridine, N-methylmorpholine or N,N-diethylaniline, can also act as solvents or diluents.

The reaction can also be carried out with phase transfer catalysis in an organic solvent, for example methylene chloride or toluene, in the presence of an aqueous alkaline solution, for example sodium hydroxide solution, and of a phase transfer catalyst, for example tetrabutylammonium hydrogen sulfate.

The invention also relates to novel starting materials and intermediates used for the preparation of the compounds of the formula I, their use and processes for their preparation.

The following processes are of particular importance.

(1) The process for the preparation of the compound of the formula I, which comprises reacting a compound of the formula II with the compound of the formula III

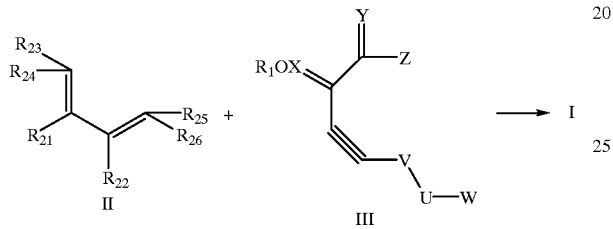

in which X, Y, Z, $R_1$, V, U, W and $R_{21}$ to $R_{26}$ have the meanings given for formula I.

(2) Process for the preparation of a compound of the formula I, which comprises reacting a compound of the formula IV with a compound of the formula V

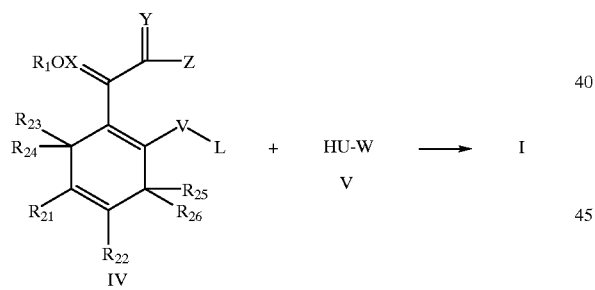

in which X, Y, Z, $R_1$, V, U, $R_{21}$ to $R_{26}$ and W have the meanings given for formula I and in which L is a leaving group in a solvent under alkaline conditions.

(3) Process for the preparation of a compound of the formula XIV which comprises reacting a compound of the formula II with a compound of the formula XIII

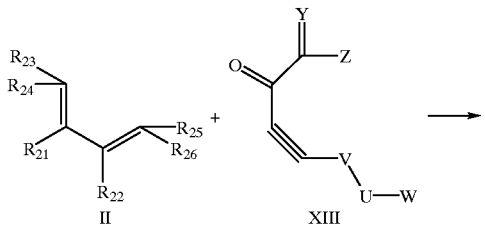

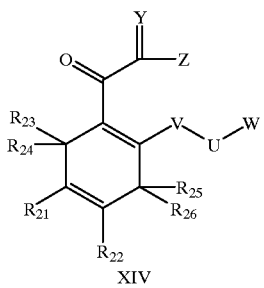

in which Y, Z, V, U, W and $R_{21}$ to $R_{26}$ have the meanings given for formula I according to claim 1.

Especially important are the intermediates of the formulae III, XIII and XIV

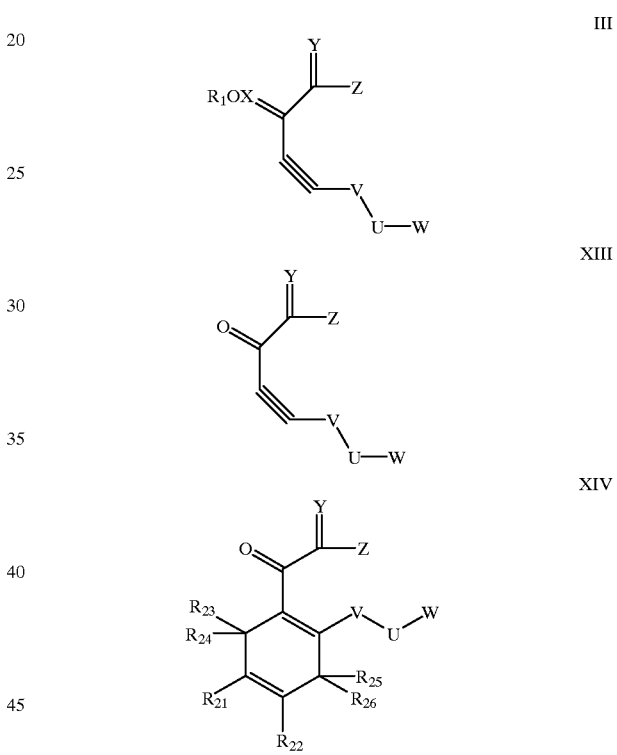

in which X, Y, Z, V, U, W, $R_1$, $R_{21}$ to $R_{26}$ have the meanings given for formula I.

The compounds of the formula T-Hal (VII) in which T has the abovementioned meanings and Hal is halogen can be prepared as described, for example, in WO/20569.

The groups mentioned for X, Y and Z in formula I can be converted into each other by known methods, for example WO 94/26700 and WO 95/04728, both at the final level and at any suitable intermediate level.

The compounds of the formula I can be employed preventively and/or curatively in the agricultural sector and related fields as active ingredients in the control of plant pests. The active ingredients of the formula I according to the invention are distinguished by a good activity, even at low rates of concentration, and by the fact that they are well tolerated by plants and are environmentally friendly. They have very advantageous, in particular systemic, properties and can be employed for protection of a large number of crop plants. Using the active ingredients of the formula I, it is possible to contain or destroy the pests which are found on plants or plant organs (fruits, flowers, foliage, stalks, tubers, roots) of a variety of useful plants, and even plant organs which grow at a later point in time remain unharmed, for example by phytopathogenic microorganisms.

Moreover, the compounds I can be employed as seed-dressing agents for the treatment of seeds (fruits, tubers, kernels) and plant cuttings as a protection against fungal infections and against soil-borne phytopathogenic fungi.

The compounds I act for example against the phytopathogenic fungi which belong to the following classes: Fungi imperfecti (for example Botrytis, Pyricularia, Helminthosporium, Fusarium, Septoria, Cercospora and Alternaria); Basidiomycetes (for example Rhizoctonia, Hemileia, Puccinia); Ascomycetes (for example Venturia and Erysiphe, Podosphaera, Monilinia, Uncinula) and Oomycetes (for example Phytophthora, Pythium, Plasmopara).

Target crops for the application in crop protection are, within the scope of the invention, for example the following plant species: cereals, (wheat, barley, rye, oats, rice, maize, sorghum and related species); beet (sugar and fodder beet); pome fruit, stone fruit, soft fruit (apples, pears, plums, peaches, almonds, cherries, strawberries, raspberries, blackberries); leguminous plants (beans, lentils, peas, soya); oil crops (oil seed rape, mustard, poppies, olives, sunflowers, coconut, castor, cocoa, peanuts); cucurbits (pumpkin, cucumbers, melons); fibre crops (cotton, flax, hemp, jute); citrus fruit (oranges, lemons, grapefruit, tangerines); various vegetables (spinach, lettuce, asparagus, cabbages, carrots, onions, tomatoes, potatoes, bell peppers); the laurel family (avocado, Cinnamonium, camphor), and plants such as tobacco, nuts, coffee, aubergines, sugar cane, tea, pepper, grapevines, hops, the plantain family, latex plants and ornamentals.

The compounds of the formula I according to the invention are furthermore valuable active ingredients against insects and pests from the order Acarina, as found on useful plants and ornamentals in agriculture, in horticulture and in forests, while being well tolerated by warm-blooded species, fish and plants. The compounds of the formula I are particularly suitable for controlling pests in cotton, vegetable, fruit and rice crops, such as spider mites, aphids, caterpillars of lepidopterans and rice leafhoppers. Pests which can be controlled are mainly spider mites such as *Panonychus ulmi*, aphids such as *Aphis craccivora*, caterpillars lepidopterans, such as those of *Heliothis virescens*, and rice leafhoppers such as *Nilaparvata lugens* or *Nephotettix cincticeps*. The good pesticidal activity of the compounds I according to the invention corresponds to a mortality of at least 50–60% of the abovementioned pests.

Further fields of application of the active ingredients according to the invention are the protection of stored products and of materials, in which case the stored material is protected against rotting and becoming mouldy and also against animal pests (for example grain weevil, mites, maggots and the like). In the hygiene sector, compounds of the formula I effect successful control of animal parasites such as ticks, mites, warble flies and the like on domestic animals and productive livestock. The compounds I act against individual or all developmental stages of normally sensitive, but also resistant species of pests. In the present context, their activity may become apparent for example in destruction of the pests, either immediately or only after some time has elapsed, for example during ecdysis, or in a reduced oviposition and/or hatching rate.

Active ingredients I are normally used in the form of compositions and can be applied to the plant or area to be treated simultaneously with other active ingredients, or in succession. These other active ingredients can be, for example, fertilizers, trace element mediators or other preparations which affect plant growth. In this context, selective herbicides, but also insecticides, fungicides, bactericides, nematicides, molluscicides or mixtures of a plurality of these together with, if desired, other carriers conventionally used in the art of formulation, surfactants of other application-enhancing additives may also be used.

Suitable carriers and additives can be solid or liquid and are substances expediently used in the art of formulation, for example natural or regenerated mineral substances, solvents, dispersants, wetting agents, tackifiers, thickeners, binders or fertilizers.

A preferred process for applying an active ingredient of the formula I, or of an agrochemical composition which comprises at least one of these active ingredients, is application to the foliage (foliar application). Frequency and rate of application depend on the risk of infestation with the pathogen in question. Alternatively, the active ingredients I can reach the plant through the soil via the root system (systemic action), by drenching the locus of the plant with a liquid preparation or by incorporating the substances into the soil in solid form, for example in the form of granules (soil application). In the case of paddy rice, such granules can be metered into the flooded paddy field. Alternatively, the compounds I can be applied to seed kernels for the purposes of seed treatment (coating), either by soaking the kernels or tubers in a liquid preparation of the active ingredient or by coating them with a solid preparation.

The compounds I are employed as such or, preferably, together with the auxiliaries conventionally used in the art of formulation. To this end, they are processed in a known manner, expediently to give, for example, emulsion concentrates, spreadable pastes, directly sprayable or dilutable solutions, dilute emulsions, wettable powders, soluble powders, dusts or granules, for example by encapsulation in, for example, polymeric substances. The methods of application, such as spraying, atomizing, dusting, scattering, brushing on or pouring, and the type of composition are selected to suit the intended aims and prevailing circumstances.

Useful rates for application are, generally, 1 g to 2 kg of active substance (a.s.) per hectare (ha), preferably 10 g to 1 kg of a.s./ha, in particular 20 g to 600 g a.s./ha. When used as a seed-dressing agent, it is advantageous to use doses of from 10 mg to 1 g of active substance per kg of seed.

The formulations, i.e. the compositions, preparations or products comprising the active ingredient of the formula I and, if desired, a solid or liquid additive, prepared in the manner known per se, for example by intimately mixing and/or grinding the active ingredient with extenders, such as solvents, solid carriers and, if desired, surface-active compounds (surfactants).

The following are suitable as solvents: aromatic hydrocarbons, preferably the fractions $C_8$ to $C_{12}$, such as xylene mixtures or substituted napthalenes, phthalic esters such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl ether or ethylene glycol monoethyl ether, ketones such as cyclohexanone, strongly polar solvents such as N-methyl-2-pyrrolidone, dimethyl sulfoxide or dimethylformamide, and free or epoxidized vegetable oils, such as epoxidized coconut oil or soya oil, and water.

Solid carriers which are used, for example, for dust and dispersible powders are, as a rule, ground natural minerals such as calcite, talc, kaolin, montmorillonite or attapulgite. To improve the physical properties, it is also possible to add highly disperse silica or highly disperse absorptive polymers. Suitable particulate, adsorptive carriers for granules are porous types, such as pumice, brick grit, sepiolite or bentonite, and suitable non-sorptive carrier materials are, for example, calcite or sand. In addition, a large number of pregranulated materials of inorganic or organic nature, such as dolomite or comminuted plant residues, may be used. Surface-active compounds are, depending on the nature of the active ingredient of the formula I to be formulated, non-ionic, cationic and/or anionic surfactants which have good emulsifying, dispersing and wetting properties. Surfactants are also to be understood as meaning surfactant mixtures.

Suitable anionic surfactants can be both so-called water-soluble soaps and water-soluble synthetic surface-active compounds.

Examples of non-ionic surfactants which may be mentioned are nonylphenylpolyethoxyethanoles, castor oil polyglycol ethers, polypropylene/polyethylene oxide adducts, tributylphenoxypolyethylenethanol, polyethylene glycol and octylphenoxypolyethoxyethanol. Fatty acid esters of polyoxyethylenesorbitan, such as polyoxyethylenesorbitan trioleate, are furthermore also suitable.

The cationic surfactants are mainly quaternary ammonium salts which have, as N-substituents, at least one alkyl radical having 8 to 22 C atoms and, as further substituents, lower, free or halogenated alkyl, benzyl or lower hydroxyalkyl radicals.

Other surfactants conventionally used in the art of formulation are known to those skilled in the art or can be found in the relevant specialist literature.

As a rule, the agrochemical preparations comprise 0.1 to 99 percent by weight, in particular 0.1 to 95 percent by weight, of active ingredient of the formula I, 99.9 to 1 percent by weight, in particular 99.8 to 5 percent by weight, of a solid or liquid additive and 0 to 25 percent by weight, in particular 0.1 to 25 percent by weight, of a surfactant.

While more concentrated compositions are preferred as commercially available goods, the end user uses, as a rule, dilute compositions.

The compositions may also comprise other additives such as stabilizers, antifoams, viscosity regulators, binders or tackifiers, and also fertilizers or other active ingredients for achieving specific effects.

PREPARATION EXAMPLES

Temperatures in ° Celsius. Abbreviations: Me=methyl; Et=ethyl; Pr=n-propyl; i-Pr=isopropyl; Bu=butyl; i-Bu= isobutyl; Ph=phenyl; THF=tetrahydrofuran; TPP= triphenylphosphine H-1: 1-methyl-2-(prop-2-ynyloxy)benzene 245 g of potassium carbonate and 75 ml of propargyl chloride are added to a solutions of 96 g of o-cresol in 1500 ml of acetonitrile. The mixture is now heated for 14 hours at 65°, cooled to room temperature, and filtered with suction, and the filtrate is evaporated. The residue is taken up in 150 ml of ethyl acetate, the mixture is filtered with suction and the filtrate is evaporated. This gives 134 g of the total compound as a pale brown oil.

H-2: methyl methoxyimino-5-o-tolyloxypent-3-ynoate (Comp. 16.004)

60 g of 1-methyl-2-prop-2-ynyloxybenzene, 0.3 g of copper(I) iodide and 1 g of Pd(TPP)$_2$Cl$_2$ are added to a solution of 39.5 g of monomethyl 2-methoxyiminomonochlorooxalate in 1000 ml of triethylamine and 80 ml of THF. The mixture is now stirred for 14 hours at 80°. The mixture is subsequently filtered with suction and the filtrate is evaporated. The oily residue is chromatographed on silica gel (ether/hexane 1:2) and the combined fractions are evaporated. This gives 44 g of the title compound.

H-3: methyl(4,5-dimethyl-2-o-tolyloxymethylcyclohexa-1,4-dienyl)methoxyimino acetate (Comp. 2.002)

20 ml of 2,3-dimethylbuta-1,3-diene are added to a solution of 7.5 g of methyl 2-methoxyimino-5-o-tolyloxypent-3-ynoate in 5 ml of toluene. The reaction mixture is heated for 14 hours at 130° in an autoclave. It is subsequently evaporated and the residue is chromatographed on silica gel. 8 g of the title compound are obtained as a resin.

H-4: N-methyl-2-(4,5-dimethyl-2-o-tolyloxymethylcyclohexa-1,4-dienyl)-2-methoxyiminoacetamide (Comp. 3.002)

10 ml of methylamine solution (5N in methanol) are added to a solution of 2 g of methyl(4,5-dimethyl-2-o-tolyloxymethylcyclohexa-1,4-dienyl)methoxyiminoacetate in 10 ml of methanol. The mixture is stirred for 6 hours at approximately 40°. It is subsequently evaporated and the residue is chromatographed on silica gel. 1.8 g of the title compound are obtained as colourless crystals of m.p. 96–98°.

H-5: methyl(2,6-dimethylmorpholin-4-yl)-2-methoxyiminopent-3-ynoate (cis and trans)

9 g of methyl 2-methoxyiminochlorooxalate, 0.1 g of copper(I) iodide and 0.3 g of Pd(TPP)$_2$Cl$_2$ are added to a solution of 7.65 g of 2,6-dimethyl-4-prop-2-ynylmorpholine (cis/trans mixture) in 200 ml of triethylamine and 50 ml of THF. The mixture is now stirred for 14 hours at 80°. It is subsequently filtered with suction and the residue is evaporated. The oily residue is chromatographed on silica gel (ether/hexane 1:2). This gives 2.1 g of oil of the title compound (trans) and 4.2 g of oil of the title compound (cis).

H-6: methyl[2-(2,6-dimethylmorpholin-4-ylmethyl)-4,5-dimethylcyclohexa-1,4-dienyl] methoxyiminoacetate 7.5 ml of 2,3-dimethylbuta-1,3-diene are added to a solution of 3.3 g of methyl 5-(2,6-dimethylmorpholin-4-yl)-2-methoxyimino-pent-3-ynoate (cis) in 5 ml of toluene. The reaction mixture is heated for 14 hours at 130° in an autoclave. It is subsequently evaporated and the residue is chromatographed on silica gel. 2.6 g of the title compound are obtained as resin.

H-7: methyl 2-methoxyimino-5-morpholin-4-yl-pent-3-ynoate 7.6 g of methyl 2-methoxyiminochlorooxylate and 0.1 g of copper(I) iodide and 0.3 g of Pd(TPP)$_2$Cl$_2$ are added to a solution of 6.25 g of 4-prop-2-ynylmorpholine in 250 ml of triethylamine and 30 ml of THF. The mixture is now stirred for 14 hours at 80°. It is subsequently filtered off with suction and filtrate is evaporated. The oily residue is chromatographed on silica gel (ethyl acetate/hexane 4:1). This gives 6.65 g of crystals of the title compound of melting point 43–45°.

H-8: methyl(4,5-dimethyl-2-morpholin-4-ylmethylcyclohexa-1,4-dienyl)methoxyiminoacetate 10 ml of 2,3-dimethylbuta-1,3-diene are added to the solution of 4.8 g of methyl 2-methoxyimino-5-morpholin-4-yl-pent-3-ynoate in 10 ml toluene. The reaction mixture is heated for 24 hours at 130° in an autoclave. It is subsequently evaporated and the residue is chromatographed on silica gel (ethyl acetate/hexane 1:2). This gives 3 g of crystals of the title compound of melting point 64–66°.

H-9: Methyl(2-chloromethyl-4,5-dimethylcyclohexa-1,4-dienyl)methoxyiminoacetate 1.4 ml of ethyl chloroformate are added to a solution of 2.3 g methyl (4,5-dimethyl-2-morpholin-4-ylmethylcyclohexa-1,4-dienyl)methoxyiminoacetate in 25 ml of THF. The mixture is now heated for 20 hours at 70°. After the mixture has been evaporated, the residue is chromatographed on silica gel (ether/hexane 1:2). This gives 1.5 g of crystals of the title compound of melting point 65–68°.

H-10: Methyl(2-chloromethyl-4,5-dimethylcyclohexa-1,4-dienyl)methoxyiminoacetate 1.4 ml of ethyl chloroformate are added to a solution of 2.1 g of methyl[2-(2,6-dimethylmorpholin-4-ylmethyl)-4,5-dimethylcyclohexa-1,4-dienyl]methoxyiminoacetate in 25 ml of THF. The mixture is now heated for 20 hours at 70°. After the mixture has been evaporated, the residue is chromatographed on silica gel (ether/hexane 1:2). This gives 1.2 g of crystals of the title compound of melting point 65–68°.

H-11: Methyl(4,5-dimethyl-2-o-tolyloxymethylcyclohexa-1,4-dienyl)methoxyiminoacetate 20 g of o-cresol and 40 g of potassium carbonate are added to a solution of 27.5 g of methyl(2-chloromethyl-4,5-dimethylcyclohexa-1,4-dienyl)methoxyiminoacetate. The mixture is now heated for 14 hours at 65°, cooled to room temperature and filtered with suction, and the filtrate is evaporated. The residue is taken up in 150 ml of ethyl acetate, the mixture is washed with potassium carbonate solution and filtered with suction, and the filtrate is evaporated. In this manner, 34 g of the title compound are obtained as a pale brown oil.

H-12: Methyl 5-chloro-2-methoxyiminopent-3-ynoate 1.4 ml of ethyl chloroformate are added to a solution of 12.1 g of methyl 2-methoxyimino-5-morpholin-4-ylpent-3-ynoate in 25 ml of THF. The mixture is now heated for 20 hours at 70°. After evaporation, the residue is chromatographed on silica gel (ether/hexane 1:2). This gives 8.2 g of colourless crystals of the title compound of melting point 64–67°.

H-13: methyl 2-methoxyimino-5-o-tolyloxypent-3-ynoate 20 g of the sodium salt of o-cresol are added to a solution of 27.5 g of methyl 5-chloro-2-methoxyiminopent-3-ynoate in 5 ml of acetonitrile. The mixture is now heated for 14 hours at 75°, cooled to room temperature and filtered with suction, and the filtrate is evaporated. The residue is taken up in 150 ml of ethyl acetate, the mixture is washed with potassium carbonate solution and filtered with suction, and the filtrate is evaporated. This gives 32 g of the title compound as a pale brown oil.

H-14: methyl(4,5-dimethyl-2-(2',3'-dimethyl-4'-(2"-ethoxyethyl)phenyloxymethyl)cyclohexa-1,4-dienyl)methoxyiminoacetate (Comp. 6.160)

1.2 g of 2,3-dimethyl-4-(2-ethoxyethyl)phenol and 1.7 g of potassium carbonate are added to solution of 1.7 g of methyl(2-chloromethyl-4,5-dimethyl-cyclohexa-1,4-dienyl) methoxyiminoacetate in 30 ml acetonitrile and 5 ml of dimethylformamide. The mixture is now heated for 14 hours at 90°, cooled to room temperature and filtered with suction, and the filtrate is evaporated. The residue is taken up in 150 ml ethyl acetate, the mixture is washed with potassium carbonate solution and filtered with suction, and the filtrate is evaporated. After evaporation, the product is chromatographed on silica gel. This gives 0.65 g of the title compound as a pale brown oil.

H-15: Preparation of Compound 6.158

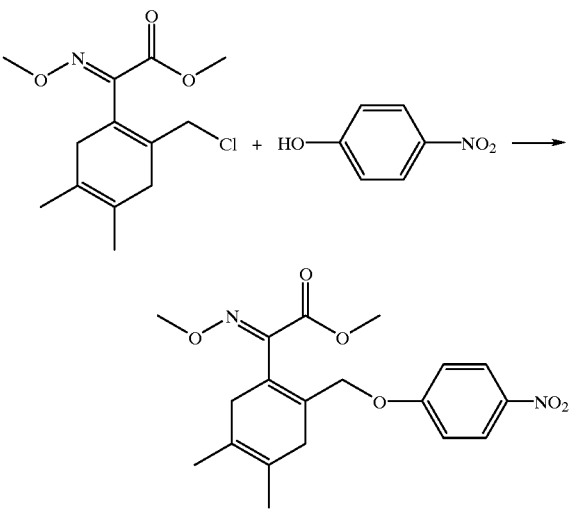

700 mg of potassium carbonate and 900 mg of 4-nitrophenol are added to a solution of 1 g of methyl(2-chloromethyl-4,5-dimethylcyclohexa-1,4-dienyl)methoxyiminoacetate. The mixture is then stirred for 4 hours at 80°, cooled and chromatographed on silica gel (ether/hexane 1:2). This gives 900 mg of crystals of the title compound of m.p. 128–130°.

H-16: Preparation of Compound 6.156

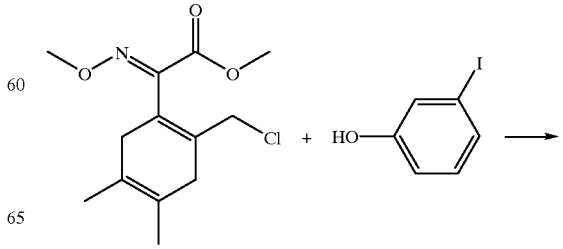

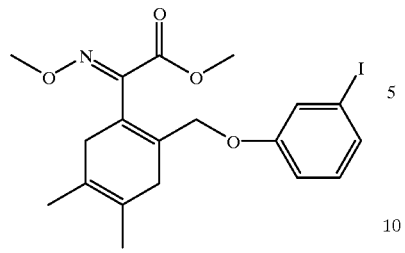

17700 mg of potassium carbonate and 22.4 g of 3-iodophenol are added to a solution of 23.1 g of methyl (2-chloromethyl-4,5-dimethylcyclohexa-1,4-dienyl) methoxyiminoacetate in 80 ml of DMSO. The mixture is then stirred for 4 hours at 80°, cooled and chromatographed on silica gel (ether/hexane 1:2). This gives 34.3 g of crystals of the title compound of m.p. 92–94°.

H-17: Preparation of Compound 6.150

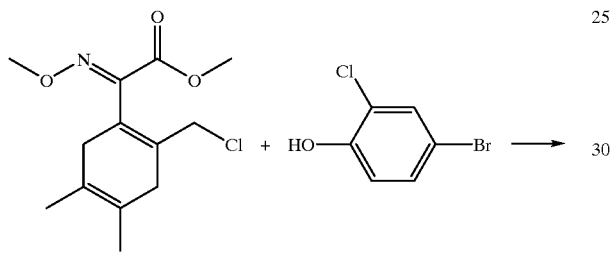

700 mg of potassium carbonate and 900 mg of 4-bromo-2-chlorophenol are added to a solution of 1 g of methyl(2-chloromethyl-4,5-dimethylcyclohexa-1,4-dienyl) methoxyiminoacetate in 3.5 ml of DMSO. The mixture is then stirred for 4 hours at 80°, cooled and chromatographed on silica gel (ether/hexane 1:2). This gives 850 mg of crystals of the title compound of m.p. 122–127°.

H-18: Preparation of Compound 28.103

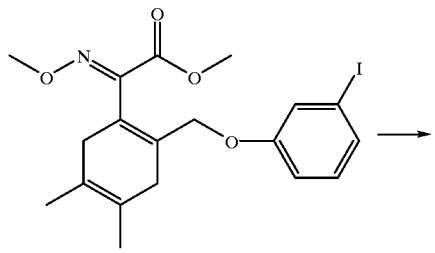

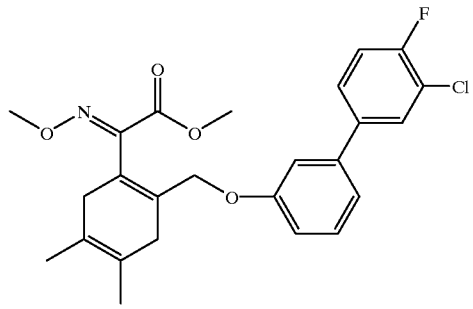

1.4 g of potassium carbonate, 0.83 g of 3-chloro-4-fluorophenylboric acid and 0.46 g of Pd(PPh)$_4$ are added to a solution of 1.9 g of compound 6.156 in 16 ml dimethoxyethane, 12 ml of tetrahydrofuran and 16 ml of water under argon. The mixture is now stirred for 5 hours at 75°. The reaction mixture is treated with 150 ml of ethyl acetate and the aqueous phase is separated off. The ethyl acetate phase is washed twice with water, dried and evaporated, and the residue is chromatographed on silica gel (ether/hexane 1:2). This gives 1.6 g of crystals of the title compound.

H-19: Preparation of Compound 22.002

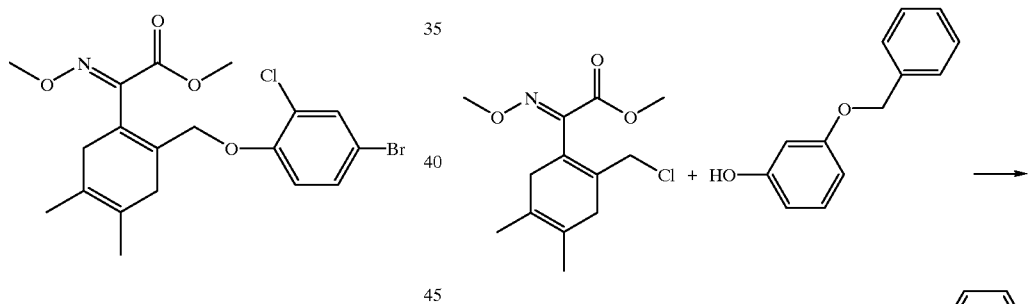

700 mg of potassium carbonate and 900 mg of 3-benzyloxyphenol are added to a solution of 1 g of methyl (2-chloromethyl-4,5-dimethylcyclohexa-1,4-dienyl) methoxyiminoacetate in 3.5 ml of DMSO. The mixture is then stirred for 4 hours at 80°, cooled and chromatographed on silica gel (ether/hexane 1:2). This gives 850 mg of crystals of the title compound.

H-20: Preparation of Compound 24.003

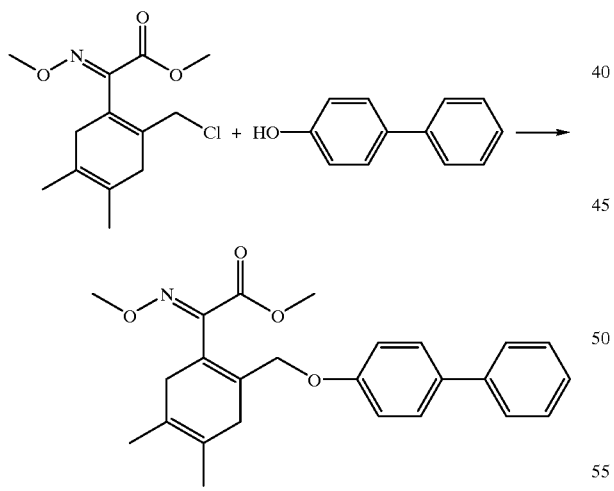

700 mg of potassium carbonate and 900 mg of 4-phenoxyphenol are added to a solution of 1 g of methyl (2-chloromethyl-4,5-dimethylcyclohexa-1,4-dienyl)methoxyiminoacetate. The mixture is then stirred for 4 hours at 80°, cooled and chromatographed on silica gel (ether/hexane 1:2). This gives 850 mg of resinous oil of the title compound.

H-21: Preparation of Compound 6.168

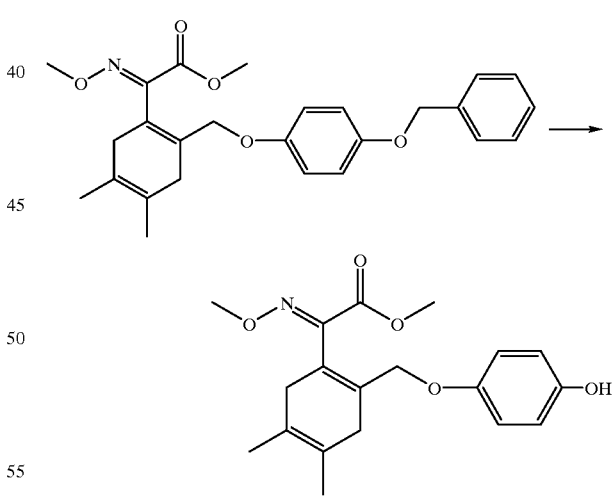

700 mg of potassium carbonate and 900 mg of 4-phenylphenol are added to a solution of 1 g of methyl(2-chloromethyl-4,5-dimethylcyclohexa-1,4-dienyl)methoxyiminoacetate. The mixture is then stirred for 4 hours at 80°, cooled and chromatographed on silica gel (ether/hexane 1:2). This gives 750 mg of resinous oil of the title compound.

H-22: Preparation of Compound 6.178

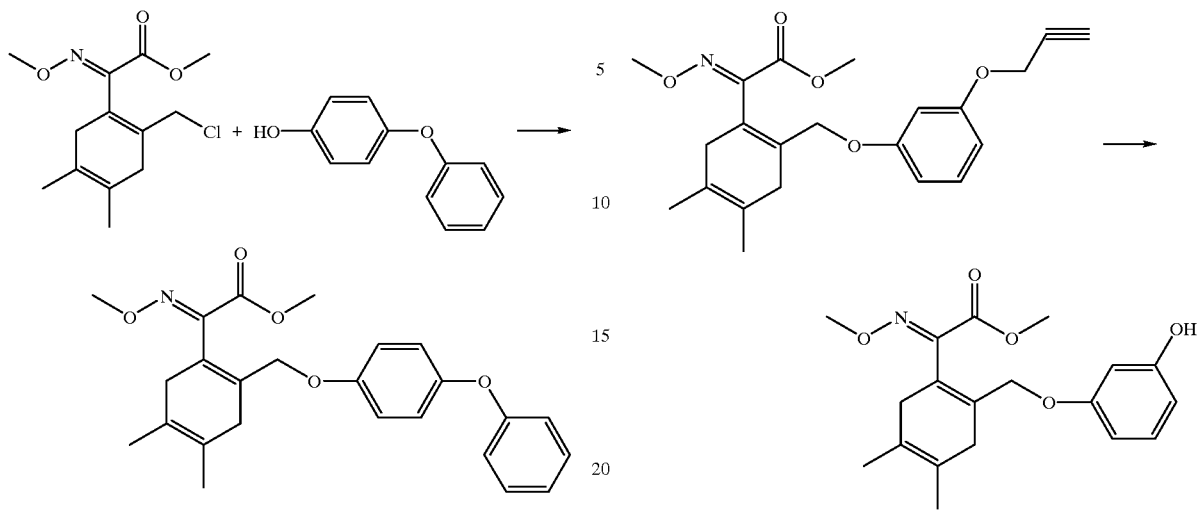

0.1 g of Pd(TPP)$_2$Cl$_2$ and 0.3 ml of triethylamine are added to a solution of 1 g starting material in 3 ml of methanol. The reaction mixture is now stirred for 6 hours at 60° and poured into 40 ml of water, and this mixture is extracted with twice 20 ml of ether/THF 4:1. After evaporation, the residue is chromatographed on silica gel (ether/hexane 3:1). This gives 0.5 g of product as resinous oil.

H-23: Preparation of Compound 6.179

0.1 g of Pd/C 10% is added to a solution of 5 g of starting material in 30 ml of tetrahydrofuran. The mixture is now hydrogenated until the theoretic amount of hydrogen has been consumed. Thereupon, the mixture is filtered with suction, the filtrate is evaporated and the residue is chromatographed on silica gel (ethyl acetate/hexane 1:2). This gives 3.5 g of product as an oil.

H-24: Preparation of Compound 23.017

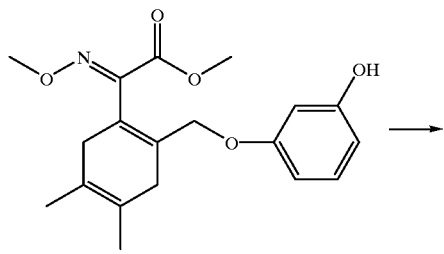

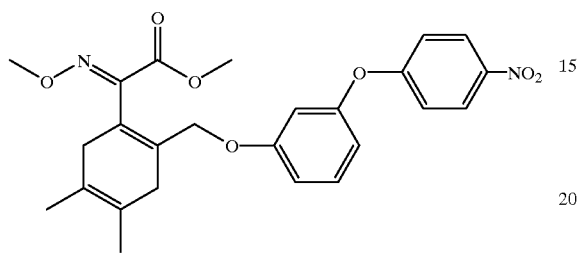

700 mg of potassium carbonate and 900 mg of 4-chloronitrobenzene are added to a solution of 1 g of Compound 6.178 in 3.5 ml of DMSO. The mixture is then stirred for 4 hours at 80°, cooled and chromatographed on silica gel (ether/hexane 1:2). This gives 700 mg of resinous oil of the title compound.

H-25: Preparation of Compound 22.005

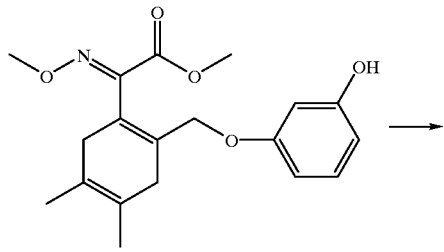

700 mg of potassium carbonate and 900 mg of 3-chloromethylbenzotrifluoride are added to a solution of 1 g of Compound 6.178 in 3.5 ml of DMSO. The mixture is then stirred for 4 hours at 80°, cooled and chromatographed on silica gel (ether/hexane 1:2). This gives 800 mg of resinous oil of the title compound.

H-26: Preparation of Compound 19.002

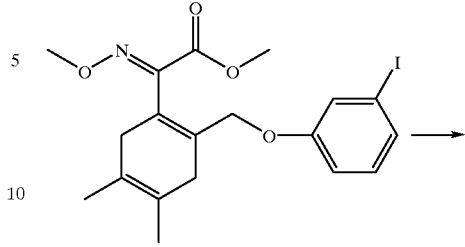

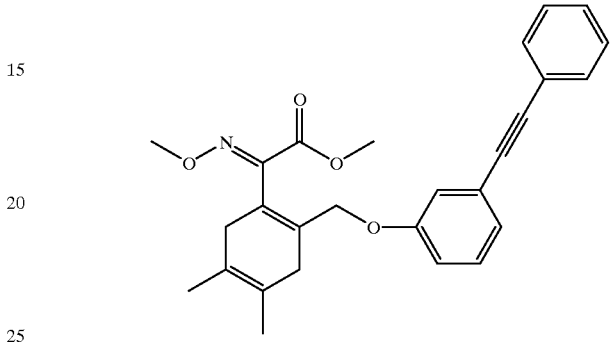

620 mg of phenylacetylene at 0.15 g of Pd(TPP)$_2$Cl$_2$ are added to a solution of 1820 mg of starting material in 1 ml of triethylamine and 7 ml of DMSO. The mixture is now stirred for 3 hours at 65° and filtered with suction, the filtrate is evaporated and the residue is chromatographed on silica gel (ether/hexane 1:2). This gives 1540 mg of product as crystals of melting point 98–101°.

H-27: Preparation of Compound 20.002

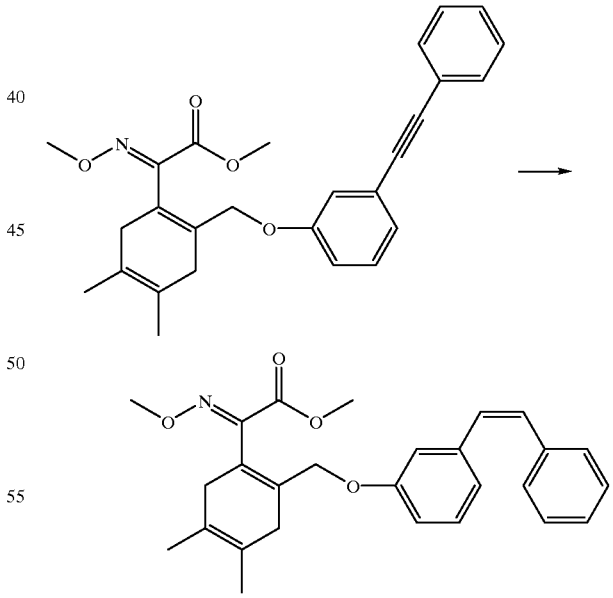

100 mg of Pd/C (5%) are added to a solution of 1.8 g of Compound 19.002 in 30 ml of tetrahydrofuran. The mixture is now hydrogenated until the theoretic amount of hydrogen has been consumed and then filtered with suction, the filtrate is evaporated and the residue is chromatographed on silica gel (ethyl acetate lhexane 1:2). This gives 1.5 g of product as an oil.

H-28: Preparation of Compound 21.002

H-29: Preparation of Compound 23.009

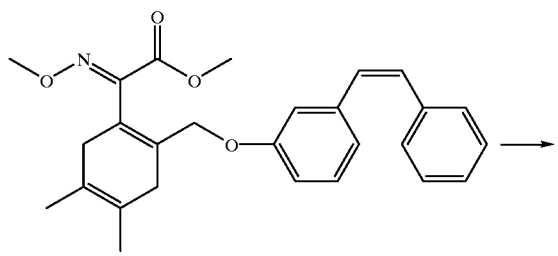

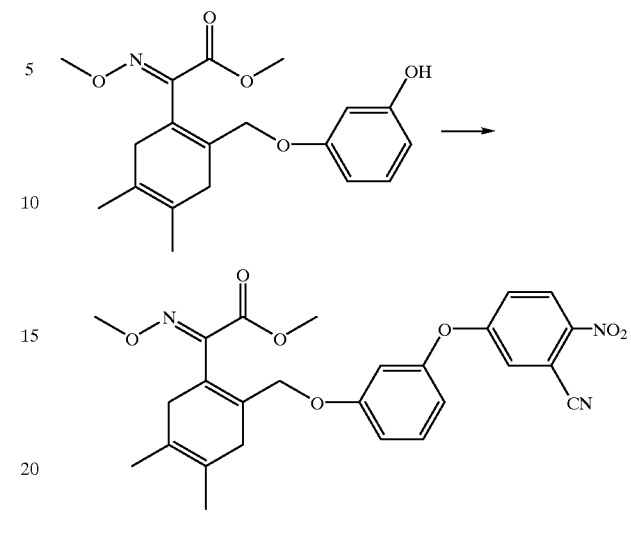

100 mg of Pd/C (5%) are added to a solution of 1.5 g of Compound 19.002 in 30 ml of tetrahydrofuran. The mixture is now hydrogenated until the theoretic amount of hydrogen has been consumed and then filtered with suction, the filtrate is evaporated and the residue is chromatographed on silica gel (ethyl acetate/hexane 1:2). This gives 1.29 of product as an oil.

700 mg of potassium carbonate and 900 mg of 2-nitro-5-fluorobenzonitrile are added to a solution of 1 g of Compound 6.178 in 3.5 ml of DMSO. The mixture is then stirred for 4 hours at 80°, cooled and chromatographed on silica gel (ether/hexane 1:2). This gives 900 mg of resinous oil of the title compound.

TABLE 1

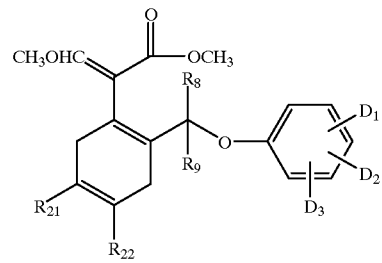

| Comp. No. | $R_{21}$ | $R_{22}$ | $R_8$ | $R_9$ | $D_1$ | $D_2$ | $D_3$ | Physical data |
|---|---|---|---|---|---|---|---|---|
| 1.1 | $CH_3$ | $CH_3$ | H | H | H | H | H | |
| 1.2 | $CH_3$ | $CH_3$ | H | H | 2-$CH_3$ | H | H | oil |
| 1.3 | $CH_3$ | $CH_3$ | H | H | 3-$CH_3$ | H | H | |
| 1.4 | $CH_3$ | $CH_3$ | H | H | 4-$CH_3$ | H | H | |
| 1.5 | $CH_3$ | $CH_3$ | H | H | 2-$CH_3$ | 3-$CH_3$ | H | |
| 1.6 | $CH_3$ | $CH_3$ | H | H | 2-$CH_3$ | 4-$CH_3$ | H | |
| 1.7 | $CH_3$ | $CH_3$ | H | H | 2-$CH_3$ | 5-$CH_3$ | H | |
| 1.8 | $CH_3$ | $CH_3$ | H | H | 2-$CH_3$ | 6-$CH_3$ | H | |
| 1.9 | $CH_3$ | $CH_3$ | H | H | 2-Et | 4-$CH_3$ | H | |
| 1.10 | $CH_3$ | $CH_3$ | H | H | 2-i-Prop | 5-$CH_3$ | H | |
| 1.11 | $CH_3$ | $CH_3$ | H | H | 2-$CH_3$ | 6-$CH_3$ | H | |
| 1.12 | $CH_3$ | $CH_3$ | H | H | 2-$CH_3$ | 6-$CH_3$ | 4-Me | |
| 1.13 | $CH_3$ | $CH_3$ | H | H | 2-$CH_3$ | 6-$CH_3$ | 4-Et | |
| 1.14 | $CH_3$ | $CH_3$ | H | H | 2-Cl | H | H | |
| 1.15 | $CH_3$ | $CH_3$ | H | H | 3-Cl | H | H | |
| 1.16 | $CH_3$ | $CH_3$ | H | H | 4-Cl | H | H | |
| 1.17 | $CH_3$ | $CH_3$ | H | H | 2-$CH_3$ | 3-Cl | H | |
| 1.18 | $CH_3$ | $CH_3$ | H | H | 2-$CH_3$ | 4-Cl | H | |
| 1.19 | $CH_3$ | $CH_3$ | H | H | H | 2-$OCH_3$ | H | |
| 1.20 | $CH_3$ | $CH_3$ | H | H | H | 3-$OCH_3$ | H | |
| 1.21 | $CH_3$ | $CH_3$ | H | H | H | 4-$OCH_3$ | H | |

TABLE 1-continued

[Structure: Cyclohexadiene with CH3OHC=C-CO-OCH3 group at one position, CR8R9-O-phenyl(D1,D2,D3) at adjacent position, and R21, R22 substituents on the ring]

| Comp. No. | R21 | R22 | R8 | R9 | D1 | D2 | D3 | Physical data |
|---|---|---|---|---|---|---|---|---|
| 1.22 | CH3 | CH3 | H | H | H | 4-OCF3 | H | |
| 1.23 | CH3 | CH3 | H | H | 2-OCH3 | 3-OCH3 | H | |
| 1.24 | CH3 | CH3 | H | H | 2-OCH3 | 4-OCH3 | H | |
| 1.25 | CH3 | CH3 | H | H | 2-OCH3 | 5-OCH3 | H | |
| 1.26 | CH3 | CH3 | H | H | 2-OCH3 | 5-OCH3 | 6-OMe | |
| 1.27 | CH3 | CH3 | H | H | 2-OCH3 | 5-OCH3 | 4-OMe | |
| 1.28 | CH3 | CH3 | H | H | H | 2-CF3 | H | |
| 1.29 | CH3 | CH3 | H | H | H | 3-CF3 | H | |
| 1.30 | CH3 | CH3 | H | H | H | 4-CF3 | H | |
| 1.31 | CH3 | CH3 | H | H | 2-CH3 | 4-OCF3 | H | |
| 1.32 | H3 | CH3 | H | H | 2-Et | 3-CF3 | H | |
| 1.33 | CH3 | CH3 | H | H | 2-Prop | 4-CF3 | H | |
| 1.34 | CH3 | CH3 | H | H | 2-Prop | 4-CF3 | 6-Me | |
| 1.35 | CH3 | CH3 | H | H | H | 3-OCF3 | H | |
| 1.36 | CH3 | CH3 | H | H | H | 5-OCF3 | H | |
| 1.37 | CH3 | CH3 | H | H | H | 5-OCF3 | 2-Me | |
| 1.38 | CH3 | CH3 | H | H | H | 5-OCF3 | 4-Me | |
| 1.39 | CH3 | CH3 | H | H | 2-CH3 | 4-propynyl | H | |
| 1.40 | CH3 | CH3 | H | H | 2-CH3 | 4-allyl | H | |
| 1.41 | CH3 | CH3 | H | H | 3-CH3 | 6-propargyl | H | |
| 1.42 | CH3 | CH3 | H | H | 2-OCH3 | 4-allyl | H | |
| 1.43 | CH3 | CH3 | H | H | 2-OCH3 | 4-propargyl | H | |
| 1.44 | CH3 | CH3 | H | H | 2-CH3 | 4-O-allyl | H | |
| 1.45 | CH3 | CH3 | H | H | 2-CH3 | 4-O-propargyl | H | |
| 1.46 | CH3 | CH3 | H | H | 2-OCH3 | 4-O-allyl | H | |
| 1.47 | CH3 | CH3 | H | H | 2-OCH3 | 4-O-propargyl | H | |
| 1.48 | CH3 | CH3 | H | H | 2-OCH3 | 4-ethynyl | H | |
| 1.49 | CH3 | CH3 | H | H | 2-OCH3 | 4-ethynyl | 6-Me | |
| 1.50 | CH3 | CH3 | H | H | 2-O-allyl | 4-O-allyl | H | |
| 1.51 | CH3 | CH3 | H | H | 2-O-allyl | 6-O-propargyl | H | |
| 1.52 | CH3 | CH3 | H | H | 2-Cl | 4-O-allyl | H | |
| 1.53 | CH3 | CH3 | H | H | 2-Br | 4-O-propargyl | H | |
| 1.54 | CH3 | CH3 | H | H | 2-CF3 | 4-ethynyl | H | |
| 1.55 | CH3 | CH3 | H | H | 2-CF3 | 4-ethynyl | 6-Me | |
| 1.56 | CH3 | CH3 | H | H | H | 2-benzyl | H | |
| 1.57 | CH3 | CH3 | H | H | H | 2-benzyloxy | H | |
| 1.58 | CH3 | CH3 | H | H | 2-CH3 | 3-phenoxy | H | |
| 1.59 | CH3 | CH3 | H | H | 2-CH3 | 3-phenoxy(4-Cl) | H | |
| 1.60 | CH3 | CH3 | H | H | 2-OCH3 | 4-benzyloxy | H | |
| 1.61 | CH3 | CH3 | H | H | 3-OCH3 | 5-benzyloxy(3-CF3) | H | |
| 1.62 | CH3 | CH3 | H | H | 3-OCH3 | 6-benzyloxy(3-OCF3) | H | |
| 1.63 | CH3 | CH3 | H | H | H | 4-cyclopropyl-methyloxy | H | |
| 1.64 | CH3 | CH3 | H | H | 3-OCH3 | 5-cyclopropyl-methyloxy | H | |
| 1.65 | CH3 | CH3 | H | H | 3-OCH3 | 5-(dichloro-cyclopropyl)-methoxy | H | |
| 1.66 | CH3 | CH3 | H | H | H | 3-C(CH3)=NOCH3 | H | |
| 1.67 | CH3 | CH3 | H | H | H | 4-C(CH3)(=NOCH3)C(=O)- | H | |

TABLE 1-continued

[Structure diagram: a cyclohexadiene ring with a methoxyiminoacetate group (CH₃OHC=... with OCH₃ ester) and a CH(R₈)(R₉) group bearing an O-phenyl ether (with D₁, D₂, D₃ substituents), and R₂₁, R₂₂ on the ring.]

| Comp. No. | R₂₁ | R₂₂ | R₈ | R₉ | D₁ | D₂ | D₃ | Physical data |
|---|---|---|---|---|---|---|---|---|
| 1.68 | CH₃ | CH₃ | H | H | H | 4- CH₃–C(=NOCH₃)–C(=NOCH₃)– | H | |
| 1.69 | CH₃ | CH₃ | H | H | H | 3- CH₃–C(=NOCH₃)– | H | |
| 1.70 | CH₃ | CH₃ | H | H | H | 3- C₆H₅–C(=NOCH₃)– | H | |
| 1.71 | CH₃ | CH₃ | H | H | H | C₆H₅-4-Cl –C(=NOCH₃)– | H | |
| 1.72 | CH₃ | CH₃ | H | H | H | 4- C₆H₄-4-phenoxy –C(=NOCH₃)– | H | |
| 1.73 | CH₃ | CH₃ | H | H | H | 4- C₆H₄-4-(4-chlorophenoxy) –C(=NOCH₃)– | H | |
| 1.74 | CH₃ | CH₃ | H | H | H | 4- C₆H₄-4-(4-chlorophenoxy) –C(=NOC₂H₅)– | H | |
| 1.75 | H | CH₃ | H | H | 3-CH₃ | H | H | |
| 1.76 | H | CH₃ | H | H | 4-CH₃ | H | H | |
| 1.77 | H | CH₃ | H | H | 2-CH₃ | 3-CH₃ | H | |
| 1.78 | H | CH₃ | H | H | 2-CH₃ | 4-CH₃ | H | |
| 1.79 | CH₃ | H | H | H | 2-CH₃ | 5-CH₃ | H | |
| 1.80 | CH₃ | H | H | H | 2-CH₃ | 6-CH₃ | H | |
| 1.81 | CH₃ | H | H | H | 2-Et | 4-CH₃ | H | |
| 1.82 | CH₃ | H | H | H | 2-i-Prop | 5-CH₃ | H | |
| 1.83 | CH₃ | H | H | H | 2-i-Prop | 5-CH₃ | 4-Me | |
| 1.84 | H | Cl | H | H | 2-CH₃ | 6-CH₃ | H | |
| 1.85 | H | Cl | H | H | 2-Cl | H | H | |
| 1.86 | H | Cl | H | H | 3-Cl | H | H | |
| 1.87 | H | Cl | H | H | 4-Cl | H | H | |
| 1.88 | H | Cl | H | H | 4-Cl | H | 4-Me | |
| 1.89 | OCH₃ | H | H | H | 2-CH₃ | 3-Cl | H | |
| 1.90 | OCH₃ | H | H | H | 2-CH₃ | 4-Cl | H | |
| 1.91 | OCH₃ | H | H | H | H | 2-OCH₃ | H | |

TABLE 1-continued

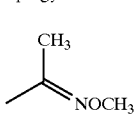

| Comp. No. | $R_{21}$ | $R_{22}$ | $R_8$ | $R_9$ | $D_1$ | $D_2$ | $D_3$ | Physical data |
|---|---|---|---|---|---|---|---|---|
| 1.92 | OCH$_3$ | CH$_3$ | H | H | H | 3-OCH$_3$ | H | |
| 1.93 | OCH$_3$ | CH$_3$ | H | H | H | 4-OCH$_3$ | H | |
| 1.94 | OCH$_3$ | CH$_3$ | H | H | H | 5-OCH$_3$ | H | |
| 1.95 | OCH$_3$ | CH$_3$ | H | H | H | 5-OCH$_3$ | 4-OMe | |
| 1.96 | CH$_3$ | CH$_3$ | CH$_3$ | H | 2-OCH$_3$ | 3-OCH$_3$ | H | |
| 1.97 | CH$_3$ | CH$_3$ | CH$_3$ | H | 2-OCH$_3$ | 4-OCH$_3$ | H | |
| 1.98 | CH$_3$ | CH$_3$ | CH$_3$ | CH$_3$ | 2-OCH$_3$ | 5-OCH$_3$ | H | |
| 1.99 | CH$_3$ | CH$_3$ | CH$_3$ | CH$_3$ | H | 2-CF$_3$ | H | |
| 1.100 | Cl | CH$_3$ | CH$_3$ | CH$_3$ | H | 3-CF$_3$ | H | |
| 1.101 | CH$_3$ | CH$_3$ | Prop | H | H | 4-CF$_3$ | H | |
| 1.102 | CH$_3$ | CH$_3$ | Prop | H | 2-CH$_3$ | 4-OCF$_3$ | H | |
| 1.103 | H | H | Prop | H | 2-CH$_3$ | 4-OCF$_3$ | H | |
| 1.104 | H | H | H | H | 2-Et | 3-CF$_3$ | H | |
| 1.105 | H | H | H | H | 2-Prop | 4-CF$_3$ | H | |
| 1.106 | H | H | H | H | H | 4-OCF$_3$ | H | |
| 1.107 | H | H | H | H | H | 3-OCF$_3$ | H | |
| 1.108 | H | H | H | H | H | 5-OCF$_3$ | H | |
| 1.109 | H | H | H | H | H | 4-ethynyl | H | |
| 1.110 | Cl | CH$_3$ | H | H | 2-CH$_3$ | 4-propynyl | H | |
| 1.111 | Cl | CH$_3$ | H | H | 2-CH$_3$ | 4-allyl | H | |
| 1.112 | Cl | CH$_3$ | H | H | 3-CH$_3$ | 6-propargyl | H | |
| 1.113 | CH$_3$ | Cl | H | H | 2-OCH$_3$ | 4-allyl | H | |
| 1.114 | CH$_3$ | Cl | H | H | 2-OCH$_3$ | 4-propargyl | H | |
| 1.115 | CH$_3$ | Cl | H | H | 3-OCH$_3$ | 4-propargyl | H | |
| 1.116 | CH$_3$ | CH$_3$ | H | H | H | 3- 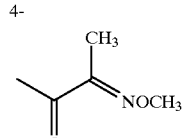 | H | |
| 1.117 | H | H | H | H | H | 4- 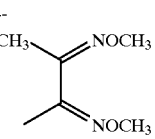 | H | |
| 1.118 | H | H | H | H | H | 4- 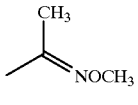 | H | |
| 1.119 | CH$_3$ | H | H | H | H | 3- 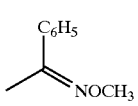 | H | |
| 1.120 | Cl | CH$_3$ | H | H | H | 3- $C_6H_5$ 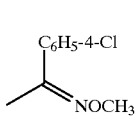 | H | |
| 1.121 | Cl | CH$_3$ | H | H | H | 4- $C_6H_5$-4-Cl | H | |

TABLE 1-continued

| Comp. No. | R$_{21}$ | R$_{22}$ | R$_8$ | R$_9$ | D$_1$ | D$_2$ | D$_3$ | Physical data |
|---|---|---|---|---|---|---|---|---|
| 1.122 | CH$_3$ | Cl | H | H | H | 4-C$_6$H$_4$-4-phenoxy-C(=NOCH$_3$)- | H | |
| 1.123 | CH$_3$ | Cl | H | H | H | 4-C$_6$H$_4$-4-(4-chlorophenoxy)-C(=NOCH$_3$)- | H | |
| 1.124 | Me | Me | H | H | H | 4-C$_6$H$_4$-4-OCH$_2$—C$_6$H$_4$-3-CF$_3$, C(=N-O-ethyl)- | H | |
| 1.125 | Me | Me | H | H | H | 4-C$_6$H$_4$-4-OCH$_2$—C$_6$H$_4$-4-CF$_3$, C(=N-O-ethyl)- | H | |
| 1.126 | Me | Me | H | H | H | 4-C$_6$H$_4$-4-OCH$_2$—C$_6$H$_4$-2-CF$_3$, C(=N-O-ethyl)- | H | |
| 1.127 | Me | Me | H | H | 2-CH=CH$_2$ | 3-CH=CH— | H | |
| 1.128 | Me | Me | H | H | 2-Me | 3-CH$_2$—CH=CH$_2$ | 4-OMe | |
| 1.129 | Me | Me | H | H | 2-Me | 3-CH$_2$—CH=CH$_2$ | 4-OEt | |
| 1.130 | Me | Me | H | H | 2-Me | 4-OCH$_2$—C$_6$H$_5$ | 3-CH$_2$—CH=CH$_2$ | |
| 1.131 | Me | Me | H | H | 2-Me | 4-OCH$_2$—C$_6$H$_4$(4-CN) | 3-CH$_2$—CH=CH$_2$ | |
| 1.132 | H | H | H | H | 2-Me | 3-CH$_2$—CH=CH$_2$ | 4-OMe | |
| 1.133 | H | H | H | H | 2-Me | 3-CH$_2$—CH=CH$_2$ | 4-OEt | |
| 1.134 | H | H | H | H | 2-Me | 4-OCH$_2$—C$_6$H$_5$ | 3-CH$_2$—CH=CH$_2$ | |
| 1.135 | H | H | H | H | 2-Me | 4-OCH$_2$—C$_6$H$_4$(4-CN) | 3-CH$_2$—CH=CH$_2$ | |
| 1.136 | H | H | H | H | 3-Me | 4-ethynyl | 2-Me | |
| 1.137 | H | H | H | H | 3-Me | 4-OCH$_2$—CH$_2$—OH | 2-Me | |
| 1.138 | H | H | H | H | 3-Me | 4-OCH$_2$—CH$_2$—OCOCH$_3$ | 2-Me | |
| 1.139 | H | H | H | H | 3-Me | 4-OCH$_2$—CH$_2$—OCO(CH$_3$)$_6$—CH=CF$_2$ | 2-Me | |
| 1.140 | H | Me | H | H | H | 2-Me | H | |
| 1.141 | Me | Me | H | H | H | 4-C(Me)$_2$—C$_6$H$_4$-4'-OCH$_2$—C≡C—C$_6$H$_3$(Cl$_2$)(2",4") | H | |
| 1.142 | Me | Me | H | H | H | —O—(CH$_2$)$_3$—C$_6$H$_5$ | H | |

TABLE 1-continued

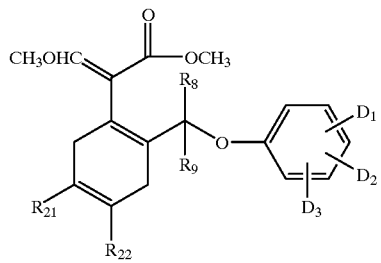

| Comp. No. | $R_{21}$ | $R_{22}$ | $R_8$ | $R_9$ | $D_1$ | $D_2$ | $D_3$ | Physical data |
|---|---|---|---|---|---|---|---|---|
| 1.143 | Me | Me | H | H | H | 2-Me | H | |
| 1.144 | Me | Me | H | H | H | —(C=NOEt)C$_5$H$_4$(F)(4') | H | |
| 1.145 | Me | Me | H | H | H | —(C=NOEt)C$_5$H$_4$(Br)(4') | H | |
| 1.146 | Me | Me | H | H | H | —(C=NOEt)C$_6$H$_4$—(C≡C—C$_6$H$_5$)(4') | H | |
| 1.147 | Me | Me | H | H | H | —(C=NOEt)C$_6$H$_4$—(CH$_2$—CH$_2$—C$_6$H$_5$)(4') | H | |
| 1.148 | Me | Me | H | H | H | 3-O—propargy | H | |
| 1.149 | Me | Me | H | H | 2-Br | 4-Cl | H | |
| 1.150 | Me | Me | H | H | 4-Br | 2-Cl | H | |
| 1.151 | Me | Me | H | H | H | 4-COEt | H | |
| 1.152 | Me | Me | H | H | H | 4-COMe | H | |
| 1.153 | Me | Me | H | H | H | 3-CH$_2$—(3'-methyl-isoxazolyl(5')) | H | |
| 1.154 | Me | Me | H | H | H | 3-CH$_2$—(3'-ethyl-isoxazolyl(5')) | H | |
| 1.155 | Me | Me | H | H | H | 4-I | H | |
| 1.156 | Me | Me | H | H | H | 3-I | H | |
| 1.157 | Me | Me | H | H | H | 4-C$_9$H$_{19}$ | H | |
| 1.158 | Me | Me | H | H | H | 4-NO$_2$ | H | |
| 1.159 | Me | Me | H | H | H | 4-Br | H | |
| 1.160 | Me | Me | H | H | H | 4-F | H | |
| 1.161 | Me | Me | H | H | H | 4-C$_{12}$H$_{25}$ | H | |
| 1.162 | Me | Me | H | H | H | 4-OCH$_2$CH$_2$O—CO(CH$_2$)$_3$—CH=C(F$_2$) | H | |
| 1.163 | Me | Me | H | H | H | 4-naphthyl(1') | H | |
| 1.164 | Me | Me | H | H | H | 4-naphthyl(2') | H | |
| 1.165 | Me | Me | H | H | 2-Cl | 4-C$_6$H$_5$ | H | |
| 1.166 | Me | Me | H | H | H | 4-S(O)C$_6$H$_5$ | H | |
| 1.167 | Me | Me | H | H | H | 4-(2'-pyridyl(F)(3')(Cl)(5')) | H | |
| 1.168 | Me | Me | H | H | H | 4-C$_6$H$_5$ | H | |
| 1.169 | Me | Me | H | H | H | 3-O-allyl | H | |
| 1.170 | Me | Me | H | H | H | 3-C≡CH | H | |
| 1.171 | Me | Me | H | H | H | 4-CO—C$_6$H$_4$(4')-C$_6$H$_4$(Cl)(4") | H | |
| 1.172 | Me | Me | H | H | H | 4-i-prop | H | |
| 1.173 | Me | Me | H | H | 2-F | 4-F | H | |
| 1.174 | Me | Me | H | H | H | 3-F | H | |
| 1.175 | Me | Me | H | H | H | 2-F | H | |
| 1.176 | Me | Me | H | H | H | 4-O-propargyl | H | |
| 1.177 | Me | Me | H | H | H | 4-NH$_2$ | H | |
| 1.178 | Me | Me | H | H | H | 3-OH | H | |
| 1.179 | Me | Me | H | H | H | 4-OH | H | |
| 1.180 | Me | Me | H | H | H | 2-CH$_3$ | H | |

TABLE 2

Compounds of the formula

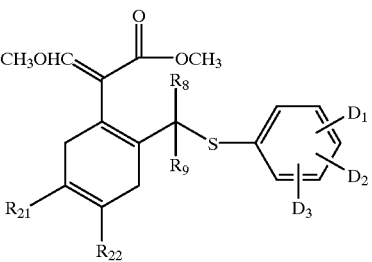

in which $R_{21}$, $R_{22}$, $R_8$, $R_9$, $D_1$, $D_2$ and $D_3$ have the meanings of the corresponding compounds of Table 1.

Physical data of exemplary compounds:

| Comp. No. | $R_{21}$ | $R_{22}$ | $R_8$ | $R_9$ | $D_1$ | $D_2$ | $D_3$ | Physical data |
|---|---|---|---|---|---|---|---|---|
| 2.02 | $CH_3$ | $CH_3$ | H | H | 2-$CH_3$ | H | H | oil |

TABLE 3

Compounds of the formula

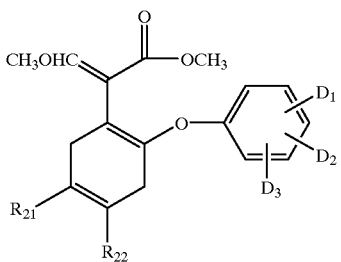

in which $R_{21}$, $R_{22}$, $D_1$, $D_2$ and $D_3$ have the meanings of the corresponding compounds of Table 1.

Physical data of exemplary compounds:

| Comp. No. | $R_{21}$ | $R_{22}$ | $R_8$ | $R_9$ | $D_1$ | $D_2$ | $D_3$ | Physical data |
|---|---|---|---|---|---|---|---|---|
| 3.02 | $CH_3$ | $CH_3$ | H | H | 2-$CH_3$ | H | H | 96–98° |

TABLE 4

Compounds of the formula

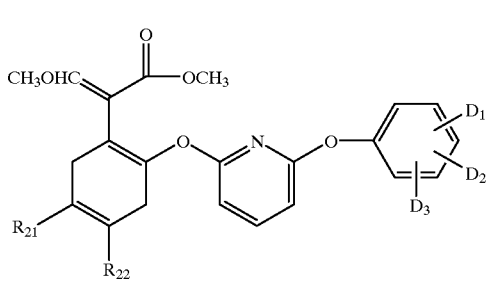

in which $R_{21}$, $R_{22}$, $D_1$, $D_2$ and $D_3$ have the meanings of the corresponding compounds of Table 1.

TABLE 5

Compounds of the formula

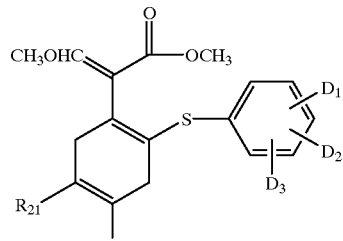

in which $R_{21}$, $R_{22}$, $D_1$, $D_2$ and $D_3$ have the meanings of the corresponding compounds of Table 1.

TABLE 6

Compounds of the formula

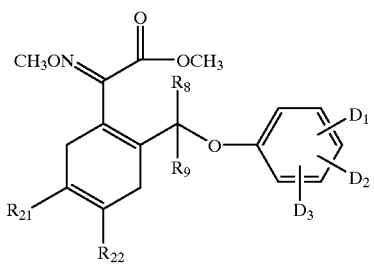

in which $R_{21}$, $R_{22}$, $R_8$, $R_9$, $D_1$, $D_2$ and $D_3$ have the meanings of the corresponding compounds of Table 1.

Physical data of exemplary compounds:

| Comp. No. | $R_{21}$ | $R_{22}$ | $R_8$ | $R_9$ | $D_1$ | $D_2$ | $D_3$ | Physical data |
|---|---|---|---|---|---|---|---|---|
| 6.1 | $CH_3$ | $CH_3$ | H | H | H | H | H | oil |
| 6.10 | $CH_3$ | $CH_3$ | H | H | 2-i-prop | 5-$CH_3$ | H | oil |
| 6.14 | $CH_3$ | $CH_3$ | H | H | 2-Cl | H | H | oil |
| 6.16 | $CH_3$ | $CH_3$ | H | H | 4-Cl | H | H | oil |
| 6.18 | $CH_3$ | $CH_3$ | H | H | 2-$CH_3$ | 4-Cl | H | oil |
| 6.140. | H | Me | H | H | H | 2-Me | H | resin |
| 6.141. | Me | Me | H | H | H | 4-C(Me)$_2$—C$_6$H$_4$-4'-OCH$_2$—C≡C—C$_6$H$_3$(Cl$_2$)(2",4") | H | resin |
| 6.142. | Me | Me | H | H | H | —O—(CH$_2$)$_3$—C$_6$H$_5$ | H | oil |
| 6.143. | Me | Me | H | H | H | 2-Me | H | oil |
| 6.144. | Me | Me | H | H | H | —(C=NOEt)C$_6$H$_4$(F)(4') | H | oil |
| 6.145. | Me | Me | H | H | H | —(C=NOEt)C$_6$H$_4$(Br)(4') | H | resin |
| 6.146. | Me | Me | H | H | H | —(C=NOEt)C$_6$H$_4$—(C≡C—C$_6$H$_5$)(4') | H | resin |
| 6.147. | Me | Me | H | H | H | —(C=NOEt)C$_6$H$_4$—(CH$_2$—CH$_2$—C$_6$H$_5$)(4') | H | oil |
| 6.148. | Me | Me | H | H | H | 3-O-propargyl | H | resin |
| 6.149. | Me | Me | H | H | 2-Br | 4-Cl | H | 113–118 |
| 6.150. | Me | Me | H | H | 4-Br | 2-Cl | H | 122–127 |
| 6.151. | Me | Me | H | H | H | 4-COEt | H | 93–96 |
| 6.152. | Me | Me | H | H | H | 4-COMe | H | 133–135 |
| 6.153. | Me | Me | H | H | H | 3-CH$_2$-(3'-methyl-isoxazolyl(5')) | H | oil |
| 6.154. | Me | Me | H | H | H | 3-CH$_2$-(3'-ethyl-isoxazolyl(5')) | H | oil |
| 6.155. | Me | Me | H | H | H | 4-I | H | 100–102 |
| 6.156. | Me | Me | H | H | H | 3-I | H | 92–94 |
| 6.157. | Me | Me | H | H | H | 4-C$_9$H$_{19}$ | H | oil |
| 6.158. | Me | Me | H | H | H | 4-NO$_2$ | H | 128–130 |
| 6.159. | Me | Me | H | H | H | 4-Br | H | oil |
| 6.160. | Me | Me | H | H | H | 4-F | H | oil |
| 6.161. | Me | Me | H | H | H | 4-C$_{12}$H$_{25}$ | H | oil |
| 6.162. | Me | Me | H | H | H | 4-OCH$_2$CH$_2$O—CO(CH$_2$)$_3$—CH=C(F$_2$) | H | oil |
| 6.163. | Me | Me | H | H | H | 4-naphthyl(1') | H | oil |
| 6.164. | Me | Me | H | H | H | 4-naphthyl(2') | H | oil |
| 6.165. | Me | Me | H | H | 2-Cl | 4-C$_6$H$_5$ | H | oil |
| 6.166. | Me | Me | H | H | H | 4-S(O)C$_6$H$_5$ | H | oil |
| 6.167. | Me | Me | H | H | H | 4-(2'-pyridyl(F)(3')(Cl)(5') | H | oil |
| 6.168. | Me | Me | H | H | H | 4-C$_6$H$_5$ | H | oil |
| 6.169. | Me | Me | H | H | H | 3-O-allyl | H | oil |
| 6.170. | Me | Me | H | H | H | 3-C≡CH | H | oil |
| 6.171. | Me | Me | H | H | H | 4-CO—C$_6$H$_4$(4')-C$_6$H$_4$(Cl)(4") | H | oil |
| 6.172. | Me | Me | H | H | H | 4-i-Prop | H | oil |
| 6.173. | Me | Me | H | H | 2-F | 4-F | H | oil |
| 6.174. | Me | Me | H | H | H | 3-F | H | oil |
| 6.175. | Me | Me | H | H | H | 2-F | H | oil |
| 6.176. | Me | Me | H | H | H | 4-O-propargyl | H | oil |
| 6.177. | Me | Me | H | H | H | 4-NH$_2$ | H |  |
| 6.178. | Me | Me | H | H | H | 3-OH | H |  |
| 6.179. | Me | Me | H | H | H | 4-OH | H | oil |
| 6.180. | Me | Me | H | H | H | 2-CH$_3$ | H |  |

TABLE 7

Compounds of the formula

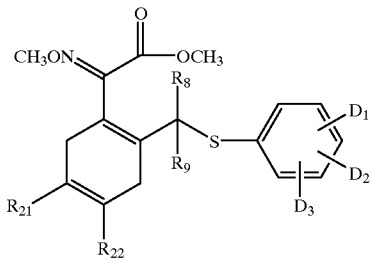

in which $R_{21}$, $R_{22}$, $R_8$, $R_9$, $D_1$, $D_2$ and $D_3$ have the meanings of the corresponding compounds of Table 1.
Physical data of exemplary compounds:

| Comp. No. | $R_{21}$ | $R_{22}$ | $R_8$ | $R_9$ | $D_1$ | $D_2$ | $D_3$ | Physical data |
|---|---|---|---|---|---|---|---|---|
| 7.1 | $CH_3$ | $CH_3$ | H | H | H | H | H | oil |
| 7.16 | $CH_3$ | $CH_3$ | H | H | 4-Cl | H | H | oil |

TABLE 8

Compounds of the formula

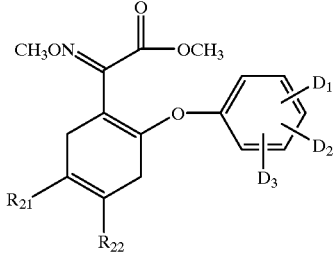

in which $R_{21}$, $R_{22}$, $D_1$, $D_2$ and $D_3$ have the meanings of the corresponding compounds of Table 1.

TABLE 9

Compounds of the formula

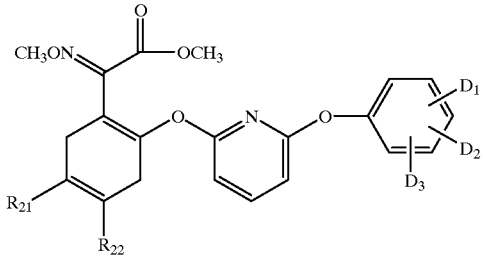

in which $R_{21}$, $R_{22}$, $D_1$, $D_2$ and $D_3$ have the meanings of the corresponding compounds of Table 1.

TABLE 10

Compounds of the formula

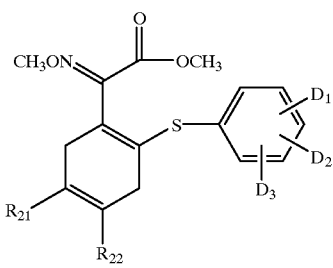

in which $R_{21}$, $R_{22}$, $D_1$, $D_2$ and $D_3$ have the meanings of the corresponding compounds of Table 1.

TABLE 11

Compounds of the formula

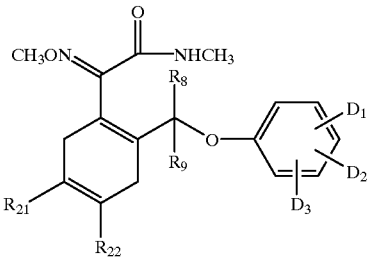

in which $R_{21}$, $R_{22}$, $R_8$, $R_9$, $D_1$, $D_2$ and $D_3$ have the meanings of the corresponding compounds of Table 1.
Physical data of exemplary compounds:

| Comp. No. | $R_{21}$ | $R_{22}$ | $R_8$ | $R_9$ | $D_1$ | $D_2$ | $D_3$ | Physical data |
|---|---|---|---|---|---|---|---|---|
| 11.140 | H | $CH_3$ | H | H | H | 2-$CH_3$ | H | oil |

TABLE 12

Compounds of the formula

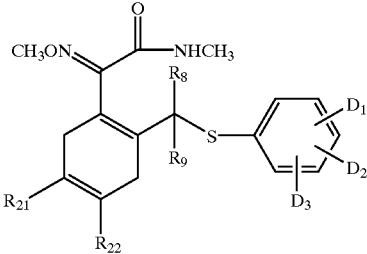

in which $R_{21}$, $R_{22}$, $R_8$, $R_9$, $D_1$, $D_2$ and $D_3$ have the meanings of the corresponding compounds of Table 1.

TABLE 13

Compounds of the formula

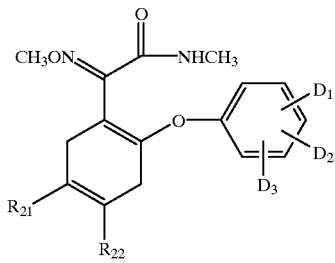

in which $R_{21}$, $R_{22}$, $D_1$, $D_2$ and $D_3$ have the meanings of the corresponding compounds of Table 1.

TABLE 14

Compounds of the formula

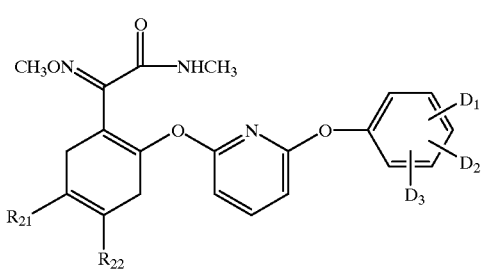

in which $R_{21}$, $R_{22}$, $D_1$, $D_2$ and $D_3$ have the meanings of the corresponding compounds of Table 1.

TABLE 15

Compounds of the formula

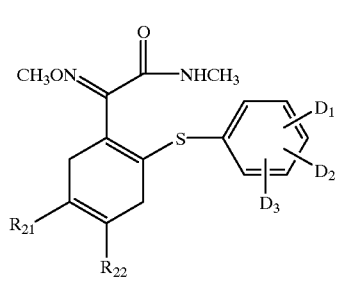

in which $R_{21}$, $R_{22}$, $D_1$, $D_2$ and $D_3$ have the meanings of the corresponding compounds of Table 1.

TABLE 16

(intermediates)

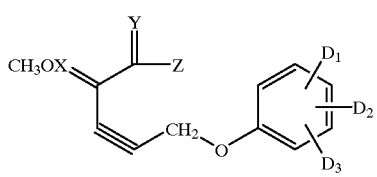

| Comp. No. | X | Y | Z | $D_1$ | $D_2$ | $D_3$ | Physical data |
|---|---|---|---|---|---|---|---|
| 16.1. | CH | O | $OCH_3$ | H | H | H | |
| 16.2. | CH | O | $OCH_3$ | 2-$CH_3$ | H | H | |
| 16.3. | CH | O | $OCH_3$ | 3-$CH_3$ | H | H | |
| 16.4. | N | O | $OCH_3$ | 2-$CH_3$ | H | H | resin |
| 16.5. | N | O | $OCH_3$ | 2-$CH_3$ | 3-$CH_3$ | H | |
| 16.6. | N | O | $OCH_3$ | 2-$CH_3$ | 4-$CH_3$ | H | |
| 16.7. | CH | O | $OCH_3$ | 2-$CH_3$ | 5-$CH_3$ | H | |
| 16.8. | N | O | $NHCH_3$ | 2-$CH_3$ | 6-$CH_3$ | H | |
| 16.9. | N | S | $NHCH_3$ | 2-Et | 4-$CH_3$ | H | |
| 16.10. | N | S | $NHCH_3$ | 2-i-Prop | 5-$CH_3$ | H | |
| 16.11. | N | S | $SCH_3$ | 2-$CH_3$ | 6-$CH_3$ | H | |
| 16.12. | N | SO | $SCH_3$ | 2-$CH_3$ | 6-$CH_3$ | 4-Me | |
| 16.13. | N | SO | $SCH_3$ | 2-$CH_3$ | 6-$CH_3$ | 4-Et | |
| 16.14. | CH | O | $SCH_3$ | 2-Cl | H | H | |
| 16.15. | CH | O | $SCH_3$ | 3-Cl | H | H | |

TABLE 16-continued (intermediates)

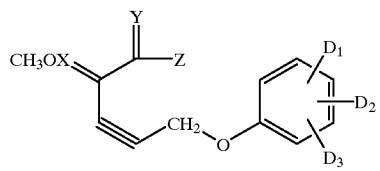

| Comp. No. | X | Y | Z | D₁ | D₂ | D₃ | Physical data |
|---|---|---|---|---|---|---|---|
| 16.16. | N | O | OCH₃ | 4-Cl | H | H | |
| 16.17. | N | O | NHCH₃ | 2-CH₃ | 3-Cl | H | |
| 16.18. | N | O | NHCH₃ | 2-CH₃ | 4-Cl | H | |
| 16.19. | N | S | NHCH₃ | H | 2-OCH₃ | H | |
| 16.20. | N | O | NHCH₃ | H | 3-OCH₃ | H | |
| 16.21. | N | S | SCH₃ | H | 4-OCH₃ | H | |
| 16.22. | N | S | SCH₃ | H | 4-OCF₃ | H | |
| 16.23. | N | O | OCH₃ | 2-OCH₃ | 3-OCH₃ | H | |
| 16.24. | CH | O | OCH₃ | 2-OCH₃ | 4-OCH₃ | H | |
| 16.25. | CH | O | OCH₃ | 2-OCH₃ | 5-OCH₃ | H | |
| 16.26. | CH | O | OCH₃ | 2-OCH₃ | 5-OCH₃ | 6-OMe | |
| 16.27. | N | O | OCH₃ | 2-OCH₃ | 5-OCH₃ | 4-OMe | |
| 16.28. | N | O | OCH₃ | H | 2-CF₃ | H | |
| 16.29. | N | O | OCH₃ | H | 3-CF₃ | H | |
| 16.30. | CH | O | OCH₃ | H | 4-CF₃ | H | |
| 16.31. | N | O | NHCH₃ | 2-CH₃ | 4-OCF₃ | H | |
| 16.32. | N | S | NHCH₃ | 2-Et | 3-CF₃ | H | |
| 16.33. | N | S | NHCH₃ | 2-prop | 4-CF₃ | H | |
| 16.34. | N | S | SCH₃ | 2-prop | 4-CF₃ | 6-Me | |
| 16.35. | N | SO | SCH₃ | H | 3-OCF₃ | H | |
| 16.36. | N | SO | SCH₃ | H | 5-OCF₃ | H | |
| 16.37. | CH | O | SCH₃ | H | 5-OCF₃ | 2-Me | |
| 16.38. | CH | O | SCH₃ | H | 5-OCF₃ | 4-Me | |
| 16.39. | N | O | OCH₃ | 2-CH₃ | 4-propynyl | H | |
| 16.40. | N | O | NHCH₃ | 2-CH₃ | 4-allyl | H | |
| 16.41. | N | O | NHCH₃ | 3-CH₃ | 6-propargyl | H | |
| 16.42. | N | S | NHCH₃ | 2-OCH₃ | 4-allyl | H | |
| 16.43. | N | O | NHCH₃ | 2-OCH₃ | 4-propargyl | H | |
| 16.44. | N | S | SCH₃ | 2-CH₃ | 4-O-allyl | H | |
| 16.45. | N | S | SCH₃ | 2-CH₃ | 4-O-propargyl | H | |
| 16.46. | N | O | OCH₃ | 2-OCH₃ | 4-O-allyl | H | |
| 16.47. | CH | O | OCH₃ | 2-OCH₃ | 4-O-propargyl | H | |
| 16.48. | CH | O | OCH₃ | 2-OCH₃ | 4-ethynyl | H | |
| 16.49. | CH | O | OCH₃ | 2-OCH₃ | 4-ethynyl | 6-Me | |
| 16.50. | N | O | OCH₃ | 2-O-allyl | 4-O-allyl | H | |
| 16.51. | N | O | OCH₃ | 2-O-allyl | 6-O-propargyl | H | |
| 16.52. | N | O | OCH₃ | 2-Cl | 4-O-allyl | H | |
| 16.53. | CH | O | OCH₃ | 2-Br | 4-O-propargyl | H | |
| 16.54. | N | O | NHCH₃ | 2-CF₃ | 4-ethynyl | H | |
| 16.55. | N | S | NHCH₃ | 2-CF₃ | 4-ethynyl | 6-Me | |
| 16.56. | N | S | NHCH₃ | H | 2-benzyl | H | |
| 16.57. | N | S | SCH₃ | H | 2-benzyloxy | H | |
| 16.58. | N | SO | SCH₃ | 2-CH₃ | 3-phenoxy | H | |
| 16.59. | N | SO | SCH₃ | 2-CH₃ | 3-phenoxy(4-Cl) | H | |
| 16.60. | CH | O | SCH₃ | 2-OCH₃ | 4-benzyloxy | H | |
| 16.61. | CH | O | SCH₃ | 3-OCH₃ | 5-benzyloxy(3-CF₃) | H | |
| 16.62. | N | O | OCH₃ | 3-OCH₃ | 6-benzyloxy(3-OCF₃) | H | |
| 16.63. | N | O | NHCH₃ | H | 4-cyclopropylmethyloxy | H | |
| 16.64. | N | O | NHCH₃ | 3-OCH₃ | 5-cyclopropylmethyloxy | H | |
| 16.65. | N | S | NHCH₃ | 3-OCH₃ | 5-(dichlorocyclopropyl)-methoxy | H | |
| 16.66. | N | O | NHCH₃ | H | 3- (CH₃)₂C=NOCH₃ | H | |
| 16.67. | N | S | SCH₃ | H | 4- CH₃C(=O)C(CH₃)=NOCH₃ | H | |

TABLE 16-continued (intermediates)

| Comp. No. | X | Y | Z | D₁ | D₂ | D₃ | Physical data |
|---|---|---|---|---|---|---|---|
| 16.68. | N | S | SCH₃ | H | 4- CH₃-C(=NOCH₃)-C(=NOCH₃)- | H | |
| 16.69. | N | O | OCH₃ | H | 3- CH₃-C(=NOCH₃)- | H | |
| 16.70. | CH | O | OCH₃ | H | 3- C₆H₅-C(=NOCH₃)- | H | |
| 16.71. | CH | O | OCH₃ | H | 4- C₆H₅-4-Cl-C(=NOCH₃)- | H | |
| 16.72. | CH | O | OCH₃ | H | 4- C₆H₄-4-phenoxy-C(=NOCH₃)- | H | |
| 16.73. | N | O | OCH₃ | H | 4- C₆H₄-4-(4-chlorophenoxy)-C(=NOCH₃)- | H | |
| 16.74. | N | O | OCH₃ | H | 4- C₆H₄-4-(4-chlorophenoxy)-C(=NOC₂H₅)- | H | |
| 16.75. | CH | S | OCH₃ | | 4- C₆H₄-4-OCH₂—C₆H₄-3-CF₃ -C(=N-O-C₂H₅)- | H | |
| 16.76. | N | O | OCH₃ | | 4- C₆H₄-4-OCH₂—C₆H₄-4-CF₃ -C(=N-O-C₂H₅)- | H | |
| 16.77. | N | SO | OCH₃ | | 4- C₆H₄-4-OCH₂—C₆H₄-2-CF₃ -C(=N-O-C₂H₅)- | H | |

TABLE 17

(intermediates)

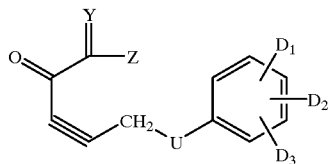

| Comp. No. | Y | Z | U | $D_1$ | $D_2$ | $D_3$ | Physical data |
|---|---|---|---|---|---|---|---|
| 17.1. | O | $OCH_3$ | O | H | H | H | |
| 17.2. | O | $OCH_3$ | O | 2-$CH_3$ | H | H | |
| 17.3. | O | $OCH_3$ | O | 3-$CH_3$ | H | H | |
| 17.4. | O | $OCH_3$ | S | 4-$CH_3$ | H | H | |
| 17.5. | O | $OCH_3$ | S | 2-$CH_3$ | 3-$CH_3$ | H | |
| 17.6. | O | $OCH_3$ | S | 2-$CH_3$ | 4-$CH_3$ | H | |
| 17.7. | O | $OCH_3$ | $NHCH_3$ | 2-$CH_3$ | 5-$CH_3$ | H | |
| 17.8. | O | $NHCH_3$ | O | 2-$CH_3$ | 6-$CH_3$ | H | |
| 17.9. | S | $NHCH_3$ | O | 2-Et | 4-$CH_3$ | H | |
| 17.10. | S | $NHCH_3$ | O | 2-i-Prop | 5-$CH_3$ | H | |
| 17.11. | S | $SCH_3$ | S | 2-$CH_3$ | 6-$CH_3$ | H | |
| 17.12. | SO | $SCH_3$ | S | 2-$CH_3$ | 6-$CH_3$ | 4-Me | |
| 17.13. | SO | $SCH_3$ | S | 2-$CH_3$ | 6-$CH_3$ | 4-Et | |
| 17.14. | O | $SCH_3$ | $NHCH_3$ | 2-Cl | H | H | |
| 17.15. | O | $SCH_3$ | NHBz | 3-Cl | H | H | |
| 17.16. | O | $OCH_3$ | NHEt | 4-Cl | H | H | |
| 17.17. | O | $NHCH_3$ | O | 2-$CH_3$ | 3-Cl | H | |
| 17.18. | O | $NHCH_3$ | O | 2-$CH_3$ | 4-Cl | H | |
| 17.19. | S | $NHCH_3$ | S | H | 2-$OCH_3$ | H | |
| 17.20. | O | $NHCH_3$ | S | H | 3-$OCH_3$ | H | |
| 17.21. | S | $SCH_3$ | S | H | 4-$OCH_3$ | H | |
| 17.22. | S | $SCH_3$ | O | H | 4-$OCF_3$ | H | |
| 17.23. | O | $OCH_3$ | O | 2-$OCH_3$ | 3-$OCH_3$ | H | |
| 17.24. | O | $OCH_3$ | S | 2-$OCH_3$ | 4-$OCH_3$ | H | |
| 17.25. | O | $OCH_3$ | S | 2-$OCH_3$ | 5-$OCH_3$ | H | |
| 17.26. | O | $OCH_3$ | $NHCH_3$ | 2-$OCH_3$ | 5-$OCH_3$ | 6-OMe | |
| 17.27. | O | $OCH_3$ | NHBz | 2-$OCH_3$ | 5-$OCH_3$ | 4-OMe | |
| 17.28. | O | $OCH_3$ | NHEt | H | 2-$CF_3$ | H | |
| 17.29. | O | $OCH_3$ | O | H | 3-$CF_3$ | H | |
| 17.30. | O | $OCH_3$ | O | H | 4-$CF_3$ | H | |
| 17.31. | O | $NHCH_3$ | S | 2-$CH_3$ | 4-$OCF_3$ | H | |
| 17.32. | S | $NHCH_3$ | S | 2-Et | 3-$CF_3$ | H | |
| 17.33. | S | $NHCH_3$ | O | 2-Prop | 4-$CF_3$ | H | |
| 17.34. | S | $SCH_3$ | O | 2-Prop | 4-$CF_3$ | 6-Me | |
| 17.35. | SO | $SCH_3$ | O | H | 3-$OCF_3$ | H | |
| 17.36. | SO | $SCH_3$ | S | H | 5-$OCF_3$ | H | |
| 17.37. | O | $SCH_3$ | S | H | 5-$OCF_3$ | 2-Me | |
| 17.38. | O | $SCH_3$ | $NHCH_3$ | H | 5-$OCF_3$ | 4-Me | |
| 17.39. | O | $OCH_3$ | NHBz | 2-$CH_3$ | 4-propynyl | H | |
| 17.40. | O | $NHCH_3$ | NHEt | 2-$CH_3$ | 4-allyl | H | |
| 17.41. | O | $NHCH_3$ | O | 3-$CH_3$ | 6-propargyl | H | |
| 17.42. | S | $NHCH_3$ | O | 2-$OCH_3$ | 4-allyl | H | |
| 17.43. | O | $NHCH_3$ | S | 2-$OCH_3$ | 4-propargyl | H | |
| 17.44. | S | $SCH_3$ | S | 2-$CH_3$ | 4-O-allyl | H | |
| 17.45. | S | $SCH_3$ | S | 2-$CH_3$ | 4-O-propargyl | H | |
| 17.46. | O | $OCH_3$ | O | 2-$OCH_3$ | 4-O-allyl | H | |
| 17.47. | O | $OCH_3$ | O | 2-$OCH_3$ | 4-O-propargyl | H | |
| 17.48. | O | $OCH_3$ | S | 2-$OCH_3$ | 4-ethynyl | H | |
| 17.49. | O | $OCH_3$ | S | 2-$OCH_3$ | 4-ethynyl | 6-Me | |
| 17.50. | O | $OCH_3$ | $NHCH_3$ | 2-O-allyl | 4-O-allyl | H | |
| 17.51. | O | $OCH_3$ | NHBz | 2-O-allyl | 6-O-propargyl | H | |
| 17.52. | O | $OCH_3$ | NHEt | 2-Cl | 4-O-allyl | H | |
| 17.53. | O | $OCH_3$ | O | 2-Br | 4-O-propargyl | H | |
| 17.54. | O | $NHCH_3$ | O | 2-$CF_3$ | 4-ethynyl | H | |
| 17.55. | S | $NHCH_3$ | S | 2-$CF_3$ | 4-ethynyl | 6-Me | |
| 17.56. | S | $NHCH_3$ | S | H | 2-benzyl | H | |
| 17.57. | S | $SCH_3$ | S | H | 2-benzyloxy | H | |
| 17.58. | SO | $SCH_3$ | O | 2-$CH_3$ | 3-phenoxy | H | |
| 17.59. | SO | $SCH_3$ | O | 2-$CH_3$ | 3-phenoxy(4-Cl) | H | |
| 17.60. | O | $SCH_3$ | S | 2-$OCH_3$ | 4-benzyloxy | H | |
| 17.61. | O | $SCH_3$ | S | 3-$OCH_3$ | 5-benzyloxy(3-$CF_3$) | H | |

TABLE 17-continued (intermediates)

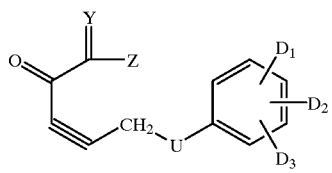

| Comp. No. | Y | Z | U | D$_1$ | D$_2$ | D$_3$ | Physical data |
|---|---|---|---|---|---|---|---|
| 17.62. | O | OCH$_3$ | NHCH$_3$ | 3-OCH$_3$ | 6-benzyloxy(3-OCF$_3$) | H | |
| 17.63. | O | NHCH$_3$ | NHBz | H | 4-cyclopropylmethyloxy | H | |
| 17.64. | O | NHCH$_3$ | NHEt | 3-OCH$_3$ | 5-cyclopropylmethyloxy | H | |
| 17.65. | S | NHCH$_3$ | O | 3-OCH$_3$ | 5-(dichlorocyclopropyl)-methoxy | H | |
| 17.66. | O | NHCH$_3$ | O | H | 3- C(CH$_3$)=NOCH$_3$ | H | |
| 17.67. | S | SCH$_3$ | S | H | 4- C(COCH$_3$)(CH$_3$)=NOCH$_3$ | H | |
| 17.68. | S | SCH$_3$ | S | H | 4- CH$_3$-C(=NOCH$_3$)-C(CH$_3$)=NOCH$_3$ | H | |
| 17.69. | O | OCH$_3$ | S | H | 3- C(CH$_3$)=NOCH$_3$ | H | |
| 17.70. | O | OCH$_3$ | O | H | 3- C(C$_6$H$_5$)=NOCH$_3$ | H | |
| 17.71. | O | OCH$_3$ | O | H | 4- C(C$_6$H$_5$-4-Cl)=NOCH$_3$ | H | |
| 17.72. | O | OCH$_3$ | S | H | 4- C(C$_6$H$_4$-4-phenoxy)=NOCH$_3$ | H | |
| 17.73. | O | OCH$_3$ | S | H | 4- C(C$_6$H$_4$-4-(4-chlorophenoxy))=NOCH$_3$ | H | |
| 17.74. | O | OCH$_3$ | NHCH$_3$ | H | 4- C(C$_6$H$_4$-4-(4-chlorophenoxy))=NOC$_2$H$_5$ | H | |

TABLE 17-continued (intermediates)

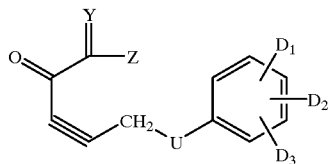

| Comp. No. | Y | Z | U | D₁ | D₂ | D₃ | Physical data |
|---|---|---|---|---|---|---|---|
| 17.75. | S | OCH₃ | NHBz | H | 4-C₆H₄-4-OCH₂—C₆H₄-3-CF₃ (with -C(CH₃)=N-OEt) | H | |
| 17.76. | O | OCH₃ | NHEt | 2-CH₃ | 4-C₆H₄-4-OCH₂—C₆H₄-4-CF₃ (with -C(CH₃)=N-OEt) | H | |
| 17.77. | SO | OCH₃ | O | 2-Cl | 4-C₆H₄-4-OCH₂—C₆H₄-2-CF₃ (with -C(CH₃)=N-OEt) | H | |
| 17.78. | O | OCH₃ | O | H | 3-CH=CH— | H | |
| 17.79. | S | OCH₃ | S | H | 3-CH₂—CH=CH₂ | 4-OMe | |
| 17.80. | O | OCH₃ | S | H | 3-CH₂—CH=CH₂ | 4-OEt | |
| 17.81. | SO | OCH₃ | S | H | 4-OCH₂—C₆H₅ | 6-OEt | |

TABLE 18

(intermediates)

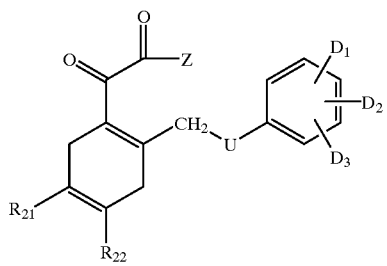

| Comp. No. | R₂₁ | R₂₂ | Z | U | D₁ | D₂ | D₃ | Physical data |
|---|---|---|---|---|---|---|---|---|
| 18.1 | CH₃ | CH₃ | OCH₃ | O | H | H | H | |
| 18.2 | CH₃ | CH₃ | OCH₃ | O | 2-CH₃ | H | H | |
| 18.3 | CH₃ | CH₃ | OCH₃ | O | 3-CH₃ | H | H | |
| 18.4 | CH₃ | CH₃ | OCH₃ | S | 4-CH₃ | H | H | |
| 18.5 | CH₃ | CH₃ | OCH₃ | S | 2-CH₃ | 3-CH₃ | H | |
| 18.6 | CH₃ | CH₃ | OCH₃ | S | 2-CH₃ | 4-CH₃ | H | |
| 18.7 | CH₃ | CH₃ | OCH₃ | NHCH₃ | 2-CH₃ | 5-CH₃ | H | |
| 18.8 | CH₃ | CH₃ | NHCH₃ | O | 2-CH₃ | 6-CH₃ | H | |
| 18.9 | OCH₃ | H | NHCH₃ | O | 2-Et | 4-CH₃ | H | |
| 18.10 | OCH₃ | H | NHCH₃ | O | 2-i-Prop | 5-CH₃ | H | |
| 18.11 | Cl | H | SCH₃ | S | 2-CH₃ | 6-CH₃ | H | |
| 18.12 | Cl | H | SCH₃ | S | 2-CH₃ | 6-CH₃ | 4-Me | |
| 18.13 | Cl | H | SCH₃ | S | 2-CH₃ | 6-CH₃ | 4-Et | |
| 18.14 | Cl | CH₃ | SCH₃ | NHCH₃ | 2-Cl | H | H | |

TABLE 18-continued (intermediates)

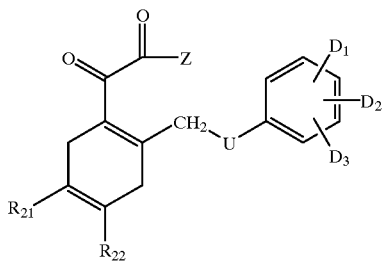

| Comp. No. | $R_{21}$ | $R_{22}$ | Z | U | $D_1$ | $D_2$ | $D_3$ | Physical data |
|---|---|---|---|---|---|---|---|---|
| 18.15 | Cl | $CH_3$ | $SCH_3$ | NHBz | 3-Cl | H | H | |
| 18.16 | Cl | $CH_3$ | $OCH_3$ | NHEt | 4-Cl | H | H | |
| 18.17 | $CH_3$ | $CH_3$ | $NHCH_3$ | O | 2-$CH_3$ | 3-Cl | H | |
| 18.18 | $CH_3$ | $CH_3$ | $NHCH_3$ | O | 2-$CH_3$ | 4-Cl | H | |
| 18.19 | $CH_3$ | $CH_3$ | $NHCH_3$ | S | H | 2-$OCH_3$ | H | |
| 18.20 | $CH_3$ | $CH_3$ | $NHCH_3$ | S | H | 3-$OCH_3$ | H | |
| 18.21 | $CH_3$ | $CH_3$ | $SCH_3$ | S | H | 4-$OCH_3$ | H | |
| 18.22 | $CH_3$ | $CH_3$ | $SCH_3$ | O | H | 4-$OCF_3$ | H | |
| 18.23 | $CH_3$ | $CH_3$ | $OCH_3$ | O | 2-$OCH_3$ | 3-$OCH_3$ | H | |
| 18.24 | $CH_3$ | $CH_3$ | $OCH_3$ | S | 2-$OCH_3$ | 4-$OCH_3$ | H | |
| 18.25 | $OCH_3$ | H | $OCH_3$ | S | 2-$OCH_3$ | 5-$OCH_3$ | H | |
| 18.26 | $OCH_3$ | H | $OCH_3$ | $NHCH_3$ | 2-$OCH_3$ | 5-$OCH_3$ | 6-OMe | |
| 18.27 | Cl | H | $OCH_3$ | NHBz | 2-$OCH_3$ | 5-$OCH_3$ | 4-OMe | |
| 18.28 | Cl | H | $OCH_3$ | NHEt | H | 2-$CF_3$ | H | |
| 18.29 | Cl | H | $OCH_3$ | O | H | 3-$CF_3$ | H | |
| 18.30 | Cl | $CH_3$ | $OCH_3$ | O | H | 4-$CF_3$ | H | |
| 18.31 | Cl | $CH_3$ | $NHCH_3$ | S | 2-$CH_3$ | 4-$OCF_3$ | H | |
| 18.32 | Cl | $CH_3$ | $NHCH_3$ | S | 2-Et | 3-$CF_3$ | H | |
| 18.33 | $CH_3$ | $CH_3$ | $NHCH_3$ | S | 2-Prop | 4-$CF_3$ | H | |
| 18.34 | $CH_3$ | $CH_3$ | $SCH_3$ | O | 2-Prop | 4-$CF_3$ | 6-Me | |
| 18.35 | $CH_3$ | $CH_3$ | $SCH_3$ | O | H | 3-$OCF_3$ | H | |
| 18.36 | $CH_3$ | $CH_3$ | $SCH_3$ | S | H | 5-$OCF_3$ | H | |
| 18.37 | $CH_3$ | $CH_3$ | $SCH_3$ | S | H | 5-$OCF_3$ | 2-Me | |
| 18.38 | $CH_3$ | $CH_3$ | $SCH_3$ | $NHCH_3$ | H | 5-$OCF_3$ | 4-Me | |
| 18.39 | $CH_3$ | $CH_3$ | $OCH_3$ | NHBz | 2-$CH_3$ | 4-propynyl | H | |
| 18.40 | $CH_3$ | $CH_3$ | $NHCH_3$ | NHEt | 2-$CH_3$ | -allyl | H | |
| 18.41 | $OCH_3$ | H | $NHCH_3$ | O | 3-$CH_3$ | 6-propargyl | H | |
| 18.42 | $OCH_3$ | H | $NHCH_3$ | O | 2-$OCH_3$ | 4-allyl | H | |
| 18.43 | Cl | H | $NHCH_3$ | S | 2-$OCH_3$ | 4-propargyl | H | |
| 18.44 | Cl | H | $SCH_3$ | S | 2-$CH_3$ | 4-O-allyl | H | |
| 18.45 | Cl | H | $SCH_3$ | S | 2-$CH_3$ | 4-O-propargyl | H | |
| 18.46 | Cl | $CH_3$ | $OCH_3$ | O | 2-$OCH_3$ | 4-O-allyl | H | |
| 18.47 | Cl | $CH_3$ | $OCH_3$ | O | 2-$OCH_3$ | 4-O-propargyl | H | |
| 18.48 | Cl | $CH_3$ | $OCH_3$ | S | 2-$OCH_3$ | 4-ethynyl | H | |
| 18.49 | $CH_3$ | $CH_3$ | $OCH_3$ | S | 2-$OCH_3$ | 4-ethynyl | 6-Me | |
| 18.50 | $CH_3$ | $CH_3$ | $OCH_3$ | $NHCH_3$ | 2-O-allyl | 4-O-allyl | H | |
| 18.51 | $CH_3$ | $CH_3$ | $OCH_3$ | NHBz | 2-O-allyl | 6-O-propargyl | H | |
| 18.52 | $CH_3$ | $CH_3$ | $OCH_3$ | NHEt | 2-Cl | 4-O-allyl | H | |
| 18.53 | $CH_3$ | $CH_3$ | $OCH_3$ | O | 2-Br | 4-O-propargyl | H | |
| 18.54 | $CH_3$ | $CH_3$ | $NHCH_3$ | O | 2-$CF_3$ | 4-ethynyl | H | |
| 18.55 | $CH_3$ | $CH_3$ | $NHCH_3$ | S | 2-$CF_3$ | 4-ethynyl | 6-Me | |
| 18.56 | $CH_3$ | $CH_3$ | $NHCH_3$ | S | H | 2-benzyl | H | |
| 18.57 | $OCH_3$ | H | $SCH_3$ | S | H | 2-benzyloxy | H | |
| 18.58 | $OCH_3$ | H | $SCH_3$ | O | 2-$CH_3$ | 3-phenoxy | H | |
| 18.59 | Cl | H | $SCH_3$ | O | 2-$CH_3$ | phenoxy(4-Cl) | H | |
| 18.60 | Cl | H | $SCH_3$ | S | 2-$OCH_3$ | 4-benzyloxy | H | |
| 18.61 | Cl | H | $SCH_3$ | S | 3-$OCH_3$ | 5-benzyloxy(3-$CF_3$) | H | |
| 18.62 | Cl | $CH_3$ | $OCH_3$ | $NHCH_3$ | 3-$OCH_3$ | 6-benzyloxy(3-$OCF_3$) | H | |
| 18.63 | Cl | $CH_3$ | $NHCH_3$ | NHBz | H | 4-cyclopropyl-methyloxy | H | |
| 18.64 | Cl | $CH_3$ | $NHCH_3$ | NHEt | 3-$OCH_3$ | 5-cyclopropyl-methyloxy | H | |
| 18.65 | Cl | H | $NHCH_3$ | O | 3-$OCH_3$ | 2-(dichlorocyclopropyl)methoxy | H | |

TABLE 18-continued (intermediates)

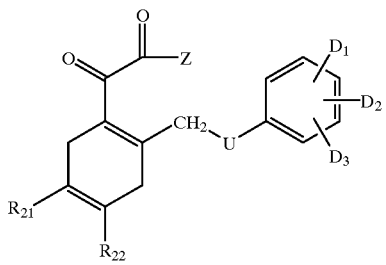

| Comp. No. | $R_{21}$ | $R_{22}$ | Z | U | $D_1$ | $D_2$ | $D_3$ | Physical data |
|---|---|---|---|---|---|---|---|---|
| 18.66 | CH$_3$ | CH$_3$ | NHCH$_3$ | O | H | 3- CH$_3$-C(=NOCH$_3$)- | H | |
| 18.67 | CH$_3$ | CH$_3$ | SCH$_3$ | S | H | 3- CH$_3$-C(=NOCH$_3$)-CO- | H | |
| 18.68 | CH$_3$ | CH$_3$ | SCH$_3$ | S | H | 4- CH$_3$-C(=NOCH$_3$)-C(CH$_3$)=NOCH$_3$ | H | |

TABLE 19

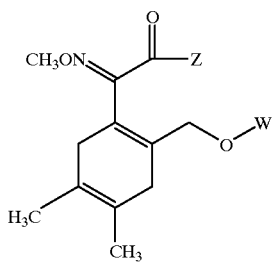

| Comp. No. | Z | W | Physical data |
|---|---|---|---|
| 19.01. | OMe | 3-C$_6$H$_4$—C≡C—C$_6$H$_3$Cl$_2$(2',4') | |
| 19.02. | OMe | 3-C$_6$H$_4$—C≡C—C$_6$H$_5$ | 98–101° |
| 19.03. | OMe | 3-C$_6$H$_4$—C≡C—C$_6$H$_4$(OCH$_3$)(4') | |
| 19.04. | OMe | 3-C$_6$H$_4$—C≡C—C$_6$H$_3$(CF$_3$)(3',5') | |
| 19.05. | OMe | 3-C$_6$H$_4$—C≡C—C$_6$H$_4$(CF$_3$)(3') | |
| 19.06. | OMe | 3-C$_6$H$_4$—C≡C—CO—C$_6$H$_4$(CF$_3$)(3') | |
| 19.07. | OMe | 3-C$_6$H$_4$—C≡C—CO—C$_6$H$_5$ | |
| 19.08. | OMe | 3-C$_6$H$_4$—C≡C—CO—C$_6$H$_4$(Cl)(3') | |
| 19.09. | OMe | 3-C$_6$H$_4$—C≡C—C≡C—C$_3$H$_7$(i) | |
| 19.10. | OMe | 3-C$_6$H$_4$—C≡C—C≡C—C(CH$_3$)$_2$—OH | |
| 19.11. | OMe | 3-C$_6$H$_4$—(C≡C)$_2$—C(CH$_3$)$_2$—OCOCH$_3$ | |
| 19.12. | OMe | 3-C$_6$H$_4$—C≡C—C(CH$_3$)$_2$—OH | |
| 19.13. | OMe | 3-C$_6$H$_4$—C≡C-pyrazinyl(2') | |
| 19.14. | OMe | 3-C$_6$H$_4$—C≡C-pyridyl(3') | |
| 19.15. | OMe | 3-C$_6$H$_4$—C≡C—CO-pyridyl(3') | |
| 19.16. | OMe | 3-C$_6$H$_4$—C≡C-pyridyl(2') | |
| 19.17. | OMe | 3-C$_6$H$_4$—C≡C-pyridyl(4') | |
| 19.18. | OMe | 3-C$_6$H$_4$—C≡C—C$_6$H$_4$(CF$_3$)(4') | |
| 19.19. | OMe | 3-C$_6$H$_4$—C≡C—C$_6$H$_4$(Cl)(4') | |

TABLE 19-continued

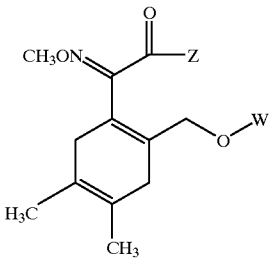

| Comp. No. | Z | W | Physical data |
|---|---|---|---|
| 19.20. | OMe | 3-$C_6H_4$—C≡C—$CH_2$—OH | |
| 19.21. | OMe | 3-$C_6H_4$—C≡C-pyrimidinyl(2') | |
| 19.22. | OMe | 3-$C_6H_4$—C≡C-pyrimidinyl(4') | |
| 19.23. | OMe | 3-$C_6H_4$—C≡C-pyrimidinyl(5') | |
| 19.24. | OMe | 3-$C_6H_4$—C≡C—I | |
| 19.25. | OMe | 3-$C_6H_4$—C≡C—$CH_3$ | |
| 19.26. | OMe | 3-$C_6H_4$—C≡C—Br | |
| 19.27. | OMe | 3-$C_6H_4$—C≡C—$C_6H_4$(Br)(4') | |
| 19.28. | OMe | 3-$C_6H_4$—C≡C—$C_6H_3(OCH_3)_3$(3',4',5') | |
| 19.29. | OMe | 3-$C_6H_4$—C≡C—$C_6H_3(CH_3)_2$(3',5') | |
| 19.30. | OMe | 3-$C_6H_4$—C≡C-thiazolyl(2') | |
| 19.31. | OMe | 3-$C_6H_4$—C≡C-oxazolyl(2') | |
| 19.32. | OMe | 3-$C_6H_4$—C≡C-thienyl(2') | |
| 19.33. | OMe | 3-$C_6H_4$—C≡C-thienyl(3') | |
| 19.34. | OMe | 3-$C_6H_4$—C≡C-Et | |
| 19.35. | OMe | 4-$C_6H_4$—C≡C—H | |
| 19.36. | OMe | 2-$C_6H_4$—C≡C—H | |
| 19.37. | OMe | 4-$C_6H_4$—C≡C—$CH_3$ | |
| 19.38. | OMe | 2-$C_6H_4$—C≡C—Br | |
| 19.39. | OMe | 2-$C_6H_4$—C≡C—$C(CH_3)_2$—OH | |
| 19.40. | OMe | 4-$C_6H_4$—C≡C—$C(CH_3)_2$—OH | |
| 19.41. | OMe | 3-$C_6H_4$—C≡C—$CF_3$ | |
| 19.42. | OMe | 3-$C_6H_4$—C≡C—COOEt | |
| 19.43. | OMe | 3-$C_6H_4$—C≡C—COOMe | |
| 19.44. | OMe | 2-$C_6H_4$—C≡C—$C(CH_3)_2$—OH | |
| 19.45. | OMe | 3-$C_6H_4$—C≡C—$C(CH_3)_2$—O—$CH_3$ | |
| 19.46. | OMe | 4-$C_6H_4$—C≡C—$C(CH_3)_2$—O—$CH_3$ | |
| 19.47. | OMe | 3-$C_6H_4$—C≡C—$CH_2$—OMe | |
| 19.48. | OMe | 3-$C_6H_4$—C≡C—$C_4H_9$(n) | |
| 19.49. | OMe | 3-$C_6H_4$—C≡C—$C_3H_7$(n) | |
| 19.50. | OMe | 3-$C_6H_4$—C≡C—$C_8H_{17}$(n) | |
| 19.51. | NHMe | 3-$C_6H_4$—C≡C—$C_6H_3Cl_2$(2',4') | |
| 19.52. | NHMe | 3-$C_6H_4$—C≡C—$C_6H_5$ | |
| 19.53. | NHMe | 3-$C_6H_4$—C≡C—$C_6H_4(OCH_3)$(4') | |
| 19.54. | NHMe | 3-$C_6H_4$—C≡C—$C_6H_3(CF_3)$(3',5') | |
| 19.55. | NHMe | 3-$C_6H_4$—C≡C—$C_6H_4(CF_3)$(3') | |
| 19.56. | NHMe | 3-$C_6H_4$—C≡C—CO—$C_6H_4(CF_3)$(3') | |
| 19.57. | NHMe | 3-$C_6H_4$—C≡C—CO—$C_6H_5$ | |
| 19.58. | NHMe | 3-$C_6H_4$—C≡C—CO—$C_6H_4(Cl)$(3') | |
| 19.59. | NHMe | 3-$C_6H_4$—C≡C—C≡C—$C_3H_7$(i) | |
| 19.60. | NHMe | 3-$C_6H_4$—C≡C—C≡C—$C(CH_3)_2$—OH | |
| 19.61. | NHMe | 3-$C_6H_4$—$(C≡C)_2$—$C(CH_3)_2$—$OCOCH_3$ | |
| 19.62. | NHMe | 3-$C_6H_4$—C≡C—$C(CH_3)_2$—OH | |
| 19.63. | NHMe | 3-$C_6H_4$—C≡C-pyrazinyl(2') | |
| 19.64. | NHMe | 3-$C_6H_4$—C≡C-pyridyl(3') | |
| 19.65. | NHMe | 3-$C_6H_4$—C≡C—CO-pyridyl(3') | |
| 19.66. | NHMe | 3-$C_6H_4$—C≡C-pyridyl(2') | |
| 19.67. | NHMe | 3-$C_6H_4$—C≡C-pyridyl(4') | |
| 19.68. | NHMe | 3-$C_6H_4$—C≡C—$C_6H_4(CF_3)$(4') | |
| 19.69. | NHMe | 3-$C_6H_4$—C≡C—$C_6H_4(Cl)$(4') | |
| 19.70. | NHMe | 3-$C_6H_4$—C≡C—$CH_2$—OH | |
| 19.71. | NHMe | 3-$C_6H_4$—C≡C-pyrimidinyl(2') | |
| 19.72. | NHMe | 3-$C_6H_4$—C≡C-pyrimidinyl(4') | |
| 19.73. | NHMe | 3-$C_6H_4$—C≡C-pyrimidinyl(5') | |
| 19.74. | NHMe | 3-$C_6H_4$—C≡C—I | |
| 19.75. | NHMe | 3-$C_6H_4$—C≡C—$CH_3$ | |
| 19.76. | NHMe | 3-$C_6H_4$—C≡C—Br | |
| 19.77. | NHMe | 3-$C_6H_4$—C≡C—$C_6H_4$(Br)(4') | |
| 19.78. | NHMe | 3-$C_6H_4$—C≡C—$C_6H_3(OCH_3)_3$(3',4',5') | |
| 19.79. | NHMe | 3-$C_6H_4$—C≡C—$C_6H_3(CH_3)_2$(3',5') | |
| 19.80. | NHMe | 3-$C_6H_4$—C≡C-thiazolyl(2') | |
| 19.81. | NHMe | 3-$C_6H_4$—C≡C-oxazolyl(2') | |

TABLE 19-continued

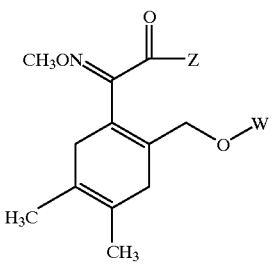

| Comp. No. | Z | W | Physical data |
|---|---|---|---|
| 19.82. | NHMe | 3-C$_6$H$_4$—C≡C-thienyl(2') | |
| 19.83. | NHMe | 3-C$_6$H$_4$—C≡C-thienyl(3') | |
| 19.84. | NHMe | 3-C$_6$H$_4$—C≡C-Et | |
| 19.85. | NHMe | 4-C$_6$H$_4$—C≡C—H | |
| 19.86. | NHMe | 2-C$_6$H$_4$—C≡C—H | |
| 19.87. | NHMe | 4-C$_6$H$_4$—C≡C—CH$_3$ | |
| 19.88. | NHMe | 2-C$_6$H$_4$—C≡C—Br | |
| 19.89. | NHMe | 2-C$_6$H$_4$—C≡C—C(CH$_3$)$_2$—OH | |
| 19.90. | NHMe | 4-C$_6$H$_4$—C≡C—C(CH$_3$)$_2$—OH | |
| 19.91. | NHMe | 3-C$_6$H$_4$—C≡C—CF$_3$ | |
| 19.92. | NHMe | 3-C$_6$H$_4$—C≡C—COOEt | |
| 19.93. | NHMe | 3-C$_6$H$_4$—C≡C—COOMe | |
| 19.94. | NHMe | 2-C$_6$H$_4$—C≡C—C(CH$_3$)$_2$—OH | |
| 19.95. | NHMe | 3-C$_6$H$_4$—C≡C—C(CH$_3$)$_2$—O—CH$_3$ | |
| 19.96. | NHMe | 4-C$_6$H$_4$—C≡C—C(CH$_3$)$_2$—O—CH$_3$ | |
| 19.97. | NHMe | 3-C$_6$H$_4$—C≡C—CH$_2$—OMe | |
| 19.98. | NHMe | 3-C$_6$H$_4$—C≡C—C$_4$H$_9$(n) | |
| 19.99. | NHMe | 3-C$_6$H$_4$—C≡C—C$_3$H$_7$(n) | |
| 19.100. | NHMe | 3-C$_6$H$_4$—C≡C—C$_8$H$_{17}$(n) | |
| 19.101. | NHMe | 3-C$_6$H$_4$—C≡C—C$_6$H$_4$(CH$_3$)(3') | |
| 19.102. | NHMe | 3-C$_6$H$_4$—C≡C—CH$_2$-morpholinyl(1) | |
| 19.103. | NHMe | 3-C$_6$H$_4$—CH$_2$—CH$_2$—CH$_2$-morpholinyl(1) | |
| 19.104. | NHMe | 3-C$_6$H$_4$—C≡C—CH$_2$—Cl | |
| 19.105. | OMe | 3-C$_6$H$_4$—C≡C—C$_6$H$_4$(CH$_3$)(3') | |
| 19.106. | NHMe | 3-C$_6$H$_4$—C≡C—CH$_2$—O—C$_6$H$_3$(Cl$_2$)(2',4') | |
| 19.107. | NHMe | 3-C$_6$H$_4$—C≡C—CH$_2$—O—C$_6$H$_4$(CH$_3$)(2') | oil |
| 19.108. | NHMe | 3-C$_6$H$_4$—C≡C—CH$_2$—O—C$_6$H$_4$(CH$_3$)(3') | |
| 19.109. | OMe | 3-C$_6$H$_4$—C≡C—CH$_2$—O—N═C(CH$_3$)C$_6$H$_4$(CF$_3$)(3') | oil |
| 19.110. | OMe | 3-C$_6$H$_4$—C≡C—CH(OH)—C$_6$H$_4$(F)(4')OC$_6$H$_5$(3') | oil |
| 19.111. | OMe | 3-C$_6$H$_4$—C≡C—(CH$_2$)$_3$—O—C$_6$H$_4$(OC$_6$H$_5$)(4') | oil |

TABLE 19a

Compounds of the formula

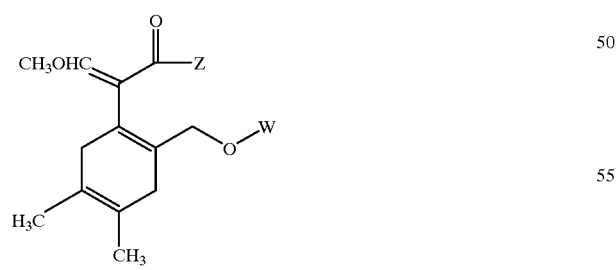

in which Z and W have the meanings of the corresponding compounds of Table 19.

TABLE 20

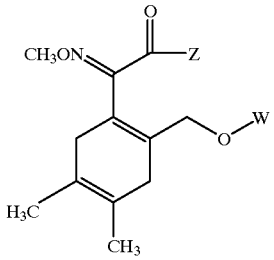

| Comp. No. | Z | W | Physical data |
|---|---|---|---|
| 20.001. | OMe | 3-C$_6$H$_4$—CH=CH—C$_6$H$_3$Cl$_2$(2',4') | |
| 20.002. | OMe | 3-C$_6$H$_4$—CH=CH—C$_6$H$_5$ | |
| 20.003. | OMe | 3-C$_6$H$_4$—CH=CH—C$_6$H$_4$(OCH$_3$)(4') | |
| 20.004. | OMe | 3-C$_6$H$_4$—CH=CH—C$_6$H$_3$(CF$_3$)(3',5') | |
| 20.005. | OMe | 3-C$_6$H$_4$—CH=CH—C$_6$H$_4$(CF$_3$)(3') | |
| 20.006. | OMe | 3-C$_6$H$_4$—CH=CH—CO—C$_6$H$_4$(CF$_3$)(3') | |
| 20.007. | OMe | 3-C$_6$H$_4$—CH=CH—CO—C$_6$H$_5$ | |
| 20.008. | OMe | 3-C$_6$H$_4$—CH=CH—CO—C$_6$H$_4$(Cl)(3') | |
| 20.009. | OMe | 3-C$_6$H$_4$—CH=CH—C(CH$_3$)$_2$—OH | |
| 20.010. | OMe | 3-C$_6$H$_4$—CH=CH-pyrazinyl(2') | |
| 20.011. | OMe | 3-C$_6$H$_4$—CH=CH-pyridyl(3') | |
| 20.012. | OMe | 3-C$_6$H$_4$—CH=CH-CO-pyridyl(3') | |
| 20.013. | OMe | 3-C$_6$H$_4$—CH=CH-pyridyl(2') | |
| 20.014. | OMe | 3-C$_6$H$_4$—CH=CH-pyridyl(4') | |
| 20.015. | OMe | 3-C$_6$H$_4$—CH=CH—C$_6$H$_4$(CF$_3$)(4') | |
| 20.016. | OMe | 3-C$_6$H$_4$—CH=CH—C$_6$H$_4$(Cl)(4') | |
| 20.017. | OMe | 3-C$_6$H$_4$—CH=CH—CH$_2$—OH | |
| 20.018. | OMe | 3-C$_6$H$_4$—CH=CH-pyrimidinyl(2') | |
| 20.019. | OMe | 3-C$_6$H$_4$—CH=CH-pyrimidinyl(4') | |
| 20.020. | OMe | 3-C$_6$H$_4$—CH=CH-pyrimidinyl(5') | |
| 20.021. | OMe | 3-C$_6$H$_4$—CH=CH—I | |
| 20.022. | OMe | 3-C$_6$H$_4$—CH=CH—CH$_3$ | |
| 20.023. | OMe | 3-C$_6$H$_4$—CH=CH—Br | |
| 20.024. | OMe | 3-C$_6$H$_4$—CH=CH—C$_6$H$_4$(Br)(4') | |
| 20.025. | OMe | 3-C$_6$H$_4$—CH=CH—C$_6$H$_2$(OCH$_3$)$_3$(3',4',5') | |
| 20.026. | OMe | 3-C$_6$H$_4$—CH=CH—C$_6$H$_3$(CH$_3$)$_2$(3',5') | |
| 20.027. | OMe | 3-C$_6$H$_4$—CH=CH-thiazolyl(2') | |
| 20.028. | OMe | 3-C$_6$H$_4$—CH=CH-oxazolyl(2') | |
| 20.029. | OMe | 3-C$_6$H$_4$—CH=CH-thienyl(2') | |
| 20.030. | OMe | 3-C$_6$H$_4$—CH=CH-thienyl(3') | |
| 20.031. | OMe | 3-C$_6$H$_4$—CH=CH-Et | |
| 20.032. | OMe | 4-C$_6$H$_4$—CH=CH$_2$ | |
| 20.033. | OMe | 2-C$_6$H$_4$—CH=CH$_2$ | |
| 20.034. | OMe | 4-C$_6$H$_4$—CH=CH—CH$_3$ | |
| 20.035. | OMe | 2-C$_6$H$_4$—CH=CH—Br | |
| 20.036. | OMe | 2-C$_6$H$_4$—CH=CH—C(CH$_3$)$_2$—OH | |
| 20.037. | OMe | 4-C$_6$H$_4$—CH=CH-(CH$_3$)$_2$—OH | |
| 20.038. | OMe | 3-C$_6$H$_4$—CH=CH—CF$_3$ | |
| 20.039. | OMe | 3-C$_6$H$_4$—CH=CH—COOEt | |
| 20.040. | OMe | 3-C$_6$H$_4$—CH=CH—COOMe | |
| 20.041. | OMe | 2-C$_6$H$_4$—CH=CH—C(CH$_3$)$_2$—OH | |
| 20.042. | OMe | 3-C$_6$H$_4$—CH=CH—C(CH$_3$)$_2$—O—CH$_3$ | |
| 20.043. | OMe | 4-C$_6$H$_4$—CH=CH—C(CH$_3$)$_2$—O—CH$_3$ | |
| 20.044. | OMe | 3-C$_6$H$_4$—CH=CH—CH$_2$—OMe | |
| 20.045. | OMe | 3-C$_6$H$_4$—CH=CH—C$_4$H$_9$(n) | |
| 20.046. | OMe | 3-C$_6$H$_4$—CH=CH—C$_3$H$_7$(n) | |
| 20.047. | OMe | 3-C$_6$H$_4$—CH=CH—C$_8$H$_{17}$(n) | |
| 20.048. | NHMe | 3-C$_6$H$_4$—CH=CH—C$_6$H$_3$Cl$_2$(2',4') | |
| 20.049. | NHMe | 3-C$_6$H$_4$—CH=CH—C$_6$H$_5$ | |
| 20.050. | NHMe | 3-C$_6$H$_4$—CH=CH—C$_6$H$_4$(OCH$_3$)(4') | |
| 20.051. | NHMe | 3-C$_6$H$_4$—CH=CH—C$_6$H$_3$(CF$_3$)$_2$(3',5') | |
| 20.052. | NHMe | 3-C$_6$H$_4$—CH=CH—C$_6$H$_4$(CF$_3$)(3') | |
| 20.053. | NHMe | 3-C$_6$H$_4$—CH=CH—CO—C$_6$H$_4$(CF$_3$)(3') | |
| 20.054. | NHMe | 3-C$_6$H$_4$—CH=CH—CO—C$_6$H$_5$ | |
| 20.055. | NHMe | 3-C$_6$H$_4$—CH=CH—CO—C$_6$H$_4$(Cl)(3') | |
| 20.056. | NHMe | 3-C$_6$H$_4$—CH=CH—C(CH$_3$)$_2$—OH | |
| 20.057. | NHMe | 3-C$_6$H$_4$—CH=CH-pyrazinyl(2') | |
| 20.058. | NHMe | 3-C$_6$H$_4$—CH=CH-pyridyl(3') | |
| 20.059 | NHMe | 3-C$_6$H$_4$—CH=CH-CO-pyridyl(3') | |
| 20.060. | NHMe | 3-C$_6$H$_4$—CH=CH-pyridyl(2') | |
| 20.061. | NHMe | 3-C$_6$H$_4$—CH=CH-pyridyl(4') | |
| 20.062. | NHMe | 3-C$_6$H$_4$—CH=CH—C$_6$H$_4$(CF$_3$)(4') | |

TABLE 20-continued

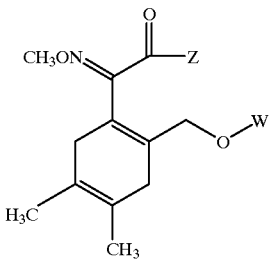

| Comp. No. | Z | W | Physical data |
|---|---|---|---|
| 20.063. | NHMe | 3-C₆H₄—CH=CH—C₆H₄(Cl)(4') | |
| 20.064. | NHMe | 3-C₆H₄—CH=CH—CH₂—OH | |
| 20.065. | NHMe | 3-C₆H₄—CH=CH-pyrimidinyl(2') | |
| 20.066. | NHMe | 3-C₆H₄—CH=CH-pyrimidinyl(4') | |
| 20.067. | NHMe | 3-C₆H₄—CH=CH-pyrimidinyl(5') | |
| 20.068. | NHMe | 3-C₆H₄—CH=CH—I | |
| 20.069. | NHMe | 3-C₆H₄—CH=CH—CH₃ | |
| 20.070. | NHMe | 3-C₆H₄—CH=CH—Br | |
| 20.071. | NHMe | 3-C₆H₄—CH=CH—C₆H₄(Br)(4') | |
| 20.072. | NHMe | 3-C₆H₄—CH=CH—C₆H₂(OCH₃)₃(3',4',5') | |
| 20.073. | NHMe | 3-C₆H₄—CH=CH—C₆H₃(CH₃)₂(3',5') | |
| 20.074. | NHMe | 3-C₆H₄—CH=CH-thiazolyl(2') | |
| 20.075. | NHMe | 3-C₆H₄—CH=CH-oxazolyl(2') | |
| 20.076. | NHMe | 3-C₆H₄—CH=CH-thienyl(2') | |
| 20.077. | NHMe | 3-C₆H₄—CH=CH-thienyl(3') | |
| 20.078. | NHMe | 3-C₆H₄—CH=CH-Et | |
| 20.079. | NHMe | 4-C₆H₄—CH=CH₂ | |
| 20.080. | NHMe | 2-C₆H₄—CH=CH₂ | |
| 20.081. | NHMe | 4-C₆H₄—CH=CH—CH₃ | |
| 20.082. | NHMe | 2-C₆H₄—CH=CH—Br | |
| 20.083. | NHMe | 2-C₆H₄—CH=CH—C(CH₃)₂—OH | |
| 20.084. | NHMe | 4-C₆H₄—CH=CH—C(CH₃)₂—OH | |
| 20.085. | NHMe | 3-C₆H₄—CH=CH—CF₃ | |
| 20.086. | NHMe | 3-C₆H₄—CH=CH—COOEt | |
| 20.087. | NHMe | 3-C₆H₄—CH=CH—COOMe | |
| 20.088. | NHMe | 2-C₆H₄—CH=CH—C(CH₃)₂—OH | |
| 20.089. | NHMe | 3-C₆H₄—CH=CH—C(CH₃)₂—O—CH₃ | |
| 20.090. | NHMe | 4-C₆H₄—CH=CH—C(CH₃)₂—O—CH₃ | |
| 20.091. | NHMe | 3-C₆H₄—CH=CH—CH₂—OMe | |
| 20.092. | NHMe | 3-C₆H₄—CH=CH—C₄H₉(n) | |
| 20.093. | NHMe | 3-C₆H₄—CH=CH—C₃H₇(n) | |
| 20.094. | NHMe | 3-C₆H₄—CH=CH—C₈H₁₇(n) | |
| 20.095. | NHMe | 3-C₆H₄—CH=CH—C₆H₄(CH₃)(3') | |
| 20.096. | NHMe | 3-C₆H₄—CH=CH—CH₂-morpholinyl(1) | |
| 20.097. | NHMe | 3-C₆H₄—CH=CH—CH₂-piperidinyl(1) | |
| 20.098. | NHMe | 3-C₆H₄—CH=CH—CH₂—Cl | |
| 20.099. | OMe | 3-C₆H₄—CH=CH—C₆H₄(CH₃)(3') | |
| 20.100. | NHMe | 3-C₆H₄—CH=CH—CH₂—O—C₆H₃(Cl₂)(2',4') | |
| 20.101. | NHMe | 3-C₆H₄—CH=CH—CH₂—O—C₆H₄(CH₃)(2') | |
| 20.102. | NHMe | 3-C₆H₄—CH=CH—CH₂—O—C₆H₄(CH₃)(3') | |

TABLE 20a

Compounds of the formula

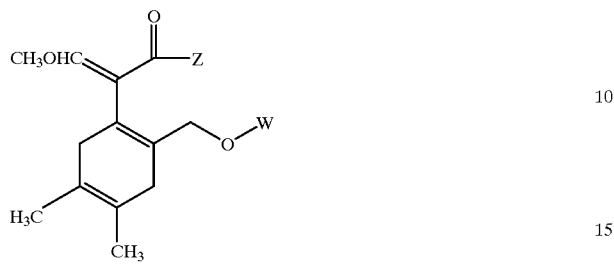

in which Z and W have the meanings of the corresponding compounds of Table 20.

TABLE 21

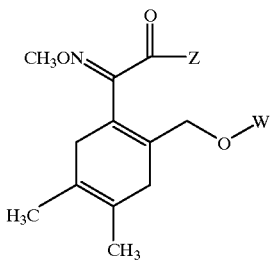

| Comp. No. | Z | W | Physical data |
|---|---|---|---|
| 21.001. | OMe | 3-C$_6$H$_4$—CH$_2$—CH$_2$—C$_6$H$_3$Cl$_2$(2',4') | |
| 21.002. | OMe | 3-C$_6$H$_4$—CH$_2$—CH$_2$—C$_6$H$_5$ | |
| 21.003. | OMe | 3-C$_6$H$_4$—CH$_2$—CH$_2$—C$_6$H$_4$(OCH$_3$)(4') | |
| 21.004. | OMe | 3-C$_6$H$_4$—CH$_2$—CH$_2$—C$_6$H$_3$(CF$_3$)(3', 5') | |
| 21.005. | OMe | 3-C$_6$H$_4$—CH$_2$—CH$_2$—C$_6$H$_4$(CF$_3$)(3') | |
| 21.006. | OMe | 3-C$_6$H$_4$—CH$_2$—CH$_2$—CO—C$_6$H$_4$(CF$_3$)(3') | |
| 21.007. | OMe | 3-C$_6$H$_4$—CH$_2$—CH$_2$—CO—C$_6$H$_5$ | |
| 21.008. | OMe | 3-C$_6$H$_4$—CH$_2$—CH$_2$—CO—C$_6$H$_4$(Cl)(3') | |
| 21.009. | OMe | 3-C$_6$H$_4$—CH$_2$—CH$_2$—C(CH$_3$)$_2$—OH | |
| 21.010. | OMe | 3-C$_6$H$_4$—CH$_2$—CH$_2$-pyrazinyl(2') | |
| 21.011. | OMe | 3-C$_6$H$_4$—CH$_2$—CH$_2$-pyridyl(31) | |
| 21.012. | OMe | 3-C$_6$H$_4$—CH$_2$—CH$_2$—CO-pyridyl(31) | |
| 21.013. | OMe | 3-C$_6$H$_4$—CH$_2$—CH$_2$-pyridyl(21) | |
| 21.014. | OMe | 3-C$_6$H$_4$—CH$_2$—CH$_2$-pyridyl(41) | |
| 21.015. | OMe | 3-C$_6$H$_4$—CH$_2$—CH$_2$—C$_6$H$_4$(CF$_3$)(4') | |
| 21.016. | OMe | 3-C$_6$H$_4$—CH$_2$—CH$_2$—C$_6$H$_4$(Cl)(4') | |
| 21.017. | OMe | 3-C$_6$H$_4$—CH$_2$—CH$_2$—CH$_2$—OH | |
| 21.018. | OMe | 3-C$_6$H$_4$—CH$_2$—CH$_2$-pyrimidinyl(2') | |
| 21.019. | OMe | 3-C$_6$H$_4$—CH$_2$—CH$_2$-pyrimidinyl(4') | |
| 21.020. | OMe | 3-C$_6$H$_4$—CH$_2$—CH$_2$-pyrimidinyl(5') | |
| 21.021. | OMe | 3-C$_6$H$_4$—CH$_2$—CH$_2$—I | |
| 21.022. | OMe | 3-C$_6$H$_4$—CH$_2$—CH$_2$—CH$_3$ | |
| 21.023. | OMe | 3-C$_6$H$_4$—CH$_2$—CH$_2$—Br | |
| 21.024. | OMe | 3-C$_6$H$_4$—CH$_2$—CH$_2$—C$_6$H$_4$(Br)(4') | |
| 21.025. | OMe | 3-C$_6$H$_4$—CH$_2$—CH$_2$—C$_6$H$_2$(OCH$_3$)$_3$(3',4',5') | |
| 21.026. | OMe | 3-C$_6$H$_4$—CH$_2$—CH$_2$—C$_6$H$_3$(CH$_3$)$_2$(3',5') | |
| 21.027. | OMe | 3-C$_6$H$_4$—CH$_2$—CH$_2$-thiazolyl(2') | |
| 21.028. | OMe | 3-C$_6$H$_4$—CH$_2$—CH$_2$-oxazolyl(2') | |
| 21.029. | OMe | 3-C$_6$H$_4$—CH$_2$—CH$_2$-thienyl(2') | |
| 21.030. | OMe | 3-C$_6$H$_4$—CH$_2$—CH$_2$-thienyl(3') | |
| 21.031. | OMe | 3-C$_6$H$_4$—CH$_2$—CH$_2$-Et | |
| 21.032. | OMe | 4-C$_6$H$_4$—CH$_2$—CH$_3$ | |
| 21.033. | OMe | 2-C$_6$H$_4$—CH$_2$—CH$_3$ | |
| 21.034. | OMe | 4-C$_6$H$_4$—CH$_2$—CH$_2$—CH$_3$ | |

TABLE 21-continued

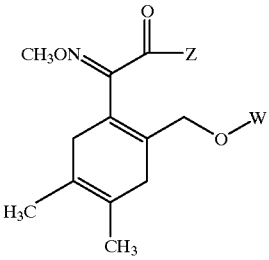

| Comp. No. | Z | W | Physical data |
|---|---|---|---|
| 21.035. | OMe | 2-C₆H₄—CH₂—CH₂—Br | |
| 21.036. | OMe | 2-C₆H₄—CH₂—CH₂—C(CH₃)₂—OH | |
| 21.037. | OMe | 4-C₆H₄—CH₂—CH₂—(CH₃)₂—OH | |
| 21.038. | OMe | 3-C₆H₄—CH₂—CH₂—CF₃ | |
| 21.039. | OMe | 3-C₆H₄—CH₂—CH₂—COOEt | |
| 21.040. | OMe | 3-C₆H₄—CH₂—CH₂—COOMe | |
| 21.041. | OMe | 2-C₆H₄—CH₂—CH₂—C(CH₃)₂—OH | |
| 21.042. | OMe | 3-C₆H₄—CH₂—CH₂—C(CH₃)₂—O—CH₃ | |
| 21.043. | OMe | 4-C₆H₄—CH₂—CH₂—C(CH₃)₂—O—CH₃ | |
| 21.044. | OMe | 3-C₆H₄—CH₂—CH₂—CH₂—OMe | |
| 21.045. | OMe | 3-C₆H₄—CH₂—CH₂—C₄H₉(n) | |
| 21.046. | OMe | 3-C₆H₄—CH₂—CH₂—C₃H₇(n) | |
| 21.047. | OMe | 3-C₆H₄—CH₂—CH₂—C₈H₁₇(n) | |
| 21.048. | NHMe | 3-C₆H₄—CH₂—CH₂—C₆H₃Cl₂(2',4') | |
| 21.049. | NHMe | 3-C₆H₄—CH₂—CH₂—C₆H₅ | |
| 21.050. | NHMe | 3-C₆H₄—CH₂—CH₂—C₆H₄(OCH₃)(4') | |
| 21.051. | NHMe | 3-C₆H₄—CH₂—CH₂—C₆H₃(CF₃)2(3',5') | |
| 21.052. | NHMe | 3-C₆H₄—CH₂—CH₂—C₆H₄(CF₃)(3') | |
| 21.053. | NHMe | 3-C₆H₄—CH₂—CH₂—CO—C₆H₄(CF₃)(3') | |
| 21.054. | NHMe | 3-C₆H₄—CH₂—CH₂—CO—C₆H₅ | |
| 21.055. | NHMe | 3-C₆H₄—CH₂—CH₂—CO—C₆H₄(Cl)(3') | |
| 21.056. | NHMe | 3-C₆H₄—CH₂—CH₂—C(CH₃)₂—OH | |
| 21.057. | NHMe | 3-C₆H₄—CH₂—CH₂-pyrazinyl(2') | |
| 21.058. | NHMe | 3-C₆H₄—CH₂—CH₂-pyridyl(3') | |
| 21.059. | NHMe | 3-C₆H₄—CH₂—CH₂—CO-pyridyl(3') | |
| 21.060. | NHMe | 3-C₆H₄—CH₂—CH₂-pyridyl(2') | |
| 21.061. | NHMe | 3-C₆H₄—CH₂—CH₂-pyridyl(4') | |
| 21.062. | NHMe | 3-C₆H₄—CH₂—CH₂—C₆H₄(CF₃)(4') | |
| 21.063. | NHMe | 3-C₆H₄—CH₂—CH₂—C₆H₄(Cl)(4') | |
| 21.064. | NHMe | 3-C₆H₄—CH₂—CH₂—CH₂—OH | |
| 21.065. | NHMe | 3-C₆H₄—CH₂—CH₂-pyrimidinyl(2') | |
| 21.066. | NHMe | 3-C₆H₄—CH₂—CH₂-pyrimidinyl(4') | |
| 21.067. | NHMe | 3-C₆H₄—CH₂—CH₂-pyrimidinyl(5') | |
| 21.068. | NHMe | 3-C₆H₄—CH₂—CH₂—I | |
| 21.069. | NHMe | 3-C₆H₄—CH₂—CH₂—CH₃ | |
| 21.070. | NHMe | 3-C₆H₄—CH₂—CH₂—Br | |
| 21.071. | NHMe | 3-C₆H₄—CH₂—CH₂—C₆H₄(Br)(4') | |
| 21.072. | NHMe | 3-C₆H₄—CH₂—CH₂—C₆H₂(OCH₃)₃(3',4',5') | |
| 21.073. | NHMe | 3-C₆H₄—CH₂—CH₂—C₆H₃(CH₃)₂(3',5') | |
| 21.074. | NHMe | 3-C₆H₄—CH₂—CH₂-thiazolyl(2') | |
| 21.075. | NHMe | 3-C₆H₄—CH₂—CH₂-oxazolyl(2') | |
| 21.076. | NHMe | 3-C₆H₄—CH₂—CH₂-thienyl(2') | |
| 21.077. | NHMe | 3-C₆H₄—CH₂—CH₂-thienyl(3') | |
| 21.078. | NHMe | 3-C₆H₄—CH₂—CH₂-Et | |
| 21.079. | NHMe | 4-C₆H₄—CH₂—CH₃ | |
| 21.080. | NHMe | 2-C₆H₄—CH₂—CH₃ | |
| 21.081. | NHMe | 4-C₆H₄—CH₂—CH₂—CH₃ | |
| 21.082. | NHMe | 2-C₆H₄—CH₂—CH₂—Br | |
| 21.083. | NHMe | 2-C₆H₄—CH₂—CH₂—C(CH₃)₂—OH | |
| 21.084. | NHMe | 4-C₆H₄—CH₂—CH₂—C(CH₃)₂—OH | |
| 21.085. | NHMe | 3-C₆H₄—CH₂—CH₂—CF₃ | |
| 21.086. | NHMe | 3-C₆H₄—CH₂—CH₂—COOEt | |
| 21.087. | NHMe | 3-C₆H₄—CH₂—CH₂—COOMe | |
| 21.088. | NHMe | 2-C₆H₄—CH₂—CH₂—C(CH₃)₂—OH | |
| 21.089. | NHMe | 3-C₆H₄—CH₂—CH₂—C(CH₃)₂—O—CH₃ | |
| 21.090. | NHMe | 4-C₆H₄—CH₂—CH₂—C(CH₃)₂—O—CH₃ | |
| 21.091. | NHMe | 3-C₆H₄—CH₂—CH₂—CH₂—OMe | |
| 21.092. | NHMe | 3-C₆H₄—CH₂—CH₂—C₄H₉(n) | |
| 21.093. | NHMe | 3-C₆H₄—CH₂—CH₂—C₃H₇(n) | |
| 21.094. | NHMe | 3-C₆H₄—CH₂—CH₂—C₈H₁₇(n) | |
| 21.095. | NHMe | 3-C₆H₄—CH₂—CH₂—C₆H₄(CH₃)(3') | |
| 21.096. | NHMe | 3-C₆H₄—CH₂—CH₂—CH₂-morpholinyl(1) | |

TABLE 21-continued

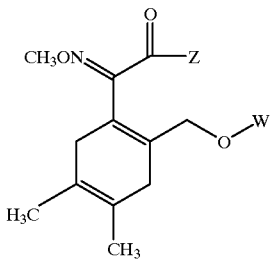

| Comp. No. | Z | W | Physical data |
|---|---|---|---|
| 21.097. | NHMe | 3-C$_6$H$_4$—CH$_2$—CH$_2$—CH$_2$-piperidinyl(1) | |
| 21.098. | NHMe | 3-C$_6$H$_4$—CH$_2$—CH$_2$—CH$_2$—Cl | |
| 21.099. | OMe | 3-C$_6$H$_4$—CH$_2$—CH$_2$—C$_6$H$_4$(CH$_3$)(3') | |
| 21.100. | NHMe | 3-C$_6$H$_4$—CH$_2$—CH$_2$—CH$_2$—O—C$_6$H$_3$(Cl$_2$)(2',4') | |
| 21.101. | NHMe | 3-C$_6$H$_4$—CH$_2$—CH$_2$—CH$_2$—O—C$_6$H$_4$(CH$_3$)(2') | |
| 21.102. | NHMe | 3-C$_6$H$_4$—CH$_2$—CH$_2$—CH$_2$—O—C$_6$H$_4$(CH$_3$)(3') | |

TABLE 21a

Compounds of the formula

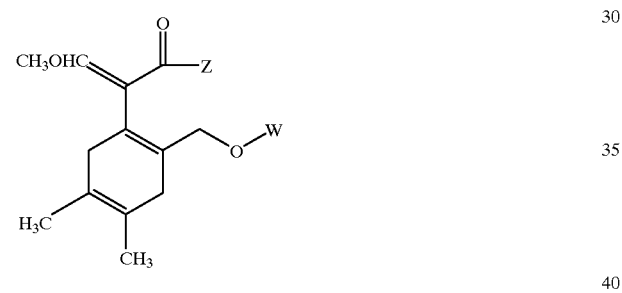

in which Z and W have the meanings of the corresponding compounds of Table 20.

TABLE 22

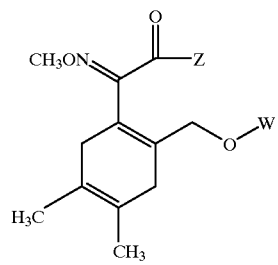

| Comp. No. | Z | W | Physical data |
|---|---|---|---|
| 22.001. | OMe | 3-C$_6$H$_4$—O—CH$_2$—C$_6$H$_3$Cl$_2$(2',4') | |
| 22.002. | OMe | 3-C$_6$H$_4$—O—CH$_2$—C$_6$H$_5$ | |
| 22.003. | OMe | 3-C$_6$H$_4$—O—CH$_2$—C$_6$H$_4$(OCH$_3$)(4') | |
| 22.004. | OMe | 3-C$_6$H$_4$—O—CH$_2$—C$_6$H$_3$(CF$_3$)(3',5') | |

TABLE 22-continued

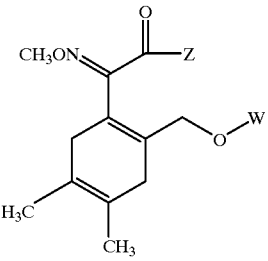

| Comp. No. | Z | W | Physical data |
|---|---|---|---|
| 22.005. | OMe | 3-$C_6H_4$—O—$CH_2$—$C_6H_4(CF_3)(3')$ | |
| 22.006. | OMe | 3-$C_6H_4$—O—$CH_2$—CO—$C_6H_4(CF_3)(3')$ | |
| 22.007. | OMe | 3-$C_6H_4$—O—$CH_2$—CO—$C_6H_5$ | |
| 22.008. | OMe | 3-$C_6H_4$—O—$CH_2$—CO—$C_6H_4(Cl)(3')$ | |
| 22.009. | OMe | 3-$C_6H_4$—O—$CH_2$—$C(CH_3)_2$—OH | |
| 22.010. | OMe | 3-$C_6H_4$—O—$CH_2$-pyrazinyl(2') | |
| 22.011. | OMe | 3-$C_6H_4$—O—$CH_2$-pyridyl(3') | |
| 22.012. | OMe | 3-$C_6H_4$—O—$CH_2$—CO-pyridyl(3') | |
| 22.013. | OMe | 3-$C_6H_4$—O—$CH_2$-pyridyl(2') | |
| 22.014. | OMe | 3-$C_6H_4$—O—$CH_2$-pyridyl(4') | |
| 22.015. | OMe | 3-$C_6H_4$—O—$CH_2$—$C_6H_4(CF_3)(4')$ | |
| 22.016. | OMe | 3-$C_6H_4$—O—$CH_2$—$C_6H_4(Cl)(4')$ | |
| 22.017. | OMe | 3-$C_6H_4$—O—$CH_2$—OH | |
| 22.018. | OMe | 3-$C_6H_4$—O—$CH_2$-pyrimidinyl(2') | |
| 22.019. | OMe | 3-$C_6H_4$—O—$CH_2$-pyrimidinyl(4') | |
| 22.020. | OMe | 3-$C_6H_4$—O—$CH_2$-pyrimidinyl(5') | |
| 22.021. | OMe | 3-$C_6H_4$—O—$CH_2$—I | |
| 22.022. | OMe | 3-$C_6H_4$—O—$CH_2$—$CH_3$ | |
| 22.023. | OMe | 3-$C_6H_4$—O—$CH_2$—Br | |
| 22.024. | OMe | 3-$C_6H_4$—O—$CH_2$—$C_6H_4(Br)(4')$ | |
| 22.025. | OMe | 3-$C_6H_4$—O—$CH_2$—$C_6H_2(OCH_3)_3(3',4',5')$ | |
| 22.026. | OMe | 3-$C_6H_4$—O—$CH_2$—$C_6H_3(CH_3)_2(3',5')$ | |
| 22.027. | OMe | 3-$C_6H_4$—O—$CH_2$-thiazolyl(2') | |
| 22.028. | OMe | 3-$C_6H_4$—O—$CH_2$-oxazolyl(2') | |
| 22.029. | OMe | 3-$C_6H_4$—O—$CH_2$-thienyl(2') | |
| 22.030. | OMe | 3-$C_6H_4$—O—$CH_2$-thienyl(3') | |
| 22.031. | OMe | 3-$C_6H_4$—O—$CH_2$-Et | |
| 22.032. | OMe | 4-$C_6H_4$—O—$CH_3$ | |
| 22.033. | OMe | 2-$C_6H_4$—O—$CH_3$ | |
| 22.034. | OMe | 4-$C_6H_4$—O—$CH_2$—$CH_3$ | |
| 22.035. | OMe | 2-$C_6H_4$—O—$CH_2$—Br | |
| 22.036. | OMe | 2-$C_6H_4$—O—$CH_2$—$C(CH_3)_2$—OH | |
| 22.037. | OMe | 4-$C_6H_4$—O—$CH_2$—$(CH_3)_2$—OH | |
| 22.038. | OMe | 3-$C_6H_4$—O—$CH_2$—$CF_3$ | |
| 22.039. | OMe | 3-$C_6H_4$—O—$CH_2$—COOEt | |
| 22.040. | OMe | 3-$C_6H_4$—O—$CH_2$—COOMe | |
| 22.041. | OMe | 2-$C_6H_4$—O—$CH_2$—$C(CH_3)_2$—OH | |
| 22.042. | OMe | 3-$C_6H_4$—O—$CH_2$—$C(CH_3)2$—O—$CH_3$ | |
| 22.043. | OMe | 4-$C_6H_4$—O—$CH_2$—$C(CH_3)2$—O—$CH_3$ | |
| 22.044. | OMe | 3-$C_6H_4$—O—$CH_2$—$CH_2$—OMe | |
| 22.045. | OMe | 3-$C_6H_4$—O—$CH_2$—$C_4H_9(n)$ | |
| 22.046. | OMe | 3-$C_6H_4$—O—$CH_2$—$C_3H_7(n)$ | |
| 22.047. | OMe | 3-$C_6H_4$—O—$CH_2$—$C_8H_{17}(n)$ | |
| 22.048. | NHMe | 3-$C_6H_4$—O—$CH_2$—$C_6H_3Cl_2(2',4')$ | |
| 22.049. | NHMe | 3-$C_6H_4$—O—$CH_2$—$C_6H_5$ | |
| 22.050. | NHMe | 3-$C_6H_4$—O—$CH_2$—$C_6H_4(OCH_3)(4')$ | |
| 22.051. | NHMe | 3-$C_6H_4$—O—$CH_2$—$C_6H_3(CF_3)_2(3',5')$ | |
| 22.052. | NHMe | 3-$C_6H_4$—O—$CH_2$—$C_6H_4(CF_3)(3')$ | |
| 22.053. | NHMe | 3-$C_6H_4$—O—$CH_2$—CO—$C_6H_4(CF_3)(3')$ | |
| 22.054. | NHMe | 3-$C_6H_4$—O—$CH_2$—CO—$C_6H_5$ | |
| 22.055. | NHMe | 3-$C_6H_4$—O—$CH_2$—CO—$C_6H_4(Cl)(3')$ | |
| 22.056. | NHMe | 3-$C_6H_4$—O—$CH_2$—$C(CH_3)_2$—OH | |
| 22.057. | NHMe | 3-$C_6H_4$—O—$CH_2$-pyrazinyl(2') | |
| 22.058. | NHMe | 3-$C_6H_4$—O—$CH_2$-pyridyl(3') | |
| 22.059. | NHMe | 3-$C_6H_4$—O—$CH_2$—CO-pyridyl(3') | |
| 22.060. | NHMe | 3-$C_6H_4$—O—$CH_2$-pyridyl(2') | |
| 22.061. | NHMe | 3-$C_6H_4$—O—$CH_2$-pyridyl(4') | |
| 22.062. | NHMe | 3-$C_6H_4$—O—$CH_2$—$C_6H_4(CF_3)(4')$ | |
| 22.063. | NHMe | 3-$C_6H_4$—O—$CH_2$—$C_6H_4(Cl)(4')$ | |
| 22.064. | NHMe | 3-$C_6H_4$—O—$CH_2$—OH | |
| 22.065. | NHMe | 3-$C_6H_4$—O—$CH_2$-pyrimidinyl(2') | |

TABLE 22-continued

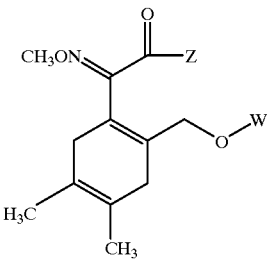

| Comp. No. | Z | W | Physical data |
|---|---|---|---|
| 22.066. | NHMe | 3-C$_6$H$_4$—O—CH$_2$-pyrimidinyl(4') | |
| 22.067. | NHMe | 3-C$_6$H$_4$—O—CH$_2$-pyrimidinyl(5') | |
| 22.068. | NHMe | 3-C$_6$H$_4$—O—CH$_2$—I | |
| 22.069. | NHMe | 3-C$_6$H$_4$—O—CH$_2$—CH$_3$ | |
| 22.070. | NHMe | 3-C$_6$H$_4$—O—CH$_2$—Br | |
| 22.071. | NHMe | 3-C$_6$H$_4$—O—CH$_2$—C$_6$H$_4$(Br)(4') | |
| 22.072. | NHMe | 3-C$_6$H$_4$—O—CH$_2$—C$_6$H$_2$(OCH$_3$)$_3$(3',4',5') | |
| 22.073. | NHMe | 3-C$_6$H$_4$—O—CH$_2$—C$_6$H$_3$(CH$_3$)$_2$(3',5') | |
| 22.074. | NHMe | 3-C$_6$H$_4$—O—CH$_2$-thiazolyl(2') | |
| 22.075. | NHMe | 3-C$_6$H$_4$—O—CH$_2$-oxazolyl(2') | |
| 22.076. | NHMe | 3-C$_6$H$_4$—O—CH$_2$-thienyl(2') | |
| 22.077. | NHMe | 3-C$_6$H$_4$—O—CH$_2$-thienyl(3') | |
| 22.078. | NHMe | 3-C$_6$H$_4$—O—CH$_2$-Et | |
| 22.079. | NHMe | 4-C$_6$H$_4$—O—CH$_3$ | |
| 22.080. | NHMe | 2-C$_6$H$_4$—O—CH$_3$ | |
| 22.081. | NHMe | 4-C$_6$H$_4$—O—CH$_2$—CH$_3$ | |
| 22.082. | NHMe | 2-C$_6$H$_4$—O—CH$_2$—Br | |
| 22.083. | NHMe | 2-C$_6$H$_4$—O—CH$_2$—C(CH$_3$)$_2$—OH | |
| 22.084. | NHMe | 4-C$_6$H$_4$—O—CH$_2$—C(CH$_3$)$_2$—OH | |
| 22.085. | NHMe | 3-C$_6$H$_4$—O—CH$_2$—CF$_3$ | |
| 22.086. | NHMe | 3-C$_6$H$_4$—O—CH$_2$—COOEt | |
| 22.087. | NHMe | 3-C$_6$H$_4$—O—CH$_2$—COOMe | |
| 22.088. | NHMe | 2-C$_6$H$_4$—O—CH$_2$—C(CH$_3$)$_2$—OH | |
| 22.089. | NHMe | 3-C$_6$H$_4$—O—CH$_2$—C(CH$_3$)2—O—CH$_3$ | |
| 22.090. | NHMe | 4-C$_6$H$_4$—O—CH$_2$—C(CH$_3$)2—O—CH$_3$ | |
| 22.091. | NHMe | 3-C$_6$H$_4$—O—CH$_2$—CH$_2$—OMe | |
| 22.092. | NHMe | 3-C$_6$H$_4$—O—CH$_2$—C$_4$H$_9$(n) | |
| 22.093. | NHMe | 3-C$_6$H$_4$—O—CH$_2$—C$_3$H$_7$(n) | |
| 22.094. | NHMe | 3-C$_6$H$_4$—O—CH$_2$—C$_8$H$_{17}$(n) | |
| 22.095. | NHMe | 3-C$_6$H$_4$—O—CH$_2$—C$_6$H$_4$(CH$_3$)(3') | |
| 22.096. | NHMe | 3-C$_6$H$_4$—O—CH$_2$—CH$_2$-morpholinyl(1) | |
| 22.097 | NHMe | 3-C$_6$H$_4$—O—CH$_2$—CH$_2$-piperidinyl(1) | |
| 22.098. | NHMe | 3-C$_6$H$_4$—O—CH$_2$—CH$_2$—Cl | |
| 22.099. | OMe | 3-C$_6$H$_4$—O—CH$_2$—C$_6$H$_4$(CH$_3$)(3') | |
| 22.100. | NHMe | 3-C$_6$H$_4$—O—CH$_2$—CH$_2$—O—C$_6$H$_3$(Cl$_2$)(2',4') | |
| 22.101. | NHMe | 3-C$_6$H$_4$—O—CH$_2$—CH$_2$—O—C$_6$H$_4$(CH$_3$)(2') | |
| 22.102. | NHMe | 3-C$_6$H$_4$—O—CH$_2$—CH$_2$—O—C$_6$H$_4$(CH$_3$)(3') | |
| 22.103. | OMe | 3-C$_6$H$_4$—O—C$_6$H$_2$CN(2')(CH$_3$)(4',5') | resin |
| 22.104. | OMe | 3-C$_6$H$_4$—O—CH$_2$—C≡C—C$_6$H$_5$ | oil |
| 22.105. | OMe | 3-C$_6$H$_4$—O—CH$_2$—C≡C—C$_6$H$_4$(CH$_3$)(3') | oil |
| 22.106. | OMe | 3-C$_6$H$_4$—O—CH$_2$—CH$_2$—CH$_2$—C$_6$H$_5$ | oil |
| 22.107. | OMe | 3-C$_6$H$_4$—O—CH$_2$—CH$_2$—CH$_2$—C$_6$H$_4$(CH$_3$)(3') | resin |
| 22.108. | OMe | 3-C$_6$H$_4$—O—CH$_2$-pyridin-5'-yl(Cl)(2') | |
| 22.109. | OMe | 3-C$_6$H$_4$—O—CH$_2$-thiazol-5'-yl(Cl)(2') | |
| 22.110. | OMe | 3-C$_6$H$_4$—O—CH$_2$-thiazol-5'-yl | |
| 22.111. | OMe | 3-C$_6$H$_4$—O—CH$_2$-thiadiazol-5'-yl | |
| 22.112. | OMe | 3-C$_6$H$_4$—O—CH$_2$—C$_6$H$_4$NO$_2$(2') | |
| 22.113. | OMe | 3-C$_6$H$_4$—O—CH$_2$—C$_6$H$_4$NO$_2$(4') | |
| 22.114. | OMe | 3-C$_6$H$_4$—O—CH$_2$—C$_6$H$_4$Cl(2') | |
| 22.115. | OMe | 3-C$_6$H$_4$—O—CH$_2$—C$_6$H$_3$(CH$_3$)$_2$(3',4') | |
| 22.116. | OMe | 3-C$_6$H$_4$—O—CH$_2$—C$_6$H$_4$CF$_3$(2') | |
| 22.117. | OMe | 3-C$_6$H$_4$—O—CH$_2$-(3',4'-dimethylcyclohexa-1,4-dienyl) | resin |

TABLE 22a

Compounds of the formula

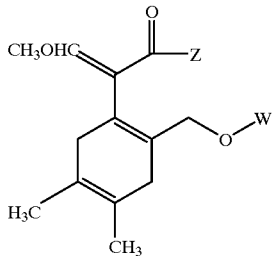

in which Z and W have the meanings of the corresponding compounds of Table 22.

TABLE 23

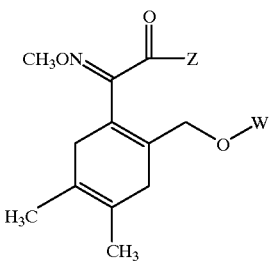

| Comp. No. | Z | W | Physical data |
|---|---|---|---|
| 23.001. | OMe | 3-C$_6$H$_4$—O—C$_6$H$_3$Cl$_2$(2',4') | |
| 23.002. | OMe | 3-C$_6$H$_4$—O—C$_6$H$_5$ | |
| 23.003. | OMe | 3-C$_6$H$_4$—O—C$_6$H$_4$(OCH$_3$)(4') | |
| 23.004. | OMe | 3-C$_6$H$_4$—O—C$_6$H$_3$(CF$_3$)$_2$(3',5') | |
| 23.005. | OMe | 3-C$_6$H$_4$—O—C$_6$H$_4$(CF$_3$)(3') | |
| 23.006. | OMe | 3-C$_6$H$_4$—O—CO—C$_6$H$_4$(CF$_3$)(3') | |
| 23.007. | OMe | 3-C$_6$H$_4$—O—CO—C$_6$H$_5$ | |
| 23.008. | OMe | 3-C$_6$H$_4$—O—CO—C$_6$H$_4$(Cl)(3') | |
| 23.009. | OMe | 3-C$_6$H$_4$—O—C$_6$H$_3$(CN)(3')(NO$_2$)(4') | |
| 23.010. | OMe | 3-C$_6$H$_4$—O-pyrazinyl(2') | |
| 23.011. | OMe | 3-C$_6$H$_4$—O-pyridyl(3') | |
| 23.012. | OMe | 3-C$_6$H$_4$—O—CO-pyridyl(3') | |
| 23.013. | OMe | 3-C$_6$H$_4$—O-pyridyl(2') | |
| 23.014. | OMe | 3-C$_6$H$_4$—O-pyridyl(4') | |
| 23.015. | OMe | 3-C$_6$H$_4$—O—C$_6$H$_4$(CF$_3$)(4') | |
| 23.016. | OMe | 3-C$_6$H$_4$—O—C$_6$H$_4$(Cl)(4') | |
| 23.017. | OMe | 3-C$_6$H$_4$—O—C$_6$H$_4$(NO$_2$)(4') | |
| 23.018. | OMe | 3-C$_6$H$_4$—O-pyrimidinyl(2') | |
| 23.019. | OMe | 3-C$_6$H$_4$—O-pyrimidinyl(4') | |
| 23.020. | OMe | 3-C$_6$H$_4$—O-pyrimidinyl(5') | |
| 23.021. | OMe | 3-C$_6$H$_4$—O—CO—NH—C$_6$H$_4$(OMe)(4') | |
| 23.022. | OMe | 3-C$_6$H$_4$—O—CH$_3$ | |
| 23.023. | OMe | 3-C$_6$H$_4$—O—CO—NH—C$_6$H$_4$(CF$_3$)(3') | |
| 23.024. | OMe | 3-C$_6$H$_4$—O—C$_6$H$_4$(Br)(4') | |
| 23.025. | OMe | 3-C$_6$H$_4$—O—C$_6$H$_2$(OCH$_3$)$_3$(3',4',5') | |
| 23.026. | OMe | 3-C$_6$H$_4$—O—C$_6$H$_3$(CH$_3$)$_2$(3',5') | |
| 23.027. | OMe | 3-C$_6$H$_4$—O-thiazoyl(2') | |
| 23.028. | OMe | 3-C$_6$H$_4$—O-oxazolyl(2') | |
| 23.029. | OMe | 3-C$_6$H$_4$—O-thienyl(2') | |
| 23.030. | OMe | 3-C$_6$H$_4$—O-thienyl(3') | |
| 23.031. | OMe | 3-C$_6$H$_4$—O-Et | |
| 23.032. | OMe | 3-C$_6$H$_4$—O—H | |
| 23.033. | OMe | 3-C$_6$H$_4$—O—H | |
| 23.034. | OMe | 3-C$_6$H$_4$—O—CH$_3$ | |
| 23.035. | OMe | 3-C$_6$H$_4$—O—CO—NH—C$_6$H$_4$(Cl)(4') | |
| 23.036. | OMe | 3-C$_6$H$_4$—O—CO—NH—C$_6$H$_3$(Cl$_2$)(2',4') | |
| 23.037. | OMe | 3-C$_6$H$_4$—O—CO—NH—C$_6$H$_4$(NO$_2$)(4') | |
| 23.038. | OMe | 3-C$_6$H$_4$—O—CF$_3$ | |
| 23.039. | OMe | 3-C$_6$H$_4$—O—COOEt | |

TABLE 23-continued

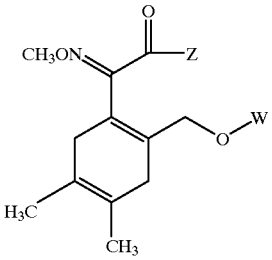

| Comp. No. | Z | W | Physical data |
|---|---|---|---|
| 23.040. | OMe | 3-C$_6$H$_4$—O—COOMe | |
| 23.041. | OMe | 3-C$_6$H$_4$—O—CO—NH—C$_6$H$_4$—(Br)(4') | |
| 23.042. | OMe | 3-C$_6$H$_4$—O—CO—NH—C$_6$H$_4$—(I)(4') | |
| 23.043. | OMe | 3-C$_6$H$_4$—O—CO—NH—C$_6$H$_4$—(CH$_3$)(2') | |
| 23.044. | OMe | 3-C$_6$H$_4$—O—CH$_2$—OMe | |
| 23.045. | OMe | 3-C$_6$H$_4$—O—C$_4$H$_9$(n) | |
| 23.046. | OMe | 3-C$_6$H$_4$—O—C$_3$H$_7$(n) | |
| 23.047. | OMe | 3-C$_6$H$_4$—O—C$_8$H$_{17}$(n) | |
| 23.048. | NHMe | 3-C$_6$H$_4$—O—C$_6$H$_3$Cl$_2$(2',4') | |
| 23.049. | NHMe | 3-C$_6$H$_4$—O—C$_6$H$_5$ | |
| 23.050. | NHMe | 3-C$_6$H$_4$—O—C$_6$H$_4$(OCH$_3$)(4') | |
| 23.051. | NHMe | 3-C$_6$H$_4$—O—C$_6$H$_3$(CF$_3$)$_2$(3',5') | |
| 23.052. | NHMe | 3-C$_6$H$_4$—O—C$_6$H$_4$(CF$_3$)(3') | |
| 23.053. | NHMe | 3-C$_6$H$_4$—O—CO—C$_6$H$_4$(CF$_3$)(3') | |
| 23.054. | NHMe | 3-C$_6$H$_4$—O—CO—C$_6$H$_5$ | |
| 23.055. | NHMe | 3-C$_6$H$_4$—O—CO—C$_6$H$_4$(Cl)(3') | |
| 23.056. | OMe | 3-C$_6$H$_4$—O—CO—NH—C$_6$H$_3$—(CH$_3$)$_2$(2',6') | |
| 23.057. | NHMe | 3-C$_6$H$_4$—O-pyrazinyl(2') | |
| 23.058. | NHMe | 3-C$_6$H$_4$—O-pyridyl(3') | |
| 23.059. | NHMe | 3-C$_6$H$_4$—O—CO-pyridyl(3') | |
| 23.060. | NHMe | 3-C$_6$H$_4$—O-pyridyl(2') | |
| 23.061. | NHMe | 3-C$_6$H$_4$—O-pyridyl(4') | |
| 23.062. | NHMe | 3-C$_6$H$_4$—O—C$_6$H$_4$(CF$_3$)(4') | |
| 23.063. | NHMe | 3-C$_6$H$_4$—O—C$_6$H$_4$(Cl)(4') | |
| 23.064. | OMe | 3-C$_6$H$_4$—O—CO—NH—C$_6$H$_3$-(Me)(2')(Et)(6') | |
| 23.065. | NHMe | 3-C$_6$H$_4$—O-pyrimidinyl(2') | |
| 23.066. | NHMe | 3-C$_6$H$_4$—O-pyrimidinyl(4') | |
| 23.067. | NHMe | 3-C$_6$H$_4$—O-pyrimidinyl(5') | |
| 23.068. | OMe | 3-C$_6$H$_4$—O—CO—NH—C$_6$H$_3$-(Me)$_2$(2',4') | |
| 23.069. | NHMe | 3-C$_6$H$_4$—O—CH$_3$ | |
| 23.070. | OMe | 3-C$_6$H$_4$—O—CO—NH—C$_6$H$_4$—(Cl)(3') | |
| 23.071. | NHMe | 3-C$_6$H$_4$—O—C$_6$H$_4$(Br)(4') | |
| 23.072. | NHMe | 3-C$_6$H$_4$—O—C$_6$H$_2$(OCH$_3$)$_3$(3',4',5') | |
| 23.073. | NHMe | 3-C$_6$H$_4$—O—C$_6$H$_3$(CH$_3$)$_2$(3',5') | |
| 23.074. | NHMe | 3-C$_6$H$_4$—O-thiazolyl(2') | |
| 23.075. | NHMe | 3-C$_6$H$_4$—O-oxazolyl(2') | |
| 23.076. | NHMe | 3-C$_6$H$_4$—O-thienyl(2') | |
| 23.077. | NHMe | 3-C$_6$H$_4$—O-thienyl(3') | |
| 23.078. | NHMe | 3-C$_6$H$_4$—O-Et | |
| 23.079. | NHMe | 3-C$_6$H$_4$—O—CH$_3$ | |
| 23.080. | NHMe | 3-C$_6$H$_4$—O—CH$_3$ | |
| 23.081. | NHMe | 3-C$_6$H$_4$—O—CH$_3$ | |
| 23.082. | OMe | 3-C$_6$H$_4$—O—CO—NH—C$_6$H$_4$—(Cl)(2') | |
| 23.083. | OMe | 3-C$_6$H$_4$—O—CO—NH—C$_6$H$_3$—(Cl)$_2$(3',5') | |
| 23.084. | OMe | 3-C$_6$H$_4$—O—CO—NH—C$_6$H$_3$—(CF$_3$)$_2$(3',5') | |
| 23.085. | NHMe | 3-C$_6$H$_4$—O—CF$_3$ | |
| 23.086. | NHMe | 3-C$_6$H$_4$—O—COOEt | |
| 23.087. | NHMe | 3-C$_6$H$_4$—O—COOMe | |
| 23.088. | OMe | 3-C$_6$H$_4$—O—CO—NH—C$_6$H$_4$—(CF$_3$)(4') | |
| 23.089. | OMe | 3-C$_6$H$_4$—O—CO—NH—C$_6$H$_4$—(OCH$_3$)(4') | |
| 23.090. | OMe | 3-C$_6$H$_4$—O—CO—NH—C$_6$H$_4$—(OCF$_3$)(4') | |
| 23.091. | NHMe | 3-C$_6$H$_4$—O—CH$_2$—OMe | |
| 23.092. | NHMe | 3-C$_6$H$_4$—O—C$_4$H$_9$(n) | |
| 23.093. | NHMe | 3-C$_6$H$_4$—O—C$_3$H$_7$(n) | |
| 23.094. | NHMe | 3-C$_6$H$_4$—O—C$_8$H$_{17}$(n) | |
| 23.095. | NHMe | 3-C$_6$H$_4$—O—C$_6$H$_4$(CH$_3$)(3') | |
| 23.096. | NHMe | 3-C$_6$H$_4$—O—CH$_2$-morpholinyl(1) | |
| 23.097. | NHMe | 3-C$_6$H$_4$—O—CH$_2$-piperidinyl(1) | |
| 23.098. | NHMe | 3-C$_6$H$_4$—O—CH$_2$—Cl | |

TABLE 23-continued

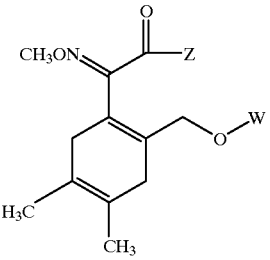

| Comp. No. | Z | W | Physical data |
|---|---|---|---|
| 23.099. | OMe | 3-C$_6$H$_4$—O—C$_6$H$_4$(CH$_3$)(3') | |
| 23.100 | NHMe | 3-C$_6$H$_4$—O—CH$_2$—O—C$_6$H$_3$(Cl$_2$)(2',4') | |
| 23.101. | NHMe | 3-C$_6$H$_4$—O—CH$_2$—O—C$_6$H$_4$(CH$_3$)(2') | |
| 23.102. | NHMe | 3-C$_6$H$_4$—O—CH$_2$—O—C$_6$H$_4$(CH$_3$)(3') | |

TABLE 24

Compounds 24.001–24.102, in which Z and W have the meanings of the corresponding compounds of Table 23, W being substituted in the 4-position. Physical data of selected compounds

| Comp. No. | X | R$_{21}$ | R$_{22}$ | Z | W | Physical data |
|---|---|---|---|---|---|---|
| 24.003. | N | Me | Me | OMe | 4-C$_6$H$_4$—O—C$_6$H$_4$(OCH$_3$)(4') | oil |
| 24.015. | N | Me | Me | OMe | 4-C$_6$H$_4$—O—C$_6$H$_4$(CF$_3$)(4') | oil |

TABLE 25

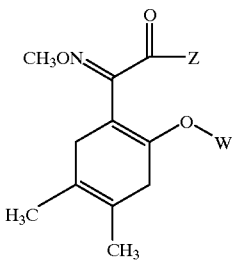

| Comp. No. | Z | W | Physical data |
|---|---|---|---|
| 25.001. | OMe | 3-C$_6$H$_4$—O—C$_6$H$_3$Cl$_2$(2',4') | |
| 25.002. | OMe | 3-C$_6$H$_4$—O—C$_6$H$_5$ | |
| 25.003. | OMe | 3-C$_6$H$_4$—O—C$_6$H$_4$(OCH$_3$)(4') | |
| 25.004. | OMe | 3-C$_6$H$_4$—O—C$_6$H$_3$(CF$_3$)$_2$(3',5') | |
| 25.005. | OMe | 3-C$_6$H$_4$—O—C$_6$H$_4$(CF$_3$)(3') | |
| 25.006. | OMe | 3-C$_6$H$_4$—O—CO—C$_6$H$_4$(CF$_3$)(3') | |
| 25.007. | OMe | 3-C$_6$H$_4$—O—CO—C$_6$H$_5$ | |
| 25.008. | OMe | 3-C$_6$H$_4$—O—CO—C$_6$H$_4$(Cl)(3') | |
| 25.009. | OMe | 3-C$_6$H$_4$—O—C$_6$H$_3$(CN)(3')(NO$_2$)(4') | |
| 25.010. | OMe | 3-C$_6$H$_4$—O-pyrazinyl(2') | |
| 25.011. | OMe | 3-C$_6$H$_4$—O-pyridyl(3') | |
| 25.012. | OMe | 3-C$_6$H$_4$—O—CO-pyridyl(3') | |
| 25.013. | OMe | 3-C$_6$H$_4$—O-pyridyl(2') | |
| 25.014. | OMe | 3-C$_6$H$_4$—O-pyridyl(4') | |
| 25.015. | OMe | 3-C$_6$H$_4$—O—C$_6$H$_4$(CF$_3$)(4') | |
| 25.016. | OMe | 3-C$_6$H$_4$—O—C$_6$H$_4$(Cl)(4') | |
| 25.017. | OMe | 3-C$_6$H$_4$—O—C$_6$H$_4$(NO$_2$)(4') | |
| 25.018. | OMe | 3-C$_6$H$_4$—O-pyrimidinyl(2') | |
| 25.019. | OMe | 3-C$_6$H$_4$—O-pyrimidinyl(4') | |

TABLE 25-continued

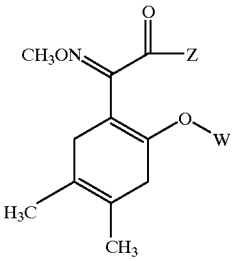

| Comp. No. | Z | W | Physical data |
|---|---|---|---|
| 25.020. | OMe | 3-C$_6$H$_4$—O-pyrimidinyl(5') | |
| 25.021. | OMe | 3-C$_6$H$_4$—O—CO—NH—C$_6$H$_4$—(OMe)(4') | |
| 25.022. | OMe | 3-C$_6$H$_4$—O—CH$_3$ | |
| 25.023. | OMe | 3-C$_6$H$_4$—O—CO—NH—C$_6$H$_4$—(CF$_3$)(3') | |
| 25.024. | OMe | 3-C$_6$H$_4$—O—C$_6$H$_4$(Br)(4') | |
| 25.025. | OMe | 3-C$_6$H$_4$—O—C$_6$H$_2$(OCH$_3$)$_3$(3',4',5') | |
| 25.026. | OMe | 3-C$_6$H$_4$—O—C$_6$H$_3$(CH$_3$)$_2$(3',5') | |
| 25.027. | OMe | 3-C$_6$H$_4$—O-thiazolyl(2') | |
| 25.028. | OMe | 3-C$_6$H$_4$—O-oxazolyl(2') | |
| 25.029. | OMe | 3-C$_6$H$_4$—O-thienyl(2') | |
| 25.030. | OMe | 3-C$_6$H$_4$—O-thienyl(3') | |
| 25.031. | OMe | 3-C$_6$H$_4$—O-Et | |
| 25.032. | OMe | 4-C$_6$H$_4$—O—H | |
| 25.033. | OMe | 2-C$_6$H$_4$—O—H | |
| 25.034. | OMe | 4-C$_6$H$_4$—O—CH$_3$ | |
| 25.035. | OMe | 3-C$_6$H$_4$—O—CO—NH—C$_6$H$_4$—(Cl)(4') | |
| 25.036. | OMe | 3-C$_6$H$_4$—O—CO—NH—C$_6$H$_3$—(Cl$_2$)(2',4') | |
| 25.037. | OMe | 3-C$_6$H$_4$—O—CO—NH—C$_6$H$_4$—(NO$_2$)(4') | |
| 25.038. | OMe | 3-C$_6$H$_4$—O—CF$_3$ | |
| 25.039. | OMe | 3-C$_6$H$_4$—O—COOEt | |
| 25.040. | OMe | 3-C$_6$H$_4$—O—COOMe | |
| 25.041. | OMe | 3-C$_6$H$_4$—O—CO—NH—C$_6$H$_4$—(Br)(4') | |
| 25.042. | OMe | 3-C$_6$H$_4$—O—CO—NH—C$_6$H$_4$—(I)(4') | |
| 25.043. | OMe | 3#C$_6$H$_4$—O—CO—NH—C$_6$H$_4$—(CH$_3$)(2') | |
| 25.044. | OMe | 3-C$_6$H$_4$—O—CH$_2$—OMe | |
| 25.045. | OMe | 3-C$_6$H$_4$—O—C$_4$H$_9$(n) | |
| 25.046. | OMe | 3-C$_6$H$_4$—O—C$_3$H$_7$(n) | |
| 25.047. | OMe | 3-C$_6$H$_4$—O—C$_8$H$_{17}$(n) | |
| 25.048. | NHMe | 3-C$_6$H$_4$—O—C$_6$H$_3$Cl$_2$(2',4') | |
| 25.049. | NHMe | 3-C$_6$H$_4$—O—C$_6$H$_5$ | |
| 25.050. | NHMe | 3-C$_6$H$_4$—O—C$_6$H$_4$(OCH$_3$)(4') | |
| 25.051. | NHMe | 3-C$_6$H$_4$—O—C$_6$H$_3$(CF$_3$)$_2$(3',5') | |
| 25.052. | NHMe | 3-C$_6$H$_4$—O—C$_6$H$_4$(CF$_3$)(3') | |
| 25.053. | NHMe | 3-C$_6$H$_4$—O—CO—C$_6$H$_4$(CF$_3$)(3') | |
| 25.054. | NHMe | 3-C$_6$H$_4$—O—CO—C$_6$H$_5$ | |
| 25.055. | NHMe | 3-C$_6$H$_4$—O—CO—C$_6$H$_4$(Cl)(3') | |
| 25.056. | OMe | 3-C$_6$H$_4$—O—CO—NH—C$_6$H$_3$—(CH$_3$)$_2$(2',6') | |
| 25.057. | NHMe | 3-C$_6$H$_4$—O-pyrazinyl(2') | |
| 25.058. | NHMe | 3-C$_6$H$_4$—O-pyridyl(3') | |
| 25.059. | NHMe | 3-C$_6$H$_4$—O—CO-pyridyl(3') | |
| 25.060. | NHMe | 3-C$_6$H$_4$—O-pyridyl(2') | |
| 25.061. | NHMe | 3-C$_6$H$_4$—O-pyridyl(4') | |
| 25.062. | NHMe | 3-C$_6$H$_4$—O—C$_6$H$_4$(CF$_3$)(4') | |
| 25.063. | NHMe | 3-C$_6$H$_4$—O—C$_6$H$_4$(Cl)(4') | |
| 25.064. | OMe | 3-C$_6$H$_4$—O—CO—NH—C$_6$H$_3$-(Me)(2')(Et)(6') | |
| 25.065. | NHMe | 3-C$_6$H$_4$—O-pyrimidinyl(2') | |
| 25.066. | NHMe | 3-C$_6$H$_4$—O-pyrimidinyl(4') | |
| 25.067. | NHMe | 3-C$_6$H$_4$—O-pyrimidinyl(5') | |
| 25.068. | OMe | 3-C$_6$H$_4$—O—CO—NH—C$_6$H$_3$-(Me)$_2$(2',4') | |
| 25.069. | NHMe | 3-C$_6$H$_4$—O—CH$_3$ | |
| 25.070. | OMe | 3-C$_6$H$_4$—O—CO—NH—C$_6$H$_4$—(Cl)(3') | |
| 25.071. | NHMe | 3-C$_6$H$_4$—O—C$_6$H$_4$(Br)(4') | |
| 25.072. | NHMe | 3-C$_6$H$_4$—O—C$_6$H$_2$(OCH$_3$)$_3$(3',4',5') | |
| 25.073. | NHMe | 3-C$_6$H$_4$—O—C$_6$H$_3$(CH$_3$)$_2$(3',5') | |
| 25.074. | NHMe | 3-C$_6$H$_4$—O-thiazolyl(2') | |
| 25.075. | NHMe | 3-C$_6$H$_4$—O-oxazolyl(2') | |
| 25.076. | NHMe | 3-C$_6$H$_4$—O-thienyl(2') | |
| 25.077. | NHMe | 3-C$_6$H$_4$—O-thienyl(3') | |
| 25.078. | NHMe | 3-C$_6$H$_4$—O-Et | |

TABLE 25-continued

Comp. No. | Z | W | Physical data
--- | --- | --- | ---
25.079. | NHMe | 4-$C_6H_4$—O—$CH_3$ |
25.080. | NHMe | 2-$C_6H_4$—O—$CH_3$ |
25.081. | NHMe | 4-$C_6H_4$—O—$CH_3$ |
25.082. | OMe | 3-$C_6H_4$—O—CO—NH—$C_6H_4$—(Cl)(2') |
25.083. | OMe | 3-$C_6H_4$—O—CO—NH—$C_6H_3$—(Cl)$_2$(3',5') |
25.084. | OMe | 3-$C_6H_4$—O—CO—NH—$C_6H_3$—($CF_3$)$_2$(3',5') |
25.085. | NHMe | 3-$C_6H_4$—O—$CF_3$ |
25.086. | NHMe | 3-$C_6H_4$—O—COOEt |
25.087. | NHMe | 3-$C_6H_4$—O—COOMe |
25.088. | OMe | 3-$C_6H_4$—O—CO—NH—$C_6H_4$—($CF_3$)(4') |
25.089. | OMe | 3-$C_6H_4$—O—CO—NH—$C_6H_4$—($OCH_3$)(4') |
25.090. | OMe | 3-$C_6H_4$—O—CO—NH—$C_6H_4$—($OCF_3$)(4') |
25.091. | NHMe | 3-$C_6H_4$—O—$CH_2$—OMe |
25.092. | NHMe | 3-$C_6H_4$—O—$C_4H_9$(n) |
25.093. | NHMe | 3-$C_6H_4$—O—$C_3H_7$(n) |
25.094. | NHMe | 3-$C_6H_4$—O—$C_8H_{17}$(n) |
25.095. | NHMe | 3-$C_6H_4$—O—$C_6H_4$($CH_3$)(3') |
25.096. | NHMe | 3-$C_6H_4$—O—$CH_2$-morpholinyl(1) |
25.097. | NHMe | 3-$C_6H_4$—O—$CH_2$-piperidinyl(1) |
25.098. | NHMe | 3-$C_6H_4$—O—$CH_2$—Cl |
25.099. | OMe | 3-$C_6H_4$—O—$C_6H_4$($CH_3$)(3') |
25.100. | NHMe | 3-$C_6H_4$—O—$CH_2$—$C_6H_3$($Cl_2$)(2',4') |
25.101. | NHMe | 3-$C_6H_4$—O—$CH_2$—$C_6H_4$($CH_3$)(2') |
25.102. | NHMe | 3-$C_6H_4$—O—$CH_2$—$C_6H_4$($CH_3$)(3') |

TABLE 25a

Compounds of the formula

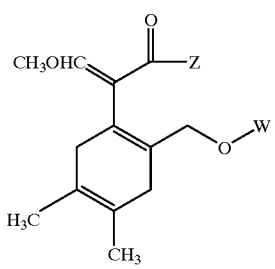

in which Z and W have the meanings of the corresponding compounds of Table 25.

TABLE 26

Comp. No. | Z | W | Physical data
--- | --- | --- | ---
26.001. | OMe | 3-$C_6H_4$—CO—$C_6H_3Cl_2$(2',4') |
26.002. | OMe | 3-$C_6H_4$—CO—$C_6H_5$ |
26.003. | OMe | 2-$C_6H_4$—CO—$C_6H_4$($OCH_3$)(4') |
26.004. | OMe | 3-$C_6H_4$—CO—$C_6H_3$($CF_3$)(3',5') |
26.005. | OMe | 2-$C_6H_4$—CO—$C_6H_4$($CF_3$)(3') |
26.006. | OMe | 3-$C_6H_4$—CO—$C_6H_4$($CF_3$)(3') |
26.007. | OMe | 2-$C_6H_4$—CO—CO—$C_6H_5$ |
26.008. | OMe | 2-$C_6H_4$—CO—CO—$C_6H_4$(Cl)(3') |
26.009. | OMe | 3-$C_6H_4$—CO—$C_6H_3$(CN)(3')($NO_2$)(4') |
26.010. | OMe | 3-$C_6H_4$—CO-pyrazinyl(2') |
26.011. | OMe | 3-$C_6H_4$—CO-pyridyl(3') |
26.012. | OMe | 3-$C_6H_4$—CO—CO-pyridyl(3') |
26.013. | OMe | 3-$C_6H_4$—CO-pyridyl(2') |
26.014. | OMe | 3-$C_6H_4$—CO-pyridyl(4') |
26.015. | OMe | 3-$C_6H_4$—CO—$C_6H_4$($CF_3$)(4') |
26.016. | OMe | 2-$C_6H_4$—CO—$C_6H_4$(Cl)(4') |
26.017. | OMe | 3-$C_6H_4$—CO—$C_6H_4$($NO_2$)(4') |
26.018. | OMe | 2-$C_6H_4$—CO-pyrimidinyl(2') |
26.019. | OMe | 3-$C_6H_4$—CO-pyrimidinyl(4') |
26.020. | OMe | 2-$C_6H_4$—CO-pyrimidinyl(5') |
26.021. | OMe | 3-$C_6H_4$—CO—CO—NH—$C_6H_4$—(OMe)(4') |
26.022. | OMe | 3-$C_6H_4$—CO—$CH_3$ |
26.023. | OMe | 3-$C_6H_4$—CO—CO—NH—$C_6H_4$—($CF_3$)(3') |
26.024. | OMe | 3-$C_6H_4$—CO—$C_6H_4$(Br)(4') |
26.025. | OMe | 1-$C_6H_4$—CO—$C_6H_2$($OCH_3$)$_3$(3',4',5') |
26.026. | OMe | 3-$C_6H_4$—CO—$C_6H_3$($CH_3$)$_2$(3',5') |
26.027. | OMe | 3-$C_6H_4$—CO-thiazolyl(2') |
26.028. | OMe | 3-$C_6H_4$—CO-oxazolyl(2') |
26.029. | OMe | 3-$C_6H_4$—CO-thienyl(2') |
26.030. | OMe | 3-$C_6H_4$—CO-thienyl(3') |
26.031. | OMe | 3-$C_6H_4$—CO-Et |
26.032. | OMe | 4-$C_6H_4$—CO—H |
26.033. | OMe | 2-$C_6H_4$—CO—H |
26.034. | OMe | 4-$C_6H_4$—CO—$CH_3$ |
26.035. | OMe | 3-$C_6H_4$—CO—CO—NH—$C_6H_4$—(Cl)(4') |
26.036. | OMe | 4-$C_6H_4$—CO—CO—NH—$C_6H_3$—($Cl_2$)(2',4') |
26.037. | OMe | 3-$C_6H_4$—CO—CO—NH—$C_6H_4$—($NO_2$)(4') |
26.038. | OMe | 2-$C_6H_4$—CO—$CF_3$ |
26.039. | OMe | 3-$C_6H_4$—CO—COOEt |
26.040. | OMe | 2-$C_6H_4$—CO—COOMe |
26.041. | OMe | 3-$C_6H_4$—CO—CO—NH—$C_6H_4$—(Br)(4') |
26.042. | OMe | 4-$C_6H_4$—CO—CO—NH—$C_6H_4$—(I)(4') |
26.043. | OMe | 4-$C_6H_4$—CO—CO—NH—$C_6H_4$—($CH_3$)(2') |
26.044. | OMe | 3-$C_6H_4$—CO—$CH_2$—OMe |
26.045. | OMe | 3-$C_6H_4$—CO—$C_4H_9$(n) |
26.046. | OMe | 4-$C_6H_4$—CO—$C_3H_7$(n) |
26.047. | OMe | 4-$C_6H_4$—CO—$C_8H_{17}$(n) |
26.048. | NHMe | 3-$C_6H_4$—CO—$C_6H_3Cl_2$(2',4') |
26.049. | NHMe | 4-$C_6H_4$—CO—$C_6H_5$ |
26.050. | NHMe | 3-$C_6H_4$—CO—$C_6H_4$($OCH_3$)(4') |
26.051. | NHMe | 4-$C_6H_4$—CO—$C_6H_3$($CF_3$)$_2$(3',5') |
26.052. | NHMe | 3-$C_6H_4$—CO—$C_6H_4$($CF_3$)(3') |
26.053. | NHMe | 3-$C_6H_4$—CO—CO—$C_6H_4$($CF_3$)(3') |
26.054. | NHMe | 4-$C_6H_4$—CO—CO—$C_6H_5$ |
26.055. | NHMe | 3-$C_6H_4$—CO—CO—$C_6H_4$(Cl)(3') |
26.056. | OMe | 3-$C_6H_4$—CO—CO—NH—$C_6H_3$—($CH_3$)$_2$(2',6') |
26.057. | NHMe | 3-$C_6H_4$—CO-pyrazinyl(2') |
26.058. | NHMe | 3-$C_6H_4$—CO-pyridyl(3') |
26.059. | NHMe | 4-$C_6H_4$—CO—CO-pyridyl(3') |

TABLE 26-continued

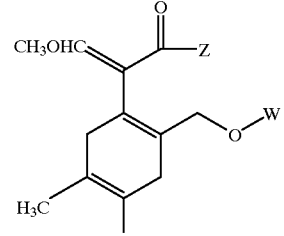

| Comp. No. | Z | W | Physical data |
|---|---|---|---|
| 26.060. | NHMe | 3-$C_6H_4$—CO-pyridyl(2') | |
| 26.061. | NHMe | 4-$C_6H_4$—CO-pyridyl(4') | |
| 26.062. | NHMe | 3-$C_6H_4$—CO—$C_6H_4$($CF_3$)(4') | |
| 26.063. | NHMe | 3-$C_6H_4$—CO—$C_6H_4$(Cl)(4') | |
| 26.064. | OMe | 3-$C_6H_4$—CO—CO—NH—$C_6H_3$-(Me)(2')(Et)(6') | |
| 26.065. | NHMe | 3-$C_6H_4$—CO-pyrimidinyl(2') | |
| 26.066. | NHMe | 3-$C_6H_4$—CO-pyrimidinyl(4') | |
| 26.067. | NHMe | 3-$C_6H_4$—CO-pyrimidinyl(5') | |
| 26.068. | OMe | 2-$C_6H_4$—CO—CO—NH—$C_6H_3$-(Me)$_2$(2',4') | |
| 26.069. | NHMe | 3-$C_6H_4$—CO—$CH_3$ | |
| 26.070. | OMe | 2-$C_6H_4$—CO—CO—NH—$C_6H_4$—(Cl)(3') | |
| 26.071. | NHMe | 4-$C_6H_4$—CO—$C_6H_4$(Br)(4') | |
| 26.072. | NHMe | 3-$C_6H_4$—CO—$C_6H_2$($OCH_3$)$_3$(3',4',5') | |
| 26.073. | NHMe | 3-$C_6H_4$—CO—$C_6H_3$($CH_3$)$_2$(3',5') | |
| 26.074. | NHMe | 4-$C_6H_4$—CO-thiazolyl(2') | |
| 26.075. | NHMe | 3-$C_6H_4$—CO-oxazolyl(2') | |
| 26.076. | NHMe | 3-$C_6H_4$—CO-thienyl(2') | |
| 26.077. | NHMe | 4-$C_6H_4$—CO-thienyl(3') | |
| 26.078. | NHMe | 3-$C_6H_4$—CO-Et | |
| 26.079. | NHMe | 4-$C_6H_4$—CO—$CH_3$ | |
| 26.080. | NHMe | 2-$C_6H_4$—CO—$CH_3$ | |
| 26.081. | NHMe | 4-$C_6H_4$—CO—$CH_3$ | |
| 26.082. | OMe | 3-$C_6H_4$—CO—CO—NH—$C_6H_4$—(Cl)(2') | |
| 26.083. | OMe | 3-$C_6H_4$—CO—CO—NH—$C_6H_3$—(Cl)$_2$(3',5') | |
| 26.084. | OMe | 3-$C_6H_4$—CO—CO—NH—$C_6H_3$—($CF_3$)$_2$(3',5') | |
| 26.085. | NHMe | 2-$C_6H_4$—CO—$CF_3$ | |
| 26.086. | NHMe | 3-$C_6H_4$—CO—COOEt | |
| 26.087. | NHMe | 2-$C_6H_4$—CO—COOMe | |
| 26.088. | OMe | 3-$C_6H_4$—CO—CO—NH—$C_6H_4$—($CF_3$)(4') | |
| 26.089. | OMe | 3-$C_6H_4$—CO—CO—NH—$C_6H_4$—($OCH_3$)(4') | |
| 26.090. | OMe | 4-$C_6H_4$—CO—CO—NH—$C_6H_4$—($OCF_3$)(4') | |
| 26.091. | NHMe | 4-$C_6H_4$—CO—$CH_2$—OMe | |
| 26.092. | NHMe | 3-$C_6H_4$—CO—$C_4H_9$(n) | |
| 26.093. | NHMe | 3-$C_6H_4$—CO—$C_3H_7$(n) | |
| 26.094. | NHMe | 3-$C_6H_4$—CO—$C_8H_{17}$(n) | |
| 26.095. | NHMe | 4-$C_6H_4$—CO—$C_6H_4$($CH_3$)(3') | |
| 26.096. | NHMe | 4-$C_6H_4$—CO—$CH_2$-morpholinyl(1) | |
| 26.097. | NHMe | 3-$C_6H_4$—CO—$CH_2$-piperidinyl(1) | |
| 26.098. | NHMe | 3-$C_6H_4$—CO—$CH_2$—Cl | |
| 26.099. | OMe | 3-$C_6H_4$—CO—$C_6H_4$($CH_3$)(3') | |
| 26.100. | NHMe | 3-$C_6H_4$—CO—$CH_2$—O—$C_6H_3$($Cl_2$)(2',4') | |
| 26.101. | NHMe | 3-$C_6H_4$—CO—$CH_2$—O—$C_6H_4$($CH_3$)(2') | |
| 26.102. | NHMe | 3-$C_6H_4$—CO—$CH_2$—C—$C_6H_4$($CH_3$)(3') | |
| 26.103. | OMe | 4-$C_6H_4$—CO—$C_6H_4$(F)(4') | 117–119° |
| 26.104. | OMe | 4-$C_6H_4$—CO—$C_6H_4$(—C≡C—$C_6H_5$)(4') | 125–127° |
| 26.105. | OMe | 4-$C_6H_4$—CO—$C_6H_4$(—$CH_2$—$CH_2$—$C_6H_5$)(4') | 80–82° |

TABLE 27

Compounds of the formula in which Z and W have the meanings of the corresponding compounds of Table 26.

TABLE 28

| Comp. No. | Z | W | Physical data |
|---|---|---|---|
| 28.001. | OMe | 3-$C_6H_4$—$C_6H_3Cl_2$(2',4') | |
| 28.002. | OMe | 3-$C_6H_4$—$C_6H_5$ | |
| 28.003. | OMe | 3-$C_6H_4$—$C_6H_4$($OCH_3$)(4') | |
| 28.004. | OMe | 3-$C_6H_4$—$C_6H_3$($CF_3$)$_2$(3',5') | |
| 28.005. | OMe | 3-$C_6H_4$—$C_6H_4$($CF_3$)(3') | |
| 28.006. | OMe | 3-$C_6H_4$—$SO_2$—NH—$C_6H_4$($CF_3$)(3') | |
| 28.007. | OMe | 3-$C_6H_4$—NH—$C_6H_4$($CF_3$)(3') | |
| 28.008. | OMe | 3-$C_6H_4$—NH—CO—$C_6H_4$($CF_3$)(3') | |
| 28.009. | OMe | 3-$C_6H_4$—$C_6H_3$(CN)(3')($NO_2$)(4) | |
| 28.010. | OMe | 3-$C_6H_4$-pyrazinyl(2') | |
| 28.011. | OMe | 3-$C_6H_4$-pyridyl(3') | |
| 28.012. | OMe | 3-$C_6H_4$—O—$CH_2$-dioxolanyl(2') | |
| 28.013. | OMe | 3-$C_6H_4$-pyridyl(2') | |
| 28.014. | OMe | 3-$C_6H_4$-pyridyl(4') | |
| 28.015. | OMe | 3-$C_6H_4$—$C_6H_4$($CF_3$)(4') | |
| 28.016. | OMe | 3-$C_6H_4$—$C_6H_4$(Cl)(4') | |
| 28.017. | OMe | 3-$C_6H_4$—$C_6H_4$($NO_2$)(4') | |
| 28.018. | OMe | 3-$C_6H_4$-pyrimidinyl(2') | |
| 28.019. | OMe | 3-$C_6H_4$-pyrimidinyl(4') | |
| 28.020. | OMe | 3-$C_6H_4$-pyrimidinyl(5') | |
| 28.021. | OMe | 3-$C_6H_4$—O—$CH_2$—CH(OMe)2 | |
| 28.022. | OMe | 3-$C_6H_4$—O—$CH_2$—CH(OEt)2 | |
| 28.023. | OMe | 3-$C_6H_4$—O—$SO_2$—$NEt_2$ | |
| 28.024. | OMe | 3-$C_6H_4$—$C_6H_4$(Br)(4') | |
| 28.025. | OMe | 3-$C_6H_4$—$C_6H_2$($OCH_3$)$_3$(3',4',5') | |
| 28.026. | OMe | 3-$C_6H_4$—$C_6H_3$($CH_3$)$_2$(3',5') | |
| 28.027. | OMe | 3-$C_6H_4$-thiazolyl(2') | |
| 28.028. | OMe | 3-$C_6H_4$-oxazolyl(2') | |
| 28.029. | OMe | 3-$C_6H_4$-thienyl(2') | |
| 28.030. | OMe | 3-$C_6H_4$-thienyl(3') | |
| 28.031. | OMe | 3-$C_6H_4$—S—$C_6H_5$ | |
| 28.032. | OMe | 3-$C_6H_4$—$C_6H_3$($CH_3$)$_2$(3',5') | |
| 28.033. | OMe | 2-$C_6H_4$—$CH_2$—H | |
| 28.034. | OMe | 4-$C_6H_4$—$CH_2$—$CH_3$ | |
| 28.035. | OMe | 3-$C_6H_4$—$CH_2$—CO—NH—$C_6H_4$(Cl)(4') | |
| 28.036. | OMe | 3-$C_6H_4$—$CH_2$—CO—NH—$C_6H_3$($Cl_2$)(2',4') | |
| 28.037. | OMe | 3-$C_6H_4$—$CH_2$—CO—NH—$C_6H_4$($NO_2$)(4') | |
| 28.038. | OMe | 3-$C_6H_4$—$CH_2$—$CF_3$ | |
| 28.039. | OMe | 3-$C_6H_4$—$CH_2$—COOEt | |
| 28.040. | OMe | 3-$C_6H_4$—$CH_2$—COOMe | |

TABLE 28-continued

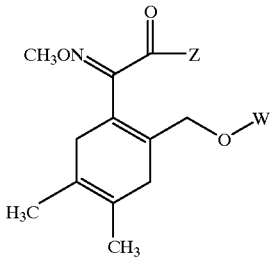

| Comp. No. | Z | W | Physical data |
|---|---|---|---|
| 28.041. | OMe | 3-$C_6H_4$—$CH_2$—CO—NH—$C_6H_4$—(Br)(4') | |
| 28.042. | OMe | 3-$C_6H_4$—$CH_2$—CO—NH—$C_6H_4$—(I)(4') | |
| 28.043. | OMe | 3-$C_6H_4$—$CH_2$—CO—NH—$C_6H_4$—($CH_3$)(2') | |
| 28.044. | OMe | 3-$C_6H_4$—$CH_2$—$CH_2$—OMe | |
| 28.045. | OMe | 3-$C_6H_4$—$CH_2$—$C_4H_9$(n) | |
| 28.046. | OMe | 3-$C_6H_4$—$CH_2$—$C_3H_7$(n) | |
| 28.047. | OMe | 3-$C_6H_4$—$CH_2$—$C_8H_{17}$(n) | |
| 28.048. | NHMe | 3-$C_6H_4$—$C_6H_3Cl_2$(2',4') | |
| 28.049. | NHMe | 3-$C_5H_4$—$C_6H_5$ | |
| 28.050. | NHMe | 3-$C_6H_4$—$C_6H_4$($OCH_3$)(4') | |
| 28.051. | NHMe | 3-$C_6H_4$—$C_6H_3(CF_3)_2$(3',5') | |
| 28.052. | NHMe | 3-$C_6H_4$—$C_6H_4(CF_3)$(3') | |
| 28.053. | NHMe | 3-$C_6H_4$—$CH_2$—CO—$C_6H_4(CF_3)$(3') | |
| 28.054. | NHMe | 3-$C_6H_4$—$CH_2$—CO—$C_6H_5$ | |
| 28.055. | NHMe | 3-$C_6H_4$—$CH_2$—CO—$C_6H_4$(Cl)(3') | |
| 28.056. | OMe | 3-$C_6H_4$—$CH_2$—CO—NH—$C_6H_3$—$(CH_3)_2$(2',6') | |
| 28.057. | NHMe | 3-$C_6H_4$-pyrazinyl(2') | |
| 28.058. | NHMe | 3-$C_6H_4$-pyridyl(3') | |
| 28.060. | NHMe | 3-$C_6H_4$-pyridyl(2') | |
| 28.061. | NHMe | 3-$C_6H_4$-pyridyl(4') | |
| 28.062. | NHMe | 3-$C_6H_4$—$C_6H_4(CF_3)$(4') | |
| 28.063. | NHMe | 3-$C_6H_4$—$C_6H_4$(Cl)(4') | |
| 28.064. | OMe | 3-$C_6H_4$—$CH_2$—CO—NH—$C_6H_3$-(Me)(2')(Et)(6') | |
| 28.065. | NHMe | 3-$C_6H_4$-pyrimidinyl(2') | |
| 28.066. | NHMe | 3-$C_6H_4$-pyrimidinyl(4') | |
| 28.067. | NHMe | 3-$C_6H_4$-pyrimidinyl(5') | |
| 28.068. | OMe | 3-$C_6H_4$—$CH_2$—CO—NH—$C_6H_3$-$(Me)_2$(2',4') | |
| 28.069. | NHMe | 3-$C_6H_4$—$CH_2$—$CH_3$ | |
| 28.070. | OMe | 3-$C_6H_4$—$CH_2$—CO—NH—$C_6H_4$—(Cl)(3') | |
| 28.071. | NHMe | 3-$C_6H_4$—$C_6H_4$(Br)(4') | |
| 28.072. | NHMe | 3-$C_6H_4$—$C_6H_2(OCH_3)_3$(3',4',5') | |
| 28.073. | NHMe | 3-$C_6H_4$—$C_6H_3(CH_3)_2$(3',5') | |
| 28.074. | NHMe | 3-$C_6H_4$-thiazolyl(2') | |
| 28.075. | NHMe | 3-$C_6H_4$-oxazolyl(2') | |
| 28.076. | NHMe | 3-$C_6H_4$-thienyl(2') | |
| 28.077. | NHMe | 3-$C_6H_4$-thienyl(3') | |
| 28.078. | NHMe | 3-$C_6H_4$—$CH_2$-Et | |
| 28.079. | NHMe | 4-$C_6H_4$—$CH_2$—$CH_3$ | |
| 28.080. | NHMe | 2-$C_6H_4$—$CH_2$—$CH_3$ | |
| 28.081. | NHMe | 4-$C_6H_4$—$CH_2$—$CH_3$ | |
| 28.082. | OMe | 3-$C_6H_4$—$CH_2$—CO—NH—$C_6H_4$—(Cl)(2') | |
| 28.083. | OMe | 3-$C_6H_4$—$CH_2$—CO—NH—$C_6H_3$—$(Cl)_2$(3',5') | |
| 28.084. | OMe | 3-$C_6H_4$—$CH_2$—CO—NH—$C_6H_3$—$(CF_3)_2$(3',5') | |
| 28.085. | NHMe | 3-$C_6H_4$—$CH_2$—$CF_3$ | |
| 28.086. | NHMe | 3-$C_6H_4$—$CH_2$—COOEt | |
| 28.087. | NHMe | 3-$C_6H_4$—$CH_2$—COOMe | |
| 28.088. | OMe | 3-$C_6H_4$—$CH_2$—CO—NH—$C_6H_4$—($CF_3$)(4') | |
| 28.089. | OMe | 3-$C_6H_4$—$CH_2$—CO—NH—$C_6H_4$—($OCH_3$)(4') | |
| 28.090. | OMe | 3-$C_6H_4$—$CH_2$—CO—NH—$C_6H_4$—($OCF_3$)(4') | |
| 28.091. | NHMe | 3-$C_6H_4$—$CH_2$—$CH_2$—OMe | |
| 28.092. | NHMe | 3-$C_6H_4$—$CH_2$—$C_4H_9$(n) | |
| 28.093. | NHMe | 3-$C_6H_4$—$CH_2$—$C_3H_7$(n) | |

TABLE 28-continued

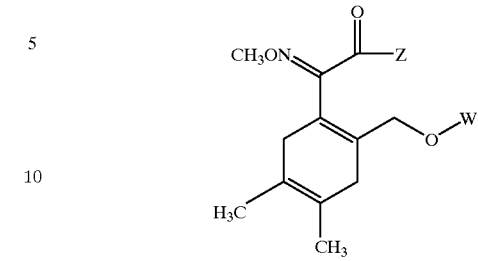

| Comp. No. | Z | W | Physical data |
|---|---|---|---|
| 28.094. | NHMe | 3-$C_6H_4$—$CH_2$—$C_8H_{17}$(n) | |
| 28.095. | NHMe | 3-$C_6H_4$—$C_6H_4(CH_3)$(3') | |
| 28.096. | NHMe | 3-$C_6H_4$—$CH_2$—$CH_2$-morpholinyl(1) | |
| 28.097. | NHMe | 3-$C_6H_4$—$CH_2$—$CH_2$-piperidinyl(1) | |
| 28.098. | NHMe | 3-$C_6H_4$—$CH_2$—$CH_2$—Cl | |
| 28.099. | OMe | 3-$C_6H_4$—$C_6H_4(CH_3)$(3') | |
| 28.100. | NHMe | 3-$C_6H_4$—$CH_2$—$CH_2$—O—$C_6H_3(Cl_2)$(2',4') | |
| 28.101. | NHMe | 3-$C_6H_4$—$CH_2$—$CH_2$—O—$C_6H_4(CH_3)$(2') | |
| 28.102. | NHMe | 3-$C_6H_4$—$CH_2$—$CH_2$—O—$C_6H_4(CH_3)$(3') | |
| 28.103. | OMe | 3-$C_6H_4$—$C_6H_4$(F)(2')(Cl)(3') | |

TABLE 28a

Compounds of the formula

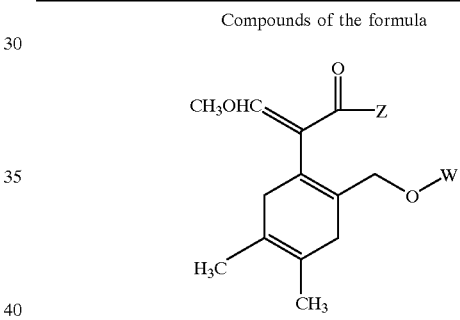

in which Z and W have the meanings of the corresponding compounds of Table 28.

2. Formulation examples for active ingredients of the tables (%=percent by weight)

| 2.1 Wettable powders | a) | b) | c) |
|---|---|---|---|
| Active ingredient from the tables | 25% | 50% | 75% |
| Sodium ligninosulfonate | 5% | 5% | — |
| Sodium lauryl sulfate | 3% | — | 5% |
| Sodium diisobutylnaphthalenesulfonate | — | 6% | 10% |
| Octylphenyl polyethylene glycol ether (7–8 mol of ethylene oxide) | — | 2% | — |
| Highly disperse silica | 5% | 10% | 10% |
| Kaolin | 62% | 27% | — |

The active ingredient is mixed with the additives and the mixture is ground in a suitable mill until homogeneous. This gives wettable powders which can be diluted with water to give suspensions of any desired concentration.

| 2.2 Emulsion concentrate | |
|---|---|
| Active ingredient from the tables | 10% |
| Octylphenyl potyethylene glycol ether (4–5 mol of ethylene oxide) | 3% |
| Calcium dodecylbenzenesulfonate | 3% |
| Castor oil polyglycol ether (35 mol of ethylene oxide) | 4% |
| Cyclohexanone | 30% |
| Xylene mixture | 50% |

Emulsions of any desired dilution can be prepared from this concentrate by diluting it with water.

| 2.3 Dusts | a) | b) |
|---|---|---|
| Active ingredient from the tables | 5% | 8% |
| Talc | 95% | — |
| Kaolin | — | 92% |

Ready-to-use dusts are obtained by mixing the active ingredient with the carriers and grinding the mixture in a suitable mill.

| 2.4 Extruder granules | |
|---|---|
| Active ingredient from the tables | 10% |
| Sodium lignosulfonate | 2% |
| Carboxymethylcellulose | 1% |
| Kaolin | 87% |

The active ingredient is mixed with the additives, and the mixture is ground and moistened with water. This mixture is extruded and subsequently dried in a stream of air.

| 2.5 Coated granules | |
|---|---|
| Active ingredient from the tables | 3% |
| Polyethylene glycol (MW 200) | 3% |
| Kaolin | 94% |

(MW = molecular weight)

In a mixer, the finely ground active ingredient is applied uniformly to the kaolin which has been moistened with polyethylene glycol. This gives dust-free coated granules.

| 2.6 Suspension concentrate | |
|---|---|
| Active ingredient from the tables | 40% |
| Ethylene glycol | 10% |
| Nonylphenyl polyethylene glycol ether (15 mol of ethylene oxide) | 6% |
| Sodium lignosulfonate | 10% |
| Carboxymethylcellulose | 1% |
| 37% aqueous formaldehyde solution | 0.2% |
| Silicone oil as 75% aqueous emulsion | 0.8% |
| Water | 32% |

The finely ground active ingredient is mixed intimately with the additives. This gives a suspension concentrate from which suspensions of any desired dilution can be prepared by diluting it with water.

BIOLOGICAL EXAMPLES

A. Microbicidal Actions

EXAMPLE B-1

Action Against *Puccinia graminis* on Wheat a) Residual-protective Action

Wheat plants are sown and, 6 days thereafter, sprayed to drip point with an aqueous spray mixture prepared with a wettable powder of the active ingredient (0.02% active substance) and, 24 hours later, infected with a uredospore suspension of the fungus. After an incubation time of 48 hours (conditions: 95 to 100 percent relative atmospheric humidity at 20°), the plants are placed in a greenhouse at 22°. The fungus infestation is assessed 12 days after the infection.

b) Systemic Action

An aqueous spray mixture prepared with a wettable powder of the active ingredient is poured next to wheat plants 5 days after they have been sown. (0.006% active substance based on the soil volume). Care is taken that the spray mixture does not come into contact with aerial plant organs. 48 hours later, the plants are infected with a uredospore suspension of the fungus. After an incubation time of 48 hours (conditions: 95 to 100 percent relative atmospheric humidity at 20°), the plants are placed in a greenhouse at 22°. The fungus infestation is assessed 12 days after the infection. Compounds from the tables exhibit good activity.

EXAMPLE B-2

Action Against *Phytophthora infestans* on Tomatoes a) Residual-protective Action Tomato plants are grown for three weeks and then sprayed to drip point with an aqueous spray mixture prepared with a wettable powder of the active ingredient (0.02% active substance) and, 24 hours later, infected with a sporangia suspension of the fungus. The fungus infestation is assessed 5 days after the infection, during which a relative atmospheric humidity of 90 to 100 percent and a temperature of 20° are maintained.

b) Systemic Action

An aqueous spray mixture prepared with a wettable powder of the active ingredient is poured next to tomato plants which have been grown for three weeks (0.006% active substance based on the soil volume). Care is taken that the spray mixture does not come into contact with aerial plant organs. After 48 hours, the plants are infected with a sporangia suspension of the fungus. The fungus infestation is assessed 5 days after the infection, during which a relative atmospheric humidity of 90 to 100 percent at a temperature of 20° are maintained. The compounds from the tables exhibit good activity.

EXAMPLE B-3

Residual-protective Action Against *Cercospora arachidicola* on Peanuts

Peanut plants 10 to 15 cm in height are sprayed to drip point with an aqueous spray mixture prepared with a wettable powder of the active ingredient (0.02% active substance) and, 48 hours later, infected with a conidia suspension of the fungus. The plants are incubated for 72 hours at 21° and high atmospheric humidity and subsequently placed in a greenhouse until the typical foliar lesions develop. The activity of the active substance is assessed 12 days after the infection on the basis of number and size of the foliar lesions. Compounds from the tables exhibit good activity.

EXAMPLE B-4

Action Against *Plasmopara viticola* on Grapevines

Grapevine seedlings in the 4–5-leaf stage are sprayed to drip point with an aqueous spray mixture prepared with a wettable powder of the active ingredient (0.02% active substance) and, 24 hours later, infected with a sporangia suspension of the fungus. The fungus infestation is assessed 6 days after the infection, during which a relative atmospheric humidity of 95 to 100 percent and a temperature of 20° are maintained. Compounds from the tables exhibit good activity.

EXAMPLE B-5

Action Against *Colletotrichum lagenarium* on Cucumbers

Cucumber plants are grown for 2 weeks and then sprayed with a spray mixture prepared with a wettable powder of the active ingredient (concentration 0.002%). After 2 days, the plants are infected with a spore suspension ($1.5 \times 10^5$ spores/ml) of the fungus and incubated for 36 hours at 23° C. and high atmospheric humidity. Incubation is then continued at normal atmospheric humidity and at approximately 22° C. 8 days after the infection, the fungus infestation which has taken place is assessed. Compounds from the tables exhibit good activity.

EXAMPLE B-6

Residual Protective Action Against *Venturia inaegualis* on Apples

Apple cuttings with fresh shoots 10 to 20 cm in length are sprayed to drip point with an aqueous spray mixture prepared with a wettable powder of the active ingredient (0.02% active substance) and, 24 hours later, infected with a conidia suspension of the fungus. The plants are incubated for 5 days at a relative atmospheric humidity of 90 to 100 percent and placed for a further 10 days in a greenhouse at 20 to 24°. The fungus infestation is assessed 12 days after the infection. Compounds from the tables exhibit good activity.

EXAMPLE B-7

Action Against *Erysiphe graminis* on Barley
a) Residual-protective Action
Barley plants approximately 8 cm in height are sprayed to drip point with an aqueous spray mixture prepared with a wettable powder of the active ingredient (0.02% active substance) and, 3 to 4 hours later, dusted with conidia of the fungus. The infected plants are placed in a greenhouse at 22°. The fungus infestation is assessed 12 days after the infection. Compounds from the tables exhibit good activity.
b) Systemic Action
An aqueous spray mixture prepared with a wettable powder of the active ingredient is poured next to barley plants approximately 8 cm in height (0.002% active substance based on the soil volume). Care is taken that the spray mixture does not come into contact with aerial plant organs. 48 hours later, the plants are dusted with conidia of the fungus. The infected plants are placed in a greenhouse at 22°. The fungus infestation is assessed 12 days after the infection. Compounds from the tables exhibit good activity.

EXAMPLE B-8

Action Against *Podosphaera leucotricha* on Apple Shoots

Apple cuttings with fresh shoots approximately 15 cm in length are sprayed with a spray mixture (0.06% active substance). After 24 hours, the treated plants are infected with a conidia suspension of the fungus and placed in a controlled-environment cabinet at a relative atmospheric humidity of 70% and at 20° C. The fungus infestation is assessed 12 days after the infection. Compounds from the tables exhibit good activity.

BIOLOGICAL EXAMPLES

B. Insecticidal Actions

EXAMPLE B-9

Action Against *Aphis craccivora*

Pea seedlings are infected with *Aphis craccivora*, subsequently sprayed with a spray mixture comprising 100 ppm of active ingredient and then incubated at 20°. 3 and 6 days later, the percentage reduction in population (% activity) is determined by comparing the number of dead aphids on treated and untreated plants. In this test, compounds of the tables exhibit good activity, i.e. a destruction rate of over 80%.

EXAMPLE B-10

Action Against *Diabrotica balteata*

Maize seedlings are sprayed with an aqueous emulsion spray mixture comprising 400 ppm of active ingredient, then, after the spray coating has dried on, populated with 10 second instar larvae of *Diabrotica balteata* and subsequently introduced into a plastic container. 6 days later, the percentage reduction in population (% activity) is determined by comparing the number of dead larvae between the treated and untreated plants. In this test, compounds of the tables exhibit good activity.

EXAMPLE B-11

Action Against *Heliothis virescens*

Young soya plants are sprayed with an aqueous emulsion spray mixture comprising 100 ppm of active ingredient, then, after the spray coating has dried on, populated with 10 first instar caterpillars of *Heliothis virescens* and subsequently introduced into a plastic container. 6 days later, the percentage reduction in population and the feeding damage (% activity) are determined by comparing the number of dead caterpillars and the feeding damage between the treated and untreated plants. In this test, compounds of the tables exhibit good activity.

EXAMPLE B-12

Action Against *Spodoptera littoralis*

Young soya plants are sprayed with an aqueous emulsion spray mixture comprising 100 ppm of active ingredient, then, after the spray coating has dried on, populated with 10 third instar caterpillars of *Spodoptera littoralis* and subsequently introduced into a plastic container. 3 days later, the percentage reduction in population and the percentage reduction in feeding damage (% activity) are determined by comparing the number of dead caterpillars and the feeding damage between the treated and untreated plants. In this test, compounds of the tables exhibit good activity.

B-13

Action Against *Nilaparvata lugens*

Rice plants are treated with an aqueous emulsion spray mixture which comprises 100 ppm of the active ingredient. After the spray coating has dried on, the rice plants are populated with 2nd and 3rd instar leafhopper larvae. The test is evaluated 21 days later. The percentage reduction in population (% activity) is determined by comparing the number of surviving leafhoppers on the treated with those on the untreated plants. The compounds of the tables exhibit an activity of over 90%.

B-14

Action Against *Plutella xylostella* Caterpillars

Young cabbage plants are sprayed with an aqueous emulsion spray mixture which comprises 100 ppm of the active ingredient. After the spray coating has dried on, the cabbage plants are populated with 10 third instar caterpillars of *Plutella xylostella* and introduced into a plastic container. The test is evaluated 3 days later. The percentage reduction in population or the percentage reduction in feeding damage (% activity) is determined by comparing the number of dead caterpillars and the feeding damage on the treated with those on the untreated plants. Compounds from the tables exhibit good activity.

EXAMPLE B-15

Action Against *Musca domestica*

A sugar lump is treated with a solution of the test substance in such a way that, after drying overnight, the concentration of test substance in the sugar is 250 ppm. This treated lump is placed on an aluminium dish together with a wet cotton wool ball and 10 adult Musca domestica of an OP-resistant strain, covered with a glass beaker and incubated at 25° C. The mortality rate is determined after 24 hours. Compounds from the tables exhibit good activity.

BIOLOGICAL EXAMPLES

C. Acaricidal Actions

B-16

Action Against *Tetranychus urticae*

Young bean plants are populated with a mixed population of *Tetranychus urticae* and, one day later, sprayed with an aqueous emulsion spray mixture which comprises 400 ppm of the active ingredient. The plants are subsequently incubated for 6 days at 25° C. and then evaluated. The percentage reduction in population (% action) is determined by comparing the number of dead eggs, larvae and adults on the treated with those on the untreated plants. Compounds from the tables exhibit good activity.

B-17

Action on Mixed Population of *Tetranychus cinnabarinus*

Dilution Series

Dwarf beans in the 2-leaf stage are populated with a mixed population (eggs, larvae/nymphs, adults) of an OP-tolerant strain of *Tetranychus cinnabarinus*. 24 hours after infection, the products are applied to the plants in an automatic spray cabin at the dosages 200, 100, 50 mg of a.s./l. The substances are formulated and are diluted with water to give the appropriate dosages. The test is evaluated 2 and 7 days after application for percentage mortality of eggs, larvae/nymphs and adults. Compounds of the tables exhibit mortality rates above 70% in dilutions of as little as 50 mg of a.s./liter.

B-18

Action Against *Boophilus microplus*

Female adult ticks which have sucked themselves full are glued to a PVC pane and covered with a cotton wool ball, and 10 ml of aqueous test solution comprising 125 ppm of active ingredient are poured over. The cotton wool ball is removed and the ticks are incubated for 4 weeks for oviposition. The action manifests itself either in the case of the female as mortality or sterility or in the case of the eggs as ovicidal action.

What is claimed is:

1. A compound of the formula I

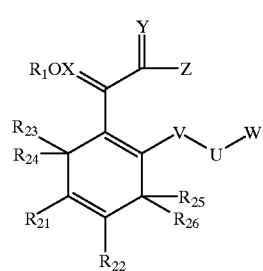

I where:

X is CH or N;

Y is O; S, S=O or $NR_5$;

Z is $OR_2$, $SR_2$, $N(R_3)R_4$; or

Y and Z together form a 5- to 7-membered ring selected from the group consisting of

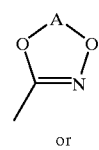

a)

or b)
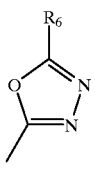

or c)
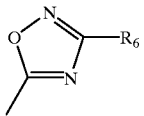

or d)
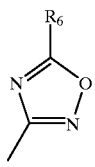

and in which:
- A is alkanediyl having 1 to 3 carbon atoms which is unsubstituted or substituted by methyl, preferably dimethylene;
- $R_6$ is hydrogen, $C_1$–$C_3$alkyl, cyclopropyl or $CF_3$;
- V is a direct bond or $C_1$–$C_6$alkylene which is unsubstituted or substituted by $C_1$–$C_3$alkyl, $C_2$–$C_3$alkylidene or $C_3$–$C_6$cycloalkylidene;
- U is O, S, $NR_7$, SO or $SO_2$;
- W is substituted or unsubstituted aryl or substituted or unsubstituted hetaryl;
- $R_1$ is cyclopropyl, $C_1$–$C_6$alkyl or halo-$C_1$–$C_6$alkyl;
- $R_2$ and $R_3$ independently of one another are $C_1$–$C_6$alkyl or halo-$C_1$–$C_6$alkyl;
- $R_4$ and $R_5$ independently of one another are hydrogen, $C_1$–$C_6$alkyl or $C_1$–$C_6$alkoxy;
- $R_7$ is hydrogen, $C_1$–$C_6$alkyl, benzyl, $C_1$–$C_6$alkylcarbonyl, halo-$C_1$–$C_6$alkylcarbonyl, halo-$C_2$–$C_6$alkenylcarbonyl;
- $R_{21}$ and $R_{22}$ independently of one another are hydrogen, halogen, $C_1$–$C_8$alkyl or $C_1$–$C_8$alkoxy or $C_1$–$C_8$alkylthio;
- $R_{23}$, $R_{24}$, $R_{25}$, $R_{26}$ independently of one another are hydrogen, halogen, $C_1$–$C_8$alkyl or $C_1$–$C_8$alkoxy.

2. A compound of the formula I according to claim 1 in which

W is a group

in which
- D are identical or different substituents halogen, cyano, nitro, $C_1$–$C_{12}$alkyl, halo-$C_1$–$C_6$alkyl, $C_2$–$C_{12}$alkenyl, halo-$C_2$–$C_{12}$alkenyl, $C_2$–$C_{12}$alkynyl, halo-$C_2$–$C_{12}$alkynyl, free or halogenated $C_3$–$C_6$cycloalkyl, free or halogenated $C_3$–$C_6$cycloalkylmethyl, free or halogenated $C_3$–$C_6$cycloalkylmethyloxy, $C_1$–$C_4$alkoxy, halo-$C_1$–$C_4$alkoxy, $C_2$–$C_6$alkenyloxy, halo-$C_2$–$C_6$alkenyloxy, $C_2$–$C_6$alkynyloxy, halo-$C_2$–$C_6$alkynyloxy, $C_2$–$C_{12}$alkoxyalkyl, $C_1$–$C_4$alkoxycarbonyl, $C_1$–$C_6$alkylcarbonyl, it being possible for all the abovementioned alkyl, alkenyl or alkynyl groups to be substituted by aryl or hetaryl, aryloxy or hetaryloxy, arylsulfenyl, arylsulfinyl, arylsulfonyl, hetarylsulfenyl, hetarylsulfinyl or hetarylsulfonyl radicals, each of which can be additionally substituted or unsubstituted; furthermore substituted or unsubstituted aryl, substituted or unsubstituted hetaryl, substituted or unsubstituted heterocyclyl, substituted or unsubstituted arylcarbonyl, substituted or unsubstituted aryloxy, substituted or unsubstituted benzyl, substituted or unsubstituted cyclohexenyl, substituted or unsubstituted cyclohexenylalkoxy, substituted or unsubstituted cyclohexenylalkylthio, substituted or unsubstituted cyclohexadienyl, substituted or unsubstituted cyclohexadienylalkoxy, substituted or unsubstituted cyclohexadienylalkylthio, a substituted or unsubstituted fused ring having up to 14 C atoms, or in which D is the group

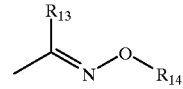

in which
- $R_{13}$ is hydrogen, cyano, $C_1$–$C_6$alkyl, $C_3$–$C_6$cycloalkyl, $C_1$–$C_6$alkoxycarbonyl, $C_1$–$C_6$alkanoyl, $C_1$–$C_2$alkoxyimino-$C_1$–$C_6$alkyl, aryl, hetaryl, heterocyclyl, naphthyl; $C_1$–$C_6$alkoxy, aryloxy, hetaryloxy, $C_1$–$C_6$alkylamino, bis($C_1$–$C_6$alkyl)amino, arylamino, hetarylamino, in which all the abovementioned radicals (with the exception of cyano) can be unsubstituted or substituted by alkyl, alkoxy, haloalkyl, haloalkoxy, alkylthio, alkylsulfenyl, alkylsufinyl, halogen, nitro, cyano, aryl, aryloxy, hetaryl, hetaryloxy; or
- $R_{13}$ is the group

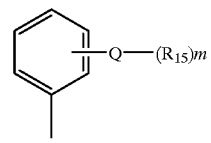

in which
- $R_{15}$ is hydrogen, $C_1$–$C_6$alkyl, halo-$C_1$–$C_6$alkyl, $C_1$–$C_6$alkoxy, halo-$C_1$–$C_6$alkoxy, halogen, $C_3$–$C_6$cycloalkyl which is unsubstituted or substituted by 1 to 5 halogen atoms, $C_2$–$C_6$alkenyl; halo-$C_2$–$C_6$alkenyl, substituted or unsubstituted $C_2$–$C_6$alkynyl; aryl, hetaryl or heterocyclyl, all three of which independently of one another are unsubstituted or monosubstituted to pentasubstituted by $C_1$–$C_6$alkyl, halo-$C_1$–$C_6$alkyl, halogen, $C_1$–$C_6$alkoxy or halo-$C_1$–$C_6$alkoxy; tri($C_1$–$C_4$-alkyl)silyl, di($C_1$–$C_4$alkyl)phenylsilyl;

where, if m is greater than 1, the radicals $R_{15}$ can be identical or different;
- Q is a direct bond, $C_1$–$C_8$alkylene, $C_2$–$C_6$alkenylene, $C_2$–$C_6$alkynylene, O, O($C_1$–$C_6$alkylene), ($C_1$–$C_6$alkylene)O, S(=O)$_p$, S(=O)$_p$($C_1$–$C_6$alkylene) or ($C_1$–$C_6$alkylene)S(=O)$_p$;

n is 0, 1, 2, 3, 4 or 5;

m is 0, 1, p is 0, 1 or 2; and $R_{14}$ is hydrogen; $C_1$–$C_6$alkyl; $C_1$–$C_6$haloalkyl having 1 to 15 halogen atoms; $C_1$–$C_4$alkoxy-$C_1$–$C_2$alkyl; $C_2$–$C_4$alkenyl-$C_1$–$C_2$alkyl which is unsubstituted or substituted by 1 to 3 halogen atoms; $C_2$–$C_4$alkynyl-$C_1$–$C_2$alkyl; $C_3$–$C_6$cycloalkyl which is unsubstituted or substituted by 1 to 4 halogen atoms; $C_3$–$C_6$cycloalkyl-$C_1$–$C_4$alkyl which is unsubstituted or substituted by 1 to 4 halogen atoms; cyano-$C_1$–$C_4$alkyl; $C_1$–$C_4$alkoxycarbonyl-$C_1$–$C_4$alkyl; phenyl-$C_1$–$C_3$alkyl which is unsubstituted or substituted by halogen, $C_1$–$C_3$alkyl, $C_1$–$C_4$alkoxy, $C_1$–$C_4$haloalkyl, cyano, nitro, $C_1$–$C_4$alkylene dioxy, it being possible for the phenyl group to be substituted by 1 to 3 identical or different substituents; phenyl which is unsubstituted or monosubstituted or disubstituted by independent substituents from the series consisting of $C_1$–$C_4$alkyl, $C_1$–$C_4$alkoxy, halogen, $C_1$–$C_2$haloalkyl having 1 bis 3 halogen atoms, nitro or cyano; pyridyl which is unsubstituted or monosubstituted or disubstituted by independent substituents from the series consisting of $C_1$–$C_4$alkyl, $C_1$–$C_4$alkoxy, halogen, $C_1$–$C_2$haloalkyl having 1 to 3 halogen atoms, nitro or cyano.

3. A compound according to claim 1 in which:

$R_1$ is methyl;

$R_2$, $R_3$ and $R_5$ independently of one another are $C_1$–$C_2$alkyl, preferably methyl;

$R_4$ is hydrogen.

4. A compound according to claim 1 in which:

X is N;

Y is O; S, or S=O, preferably O;

Z is $OR_2$, $SR_2$, $N(R_3)H$; preferably $OR_2$, $SR_2$;

$R_2$ and $R_3$ are $C_1$–$C_2$alkyl, preferably methyl.

5. A compound according to claim 1 in which:

X is CH;

Y is O; S, or S=O, preferably O;

Z is $OR_2$;

$R_2$ is $C_1$–$C_2$alkyl, preferably methyl.

6. A compound according to claim 1, in which Y and Z together are a group

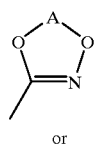

a)

or

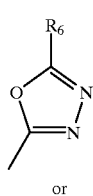

b)

or

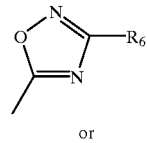

c)

or

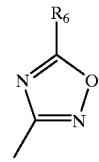

d)

and in which:

A is alkanediyl having 1 to 3 carbon atoms which is unsubstituted or substituted by methyl;

$R_6$ is hydrogen, $C_1$–$C_3$alkyl, cyclopropyl or $CF_3$.

7. A compound according to claim 1 in which:

V is —$CH_2$—, —$CH(CH_3)$—, —$CH(CH_3)_2$—, —$(CH_2)_2$—, —$(CH_2)_3$—;

U is O;

$R_{21}$ and $R_{22}$ independently of one another are hydrogen, chlorine, bromine, $C_1$–$C_4$alkyl, or $C_1$–$C_4$alkoxy;

$R_{23}$, $R_{24}$, $R_{25}$, $R_{26}$ are hydrogen.

8. A compound according to claim 1 in which:

X is CH or N;

Y is O;

Z is $OCH_3$ or $NHCH_3$;

V is —$CH_2$—;

U is O;

W is substituted or unsubstituted phenyl;

$R_{21}$ and $R_{22}$ independently of one another are hydrogen, chlorine or methyl;

$R_{23}$, $R_{24}$, $R_{25}$, $R_{26}$ are hydrogen.

9. A compound according to claim 1 in which:

W is phenyl which is unsubstituted or substituted by $C_1$–$C_8$alkyl, halo-$C_1$–$C_{6alkyl}$, $C_2$–$C_4$alkenyl, halo-$C_2$–$C_4$alkenyl, $C_2$–$C_4$alkynyl, halo-$C_2$–$C_4$alkynyl, $C_1$–$C_4$alkoxy, halo-$C_1$–$C_4$alkoxy, $C_2$–$C_6$alkenyloxy, halo-$C_2$–$C_4$alkenyloxy, $C_2$–$C_4$alkynyloxy, halo-$C_2$–$C_4$alkynyloxy, $C_1$–$C_4$alkoxycarbonyl, $C_{1-C6}$alkylcarbonyl, the abovementioned alkyl, alkenyl and alkynyl groups being unsubstituted or further substituted by aryl, hetaryl, aryloxy, hetaryloxy, arylsulfenyl, arylsulfinyl, arylsulfonyl, hetarylsulfenyl, hetarylsulfinyl or hetarylsulfonyl, each of which is unsubstituted or additionally substituted; furthermore aryl, hetaryl, heterocyclyl, arylcarbonyl, aryloxy, benzyl, cycloalkyl, cyclohexenyl, cyclohexenylalkoxy, cyclohexenylalkylthio, cyclohexadienyl, cyclohexadienylalkoxy, cyclohexadienylalkylthio, all the abovementioned cyclic groups being unsubstituted or mono- or polysubstituted by halogen, $C_{1-C4}$alkyl, $C_2$–$C_4$alkenyl, $C_2$–$C_4$alkynyl, $C_1$–$C_4$alkoxy, $C_1$–$C_4$alkylthio, $C_1$–$C_4$haloalkyl, $C_2$–$C_4$haloalkenyl, $C_2$–$C_4$haloalkynyl, $C_1$–$C_4$haloalkoxy, halogen, cyano, cyano-$C_1$–$C_2$alkyl, cyano-$C_1$–$C_2$alkoxy, OH, $NO_2$, SCN, thiocyanomethyl, $Si(CH_3)_3$, $NH_2$, $NH(C_1$–$C_4$alkyl), $N(C_1$–$C_4$alkyl)$_2$, $C_1$–$C_4$alkoxymethyl, $C_1$–$C_4$haloalkylcarbonyl, $C_1$–$C_4$haloalkyloxycarbonyl, $C_1$–$C_4$alkylcarbonyl, $C_1$–$C_4$alkoxycarbonyl, aminocarbonyl, $C_1$–$C_4$alkylaminocarbonyl, bis($C_1$–$C_4$alkylamino)carbonyl, arylaminocarbonyl, arylaminothiocarbonyl, $C_1$–$C_4$alkoximinomethyl, —CSNH$_2$, —SH, $C_1$–$C_4$alkylthiomethyl, $C_2$–$C_4$alkenyloxy, $C_2$–$C_4$alkynyloxy, $C_2$–$C_4$haloalkenyloxy, $C_1$–$C_4$alkylsulfinylmethyl, $C_1$–$C_4$-alkylsulfonylmethyl, phenylsulfinylmethyl, phenylsulfonylmethyl, trifluoromethylsulfonyl, $C_3$–$C_6$cycloalkyl, $C_1$–$C_4$haloalkylcarbonyloxy, $C_1$–$C_4$alkylcarbonyloxy, $C_1$–$C_4$alkoxycarbonyloxy, haloalkoxycarbonyloxy, aminocarbonyloxy, $C_1$–$C_4$alkylaminocarbonyloxy, bis($C_1$–$C_4$alkylamino)carbonyloxy, arylaminocarbonyloxy or arylaminothiocarbonyloxy.

10. A compound according to claim 1 in which:

V is —CH$_2$—, —CH(CH$_3$)—, —CH(CH$_3$)$_2$—, —(CH$_2$)$_2$—, —(CH$_2$)$_3$—;

U is S or NR$_7$;

$R_{21}$ and $R_{22}$ independently of one another are halogen, chlorine, bromine, $C_1$–$C_4$alkyl or $C_1$–$C_4$alkoxy;

$R_{23}$, $R_{24}$, $R_{25}$, $R_{26}$ are hydrogen.

11. A compound according to claim 2 in which:

D is halogen, $C_1$–$C_4$alkyl, halo-$C_1$–$C_4$alkyl, $C_2$–$C_4$alkenyl, $C_2$–$C_4$alkynyl, free or chlorinated cyclopropylmethyl, $C_1$–$C_4$alkoxy, halo-$C_1$–$C_4$alkoxy, $C_2$–$C_{12}$alkoxyalkyl, $C_1$–$C_4$ acyl, $C_1$–$C_4$alkoxycarbonyl, free or chlorinated cyclopropylmethyloxy, or substituted or unsubstituted aryl, substituted or unsubstituted aryloxy, or substituted or unsubstituted benzyl, where the substituents on phenyl, phenoxy and benzyl are selected from the series consisting of halogen, nitro, $C_1$–$C_2$alkyl, halo-$C_1$–$C_2$alkyl, $C_2$–$C_4$alkenyl, $C_2$–$C_4$alkynyl, $C_1$–$C_2$alkoxy, halo-$C_1$–$C_2$alkoxy, $C_2$–$C_{12}$alkoxyalkyl;

n is 0, 1, 2 or 3.

12. A compound according to claim 11, in which:

D is halogen, $C_1$–$C_4$alkyl, halo-$C_1$–$C_4$alkyl, $C_2$–$C_4$alkenyl, $C_2$–$C_4$alkynyl, free or chlorinated cyclopropylmethyl, $C_1$–$C_4$alkoxy, halo-$C_1$–$C_4$alkoxy, $C_1$–$C_4$ acyl, $C_1$–$C_4$alkoxycarbonyl, optionally chlorinated cyclopropylmethyloxy;

n is 0, 1 or 2.

13. A compound according to claim 2, in which:

D is the group

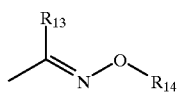

in which $R_{13}$ is hydrogen, cyano, $C_1$–$C_4$alkyl, cyclopropyl, $C_1$–$C_4$alkoxycarbonyl, $C_1$–$C_4$acyl, $C_1$–$C_2$alkoxyimino-$C_1$–$C_6$alkyl, or the group

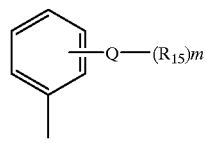

$R_{15}$ is $C_1$–$C_4$alkyl, halo-$C_1$–$C_6$alkyl, $C_1$–$C_6$alkoxy, halo-$C_1$–$C_6$alkoxy, halogen, $C_3$–$C_6$cycloalkyl, which is unsubstituted or substituted by 1 to 5 halogen atoms, $C_2$–$C_6$alkenyl; halo-$C_2$–$C_6$alkenyl, substituted or unsubstituted $C_2$–$C_6$alkynyl; aryl, hetaryl or heterocyclyl, all three of which independently of one another are unsubstituted or monosubstituted to pentasubstituted by $C_1$–$C_6$alkyl, halo-$C_1$–$C_6$alkyl, halogen, $C_1$–$C_6$alkoxy or halo-$C_1$–$C_6$alkoxy; tri($C_1$–$C_4$-alkyl)silyl, di($C_1$–$C_4$alkyl)phenylsilyl;

where, if m is greater than 1, it is possible for the radicals $R_{15}$ to be identical or different;

Q is a direct bond, $C_1$–$C_8$alkylene, $C_2$–$C_6$alkenylene, $C_2$–$C_6$alkynytene, O, O($C_1$–$C_6$alkylene), ($C_1$–$C_6$alkylene)O, S(=O)$_p$, S(=O)$_p$($C_1$–$C_6$alkylene) or ($C_1$–$C_6$alkylene)S(=O)$_p$;

n is 0, 1, 2, or 3;

m is 0, 1, 2, or 3;

p is 0, 1 or 2; and $R_{14}$ is hydrogen; $C_1$–$C_4$alkyl; $C_1$–$C_4$haloalkyl having 1 to 6 halogen atoms; $C_2$–$C_4$alkenyl; $C_2$–$C_4$haloalkenyl having 1 to 3 halogen atoms.

14. A compound according to claim 13, in which:

$R_{15}$ is $C_1$–$C_6$alkyl, halo-$C_1$–$C_6$alkyl, cyclopropyl which is unsubstituted or substituted by 1 to 5 chlorine atoms, $C_2$–$C_6$alkenyl which is unsubstituted or substituted by 1 to 3 halogen atoms, or unsubstituted or substituted $C_2$–$C_6$alkynyl; furthermore phenyl, which is unsubstituted or monosubstituted to pentasubstituted by $C_1$–$C_6$alkyl, halo-$C_1$–$C_6$alkyl, halogen, $C_1$–$C_6$alkoxy or halo-$C_1$–$C_6$alkoxy; or pyridyl which is unsubstituted or monosubstituted to pentasubstituted by $C_1$–$C_6$alkyl, halo-$C_1$–$C_6$alkyl, halo, $C_1$–$C_6$alkoxy or halo-$C_1$–$C_6$alkoxy;

Q is a direct bond, $C_1$–$C_4$alkylene, O, O($C_1$–$C_4$alkylene), ($C_1$–$C_4$alkylene)O, m is 0, 1, 2.

15. A compound according to claim 13, in which:

$R_{13}$ is hetaryl or heterocyclyl, which, independently of one another, are unsubstituted or monosubstituted to pentasubstituted by $C_1$–$C_6$alkyl, halo-$C_1$–$C_6$alkyl, halogen, $C_1$–$C_6$-alkoxy or halo-$C_1$–$C_6$alkoxy.

16. A compound of the formula I according to claim 1, in which:

W is substituted or unsubstituted pyridyl, pyrimidinyl, imidazolyl, thiazolyl, 1,3,4-thiadiazolyl, triazolyl, thienyl, furanyl, pyrrolyl, quinolyl, isoquinolyl, benzoxazolyl, quinoxalinyl, benzothiazolyl, benzimidazolyl, or indolyl.

17. A compound of the formula I according to claim 16, in which:

W is pyridyl or pyrimidinyl, each of which is unsubstituted or substituted by $C_1$–$C_4$alkyl, halo-$C_1$–$C_4$alkyl, $C_2$–$C_6$alkenyl, halo-$C_2$–$C_6$alkenyl, $C_2$–$C_6$alkynyl, halo-$C_2$–$C_6$alkynyl, $C_1$–$C_4$alkoxy, halo-$C_1$–$C_4$alkoxy, $C_2$–$C_{12}$alkoxyalkyl, $C_1$–$C_6$acyl, $C_1$–$C_4$alkoxycarbonyl, substituted or unsubstituted phenyl, substituted or unsubstituted phenoxy, or substituted or unsubstituted benzyl.

18. A compound of the formula I according to claim 17, in which:

V is a direct bond or —CH$_2$—;

U is O;

W is pyridyl or pyrimidinyl, each of which is unsubstituted or substituted by $C_1$–$C_4$alkyl, halo-$C_1$–$C_4$alkyl, phenyl, phenoxy or benzyl and in which phenyl, phenoxy and benzyl are unsubstituted or monosubstituted to trisubstituted by halogen, $C_1$–$C_4$alkyl, $C_2$–$C_4$alkenyl, halo-$C_1$–$C_4$alkyl, halo-$C_2$–$C_4$alkenyl, $C_1$–$C_4$alkoxy, halo-$C_1$–$C_6$alkoxy or cyano.

19. A compound of the formula XIV

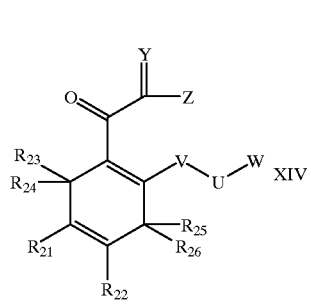

XIV in which Y, Z, V, U, W and $R_{21}$ to $R_{26}$ have the meanings given for formula I according to claim 1.

20. A composition for controlling pests selected from the group consisting of phytopathogenic fungi, insects and representatives of the order acarina which comprises, as active ingredient, an effective amount of a compound according to claim 1 together with a suitable carrier material.

21. A process for the preparation of a compound of the formula I according to claim 1, which comprises reacting a compound of the formula II with a compound of the formula III

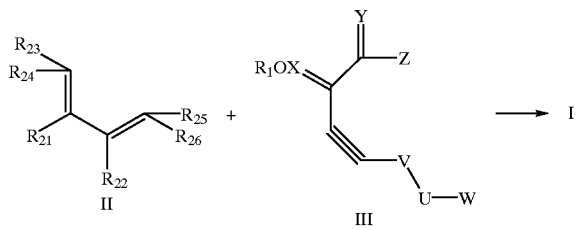

in which X, Y, Z, $R_1$, V, U, W and $R_{21}$ to $R_{26}$ have the meanings given for formula I.

22. A process for the preparation of a compound of the formula I according to claim 1, which comprises reacting a compound of the formula IV with a compound of the formula V

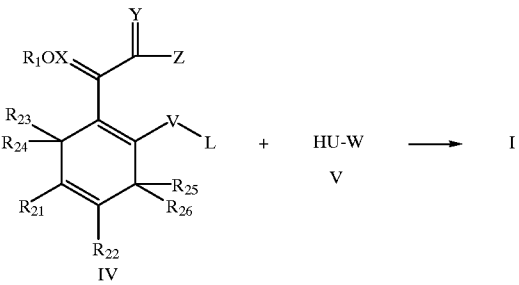

in which X, Y, Z, $R_1$, V, U, $R_{21}$ to $R_{26}$ and W have the meanings given for formula I and in which L is a leaving group, in a solvent under alkaline conditions.

23. A method of controlling and preventing pests selected from the group consisting of phytopathogienic fungi, insects and representatives of the order acarina, which comprises applying a compound according to claim 1 to the pests or their environment.

24. A method according to claim 23, the pests being phytopathogenic fungi.

25. A method according to claim 23, the pests being insects or Acarina.

26. A method according to claim 23, in which seed is treated.

* * * * *